(12) United States Patent
Beers et al.

(10) Patent No.: US 9,493,698 B2
(45) Date of Patent: Nov. 15, 2016

(54) ORGANIC ELECTROLUMINESCENT MATERIALS AND DEVICES

(75) Inventors: Scott Beers, Flemington, NJ (US); Chuanjun Xia, Lawrenceville, NJ (US); Jason Brooks, Philadelphia, PA (US); Gregg Kottas, Ewing, NJ (US)

(73) Assignee: UNIVERSAL DISPLAY CORPORATION, Ewing, NJ (US)

(*) Notice: Subject to any disclaimer, the term of this patent is extended or adjusted under 35 U.S.C. 154(b) by 756 days.

(21) Appl. No.: 13/584,483

(22) Filed: Aug. 13, 2012

(65) Prior Publication Data

US 2013/0048963 A1 Feb. 28, 2013

Related U.S. Application Data

(60) Provisional application No. 61/529,634, filed on Aug. 31, 2011.

(51) Int. Cl.

| | |
|---|---|
| *H01L 51/54* | (2006.01) |
| *C09K 11/06* | (2006.01) |
| *C07F 15/00* | (2006.01) |
| *H05B 33/18* | (2006.01) |
| *H01L 51/00* | (2006.01) |
| *H01L 51/50* | (2006.01) |

(52) U.S. Cl.
CPC ............ *C09K 11/06* (2013.01); *C07F 15/0086* (2013.01); *H01L 51/0087* (2013.01); *H05B 33/18* (2013.01); *C09K 2211/1029* (2013.01); *C09K 2211/1044* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Baldo et al., "Highly Efficient Phosphorescent Emission from Organic Electroluminescent Devices," Nature, vol. 395, 151-154, (1998).

(Continued)

*Primary Examiner* — Marie R. Yamnitzky
(74) *Attorney, Agent, or Firm* — Duane Morris LLP

(57) ABSTRACT

Novel phosphorescent tetradentate platinum (II) compounds are provided. The compounds contain an isoimidazole moiety, optionally further substituted with a twisted aryl. These compounds may be advantageously used in OLEDs.

20 Claims, 4 Drawing Sheets

(56) References Cited

U.S. PATENT DOCUMENTS

| | | |
|---|---|---|
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,566,505 B2 | 7/2009 | Ise et al. |
| 7,655,323 B2 | 2/2010 | Walters et al. |
| 7,771,845 B2 | 8/2010 | Sano et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0227112 A1 | 10/2005 | Ise et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0073359 A1* | 4/2006 | Ise et al. ............... 428/690 |
| 2006/0202194 A1 | 9/2006 | Jeong et al. |
| 2006/0210831 A1* | 9/2006 | Sano et al. ............. 428/690 |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0001530 A1* | 1/2008 | Ise et al. ............... 313/504 |
| 2008/0015355 A1 | 1/2008 | Schafer et al. |
| 2008/0018221 A1 | 1/2008 | Egen et al. |
| 2008/0038586 A1 | 2/2008 | Nishizeki et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0079340 A1* | 3/2009 | Kinoshita et al. ......... 313/504 |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0198069 A1 | 8/2009 | Umakoshi et al. |
| 2011/0049496 A1 | 3/2011 | Fukuzaki |
| 2012/0223634 A1 | 9/2012 | Xia et al. |

FOREIGN PATENT DOCUMENTS

| | | |
|---|---|---|
| EP | 2034538 | 3/2009 |
| EP | 2123640 | 11/2009 |
| JP | 200511610 | 1/2005 |
| JP | 2006060198 | 3/2006 |
| JP | 2007123392 | 5/2007 |
| JP | 2007254297 | 10/2007 |
| JP | 2008074939 | 4/2008 |
| JP | 2008074940 | 4/2008 |
| JP | 2009267171 | 11/2009 |
| JP | 2009267244 | 11/2009 |
| JP | 2009272339 | 11/2009 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | 200603340 A1 | 3/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008035664 | 3/2008 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009021126 | 2/2009 |
| WO | WO 2009050290 | 4/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |

OTHER PUBLICATIONS

Baldo et al., "Very high-efficiency green organic light-emitting devices based on electrophosphorescence," Appl. Phys. Lett., vol. 75, No. 1, 4-6 (1999).

Search Report corresponding to European patent application No. 12 17 7646, (dated Nov. 20, 2012).

Search Report corresponding to European patent application No. 12 18 2336, (dated Nov. 7, 2012).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral $Ru^{II}$ PHosphorescent Emitters," *Adv. Mater.*, 17(8):1059-1064 (2005).

(56) References Cited

OTHER PUBLICATIONS

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).
Wong, Wai-Yeung, "Multifunctional Iridium Complexes Based on Carbazole Modules as Highly Efficient Electrophosphors," *Angew. Chem. Int. Ed.*, 45:7800-7803 (2006).
Tang, C.W. and VanSlyke, S.A., "Organic Electroluminescent Diodes," *Appl. Phys. Lett.*, 51(12):913-915 (1987).
Adachi, Chihaya et al., "Organic Electroluminescent Device Having a Hole Conductor as an Emitting Layer," *Appl. Phys. Lett.*, 55(15):1489-1491 (1989).
Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).
Gao, Zhiqiang et al., "Bright-Blue Electroluminescence From a Silyl-Substituted ter-(phenylene-vinylene) derivative," *Appl. Phys. Lett.*, 74(6):865-867 (1999).
Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).
Hung, L.S. et al., "Anode Modification in Organic Light-Emitting Diodes by Low-Frequency Plasma Polymerization of $CHF_3$,"*Appl. Phys. Lett.*, 78(5):673-675 (2001).
Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).
Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1):162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).
Aonuma, Masaki et al., "Material Design of Hole Transport Materials Capable of Thick-Film Formation in Organic Light Emitting Diodes," *Appl. Phys. Lett.*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *Appl. Phys. Lett.*, 78(11):1622-1624 (2001).
Wong, Keith Man-Chung et al.,"A Novel Class of Phosphorescent Gold(III) Alkynyl-Based Organic Light-Emitting Devices with Turnable Colour," *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," *Chem. Lett.*, 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).
Mi, Bao-Xiu et al., "Thermally Stable Hole-Transporting Material for Organic Light-Emitting Diode: an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).
Niu, Yu-Hua et al., "Highly Efficient Electrophosphorescent Devices with Saturated Red Emission from a Neutral Osmium Complex," *Chem. Mater.*, 17(13):3532-3536 (2005).
Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," *Inorg. Chem.*, 46(10):4308-4319 (2007).
Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota,Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," *J. Am. Chem. Soc.*, 120 (37):9714-9715 (1998).
Sakamoto, Youichi et al., "Synthesis, Characterization, and Electron-Transport Property of Perfluorinated Phenylene Dendrimers," *J. Am. Chem. Soc.*, 122(8):1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko et al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al.,"1,2,4-Triazole Derivative as an Electron Transport Layer in Organic Electroluminescent Devices," *Jpn. J. Appl. Phys.*, 32:L917-L920 (1993).
Van Slyke, S. A. et al., "Organic Electroluminescent Devices with Improved Stability," *Appl. Phys. Lett.*, 69(15 ):2160-2162 (1996).
Guo, Tzung-Fang et al., "Highly Efficient Electrophosphorescent Polymer Light-Emitting Devices," *Organic Electronics*, 1:15-20 (2000).
Palilis, Leonidas C., "High Efficiency Molecular Organic Light-Emitting Diodes Based On Silole Derivatives And Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergård et al., "Langmuir-Blodgett Light-Emitting Diodes Of Poly(3-Hexylthiophene): Electro-Optical Characteristics Related to Structure," *Synthetic Metals*, 87:171-177 (1997).
Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).
Salbeck, J. et al., "Low Molecular Organic Glasses for Blue Electroluminescence," *Synthetic Metals*, 91:209-215 (1997).
First Office Action and Search Report dated Dec. 31, 2015 issued for corresponding Chinese Patent Application No. 201210509714.6.

\* cited by examiner

ORGANIC ELECTROLUMINESCENT MATERIALS AND DEVICES

This application is a non-provisional application of, and claims priority to, U.S. Provisional application No. 61/529,634 filed Aug. 31, 2011, the disclosure of which is hereby expressly incorporated herein by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds suitable for incorporation into OLED devices, specifically the compounds comprise tetradentate platinum complexes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

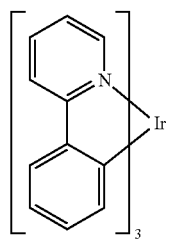

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Tetradentate platinum(II) complexes comprising an isoimidazole ligand are provided. The compounds have the formula:

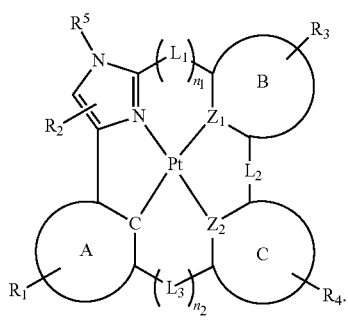

Formula I

A, B, and C are each independently a 5- or 6-membered carbocyclic or heterocyclic ring. $L_1$ and $L_3$ are independently selected from the group consisting of a single bond, BR, NR, PR, O, S, Se, C=O, S=O, $SO_2$, CRR', SiRR', and GeRR'. $L_2$ is selected from the group consisting of BR, NR, PR, O, S, Se, C=O, S=O, $SO_2$, CRR', SiRR', and GeRR'. $n_1$ is 0 or 1. $n_2$ is 0 or 1. $n_1+n_2$ is at least equal to 1. $Z_1$ and $Z_2$ are independently a nitrogen atom or a carbon atom. $R_1$, $R_2$, $R_3$, and $R_4$ may represent mono-, di-, tri-, or tetra-substitutions. R, R', $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R_1$ is optionally fused to A. $R_3$ is optionally fused to B. $R_4$ is optionally fused to C. $R_3$ and $R_4$ are optionally joined to form into a ring. $R_3$ and $L_2$ are optionally joined to form into a ring. $R_4$ and $L_2$ are optionally joined to form into a ring.

In one aspect, $R_5$ is a substituted aryl. Preferably, $R_5$ is a 2,6-disubstituted aryl. More preferably, $R_5$ is

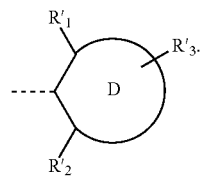

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. D is 5-membered or 6-membered carbocyclic or heterocyclic ring that is optionally further substituted with $R'_3$, which is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, each of $R'_1$ and $R'_2$ is not hydrogen or deuterium. In another aspect, at least one of $R'_1$ and $R'_2$ is an alkyl. In yet another aspect, each of $R'_1$ and $R'_2$ is an alkyl. In a further aspect, at least one of $R'_1$ and $R'_2$ is an alkyl containing at least 2 carbons. In another aspect, at least one of $R'_1$ and $R'_2$ is an aryl. In yet another aspect, each of $R'_1$ and $R'_2$ is an aryl.

In one aspect, the compound has a neutral charge. In another aspect, two of A, B, and C are phenyl and one of A, B, and C is pyridine.

In one aspect, the compound has the formula:

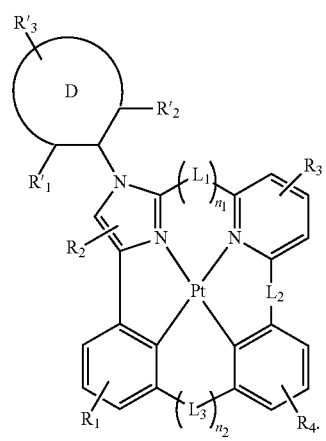

Formula II

In another aspect, the compound has the formula:

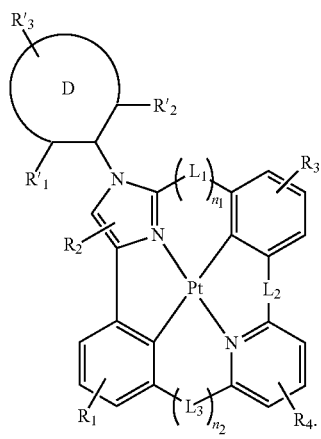

Formula III

In yet another aspect, the compound has the formula:

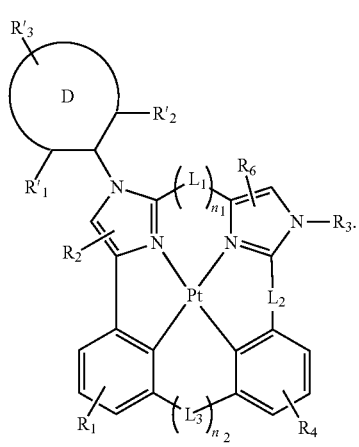

Formula IV

In a further aspect, the compound has the formula:

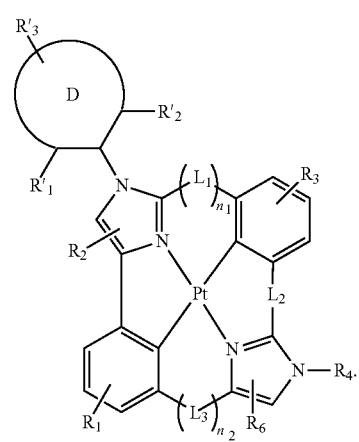

Formula V

In another aspect, the compound has the formula:

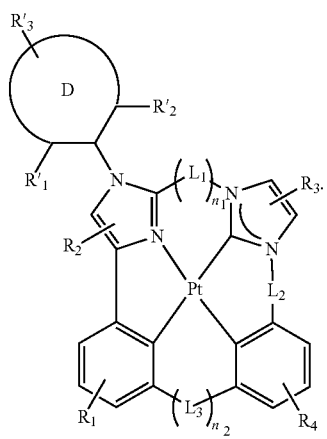

Formula VI

In yet another aspect, the compound has the formula:

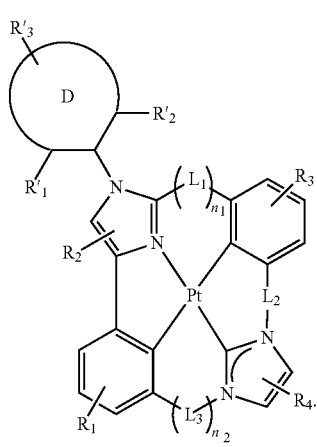

Formula VII

In one aspect, $L_1$ or $L_3$ is selected from the group consisting of O, S, $CH_2$, $CR'_2$, NR', $SiR'_2$ or BR'. R' is alkyl or aryl. In another aspect, $L_2$ is selected from the group consisting of O, S, $CH_2$, $CR'_2$, NR', and $SiR'_2$. R' is alkyl or aryl, and R' is optionally bonded to B or C.

In one aspect, $R_1$, $R_2$, $R_3$ and $R_4$ are each independently selected from the group consisting of hydrogen, deuterium, alkyl, aryl, cyclic alkyl, branched alkyl, heteroaryl, and fused aryl.

Specific, non-limiting examples of the tetradentate platinum (II) complex are provided. In one aspect, the compound is selected from the group consisting of:

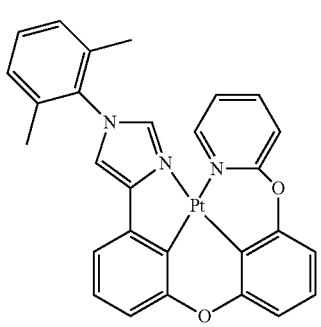

Compound 1

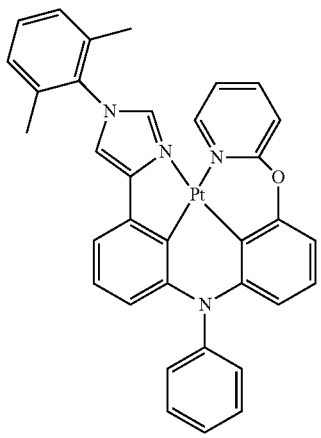

Compound 2

Compound 3
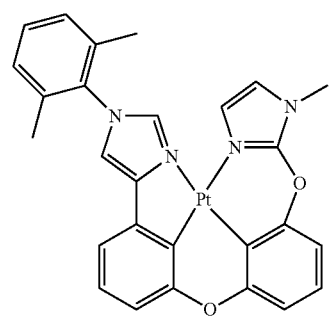
Compound 4
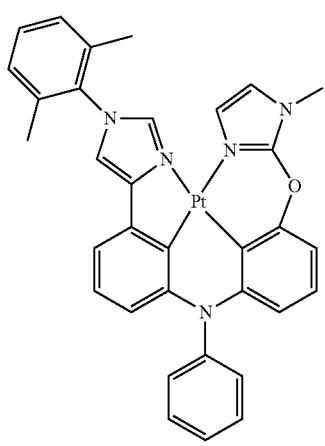
Compound 5
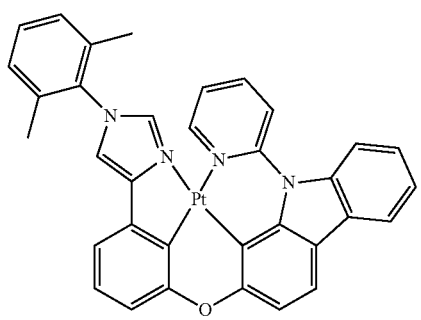
Compound 6
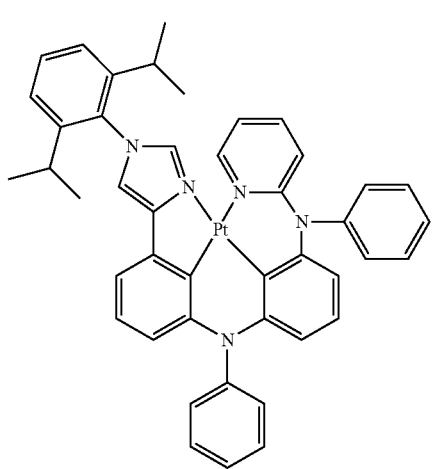
Compound 7
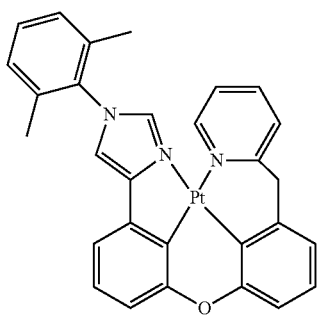
Compound 8
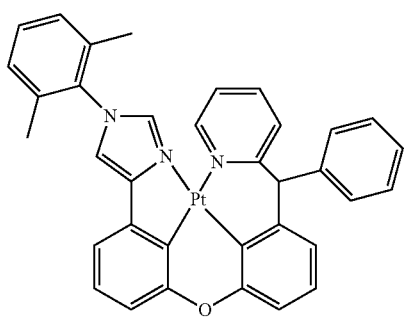
Compound 9
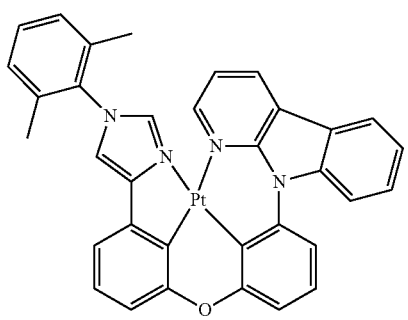
Compound 10
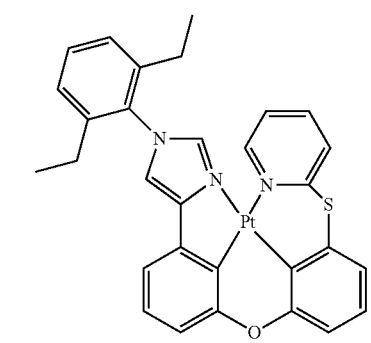
Compound 11
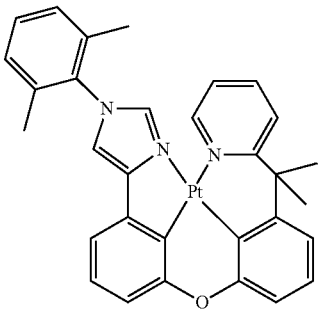

Compound 12
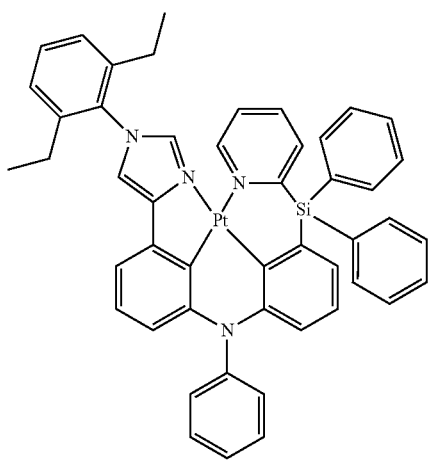
Compound 13
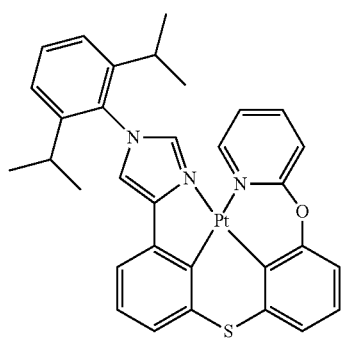
Compound 14
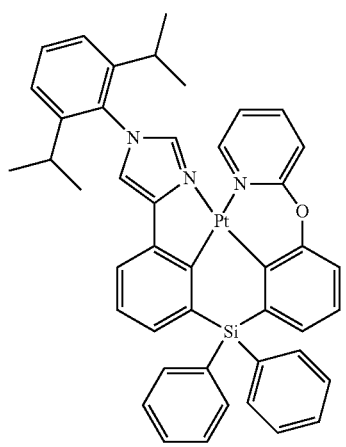
Compound 15
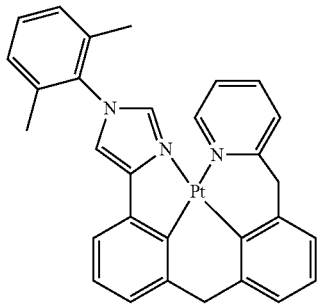
Compound 16
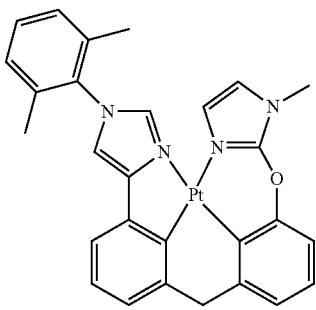
Compound 17
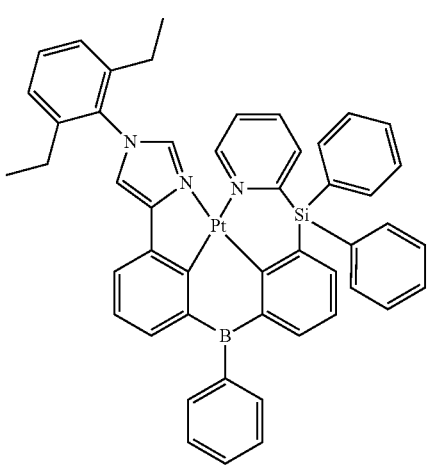
Compound 18
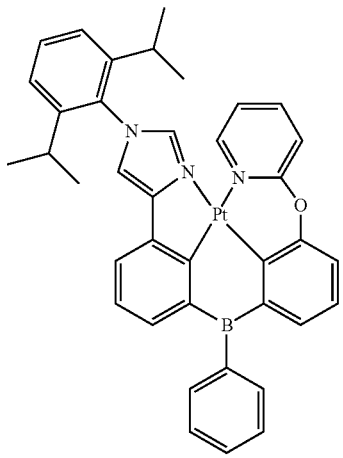
Compound 19
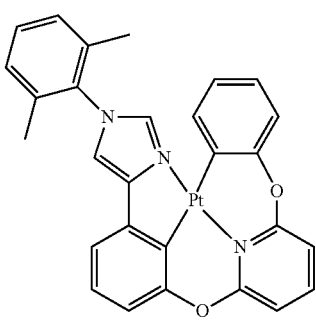

Compound 20
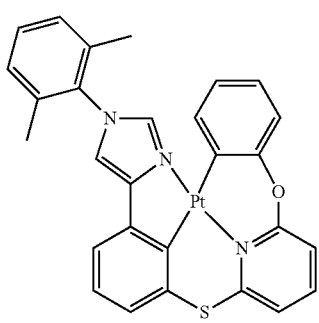
Compound 24
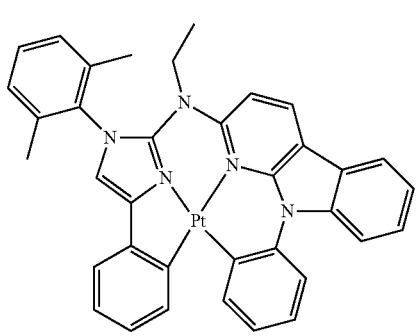
Compound 21
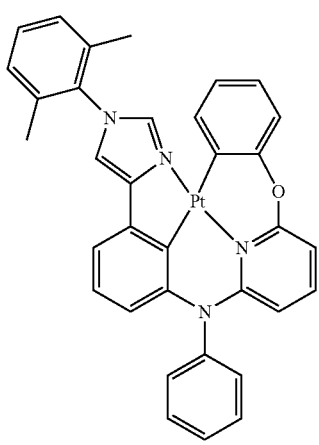
Compound 25
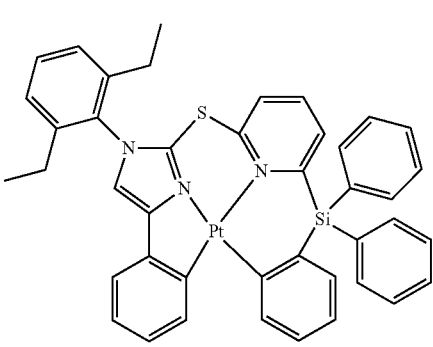
Compound 22
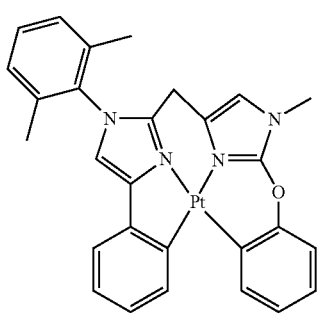
Compound 26
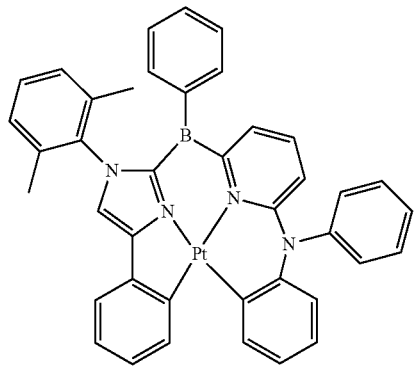
Compound 23
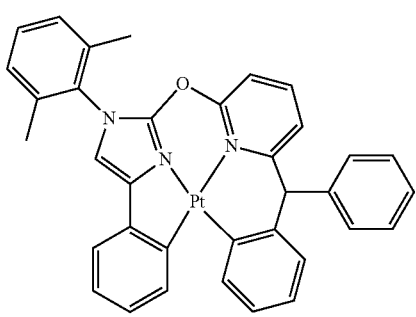
Compound 27
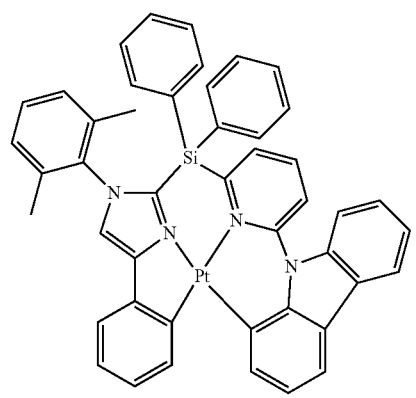

Compound 28
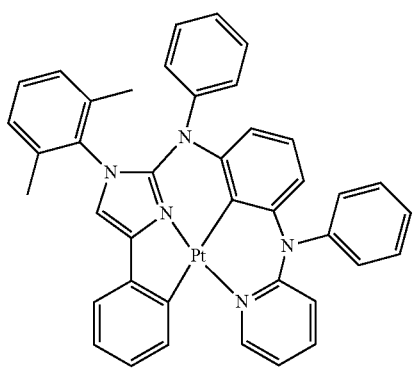
Compound 29
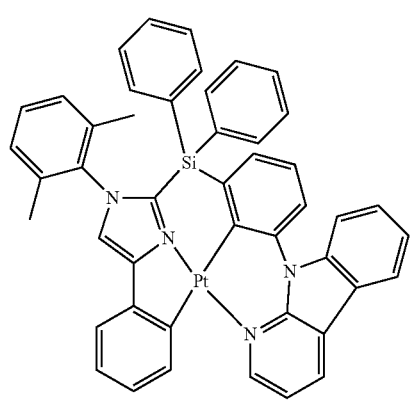
Compound 30
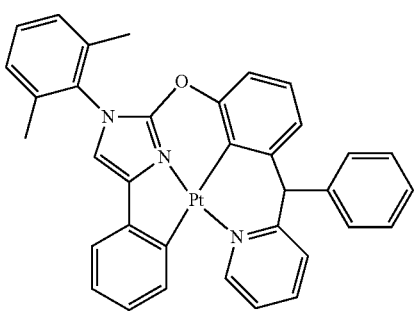
Compound 31
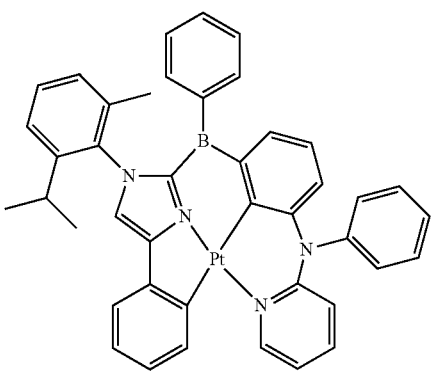
Compound 32
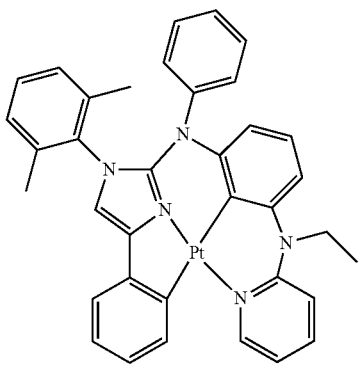
Compound 33
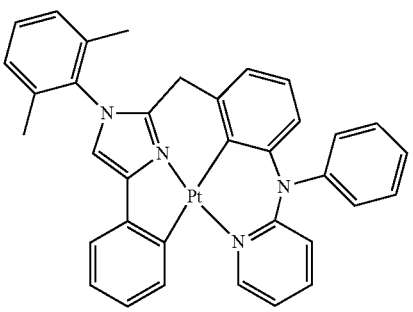
Compound 34
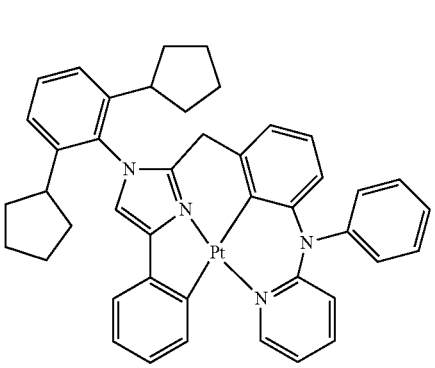
Compound 35
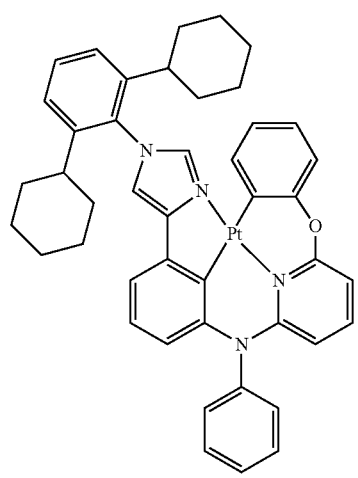

-continued
Compound 36
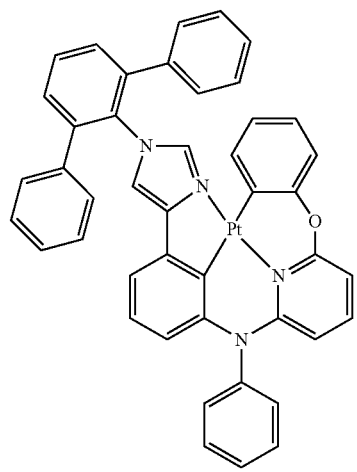
Compound 37
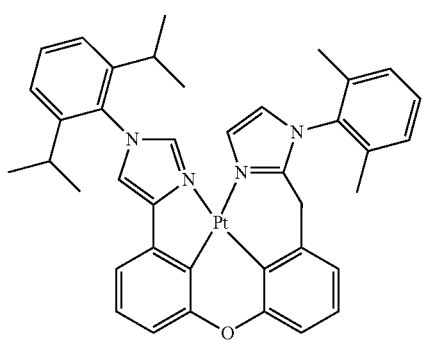
Compound 38
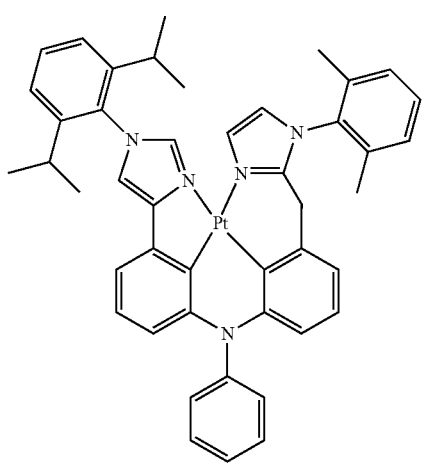
-continued
Compound 39
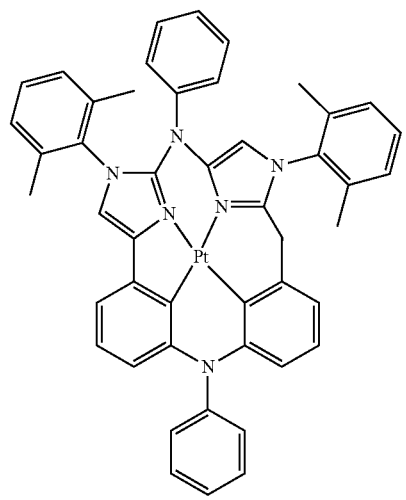
Compound 40
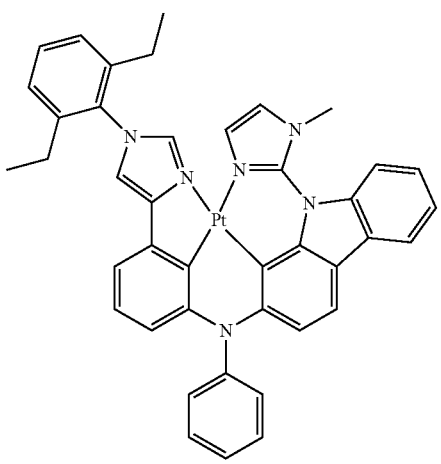
Compound 41
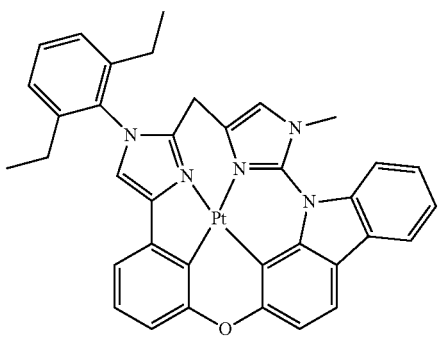

Compound 42
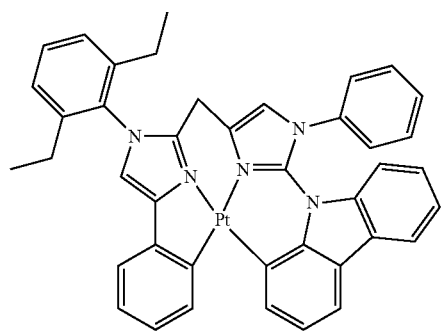
Compound 43
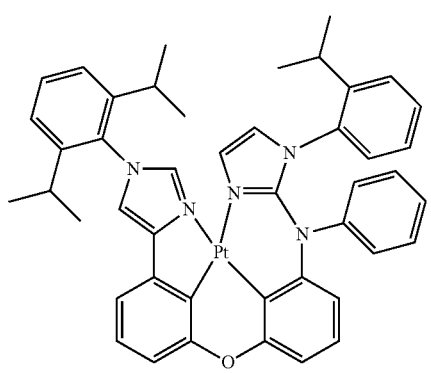
Compound 44
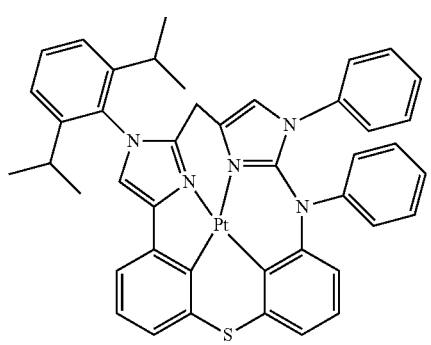
Compound 45
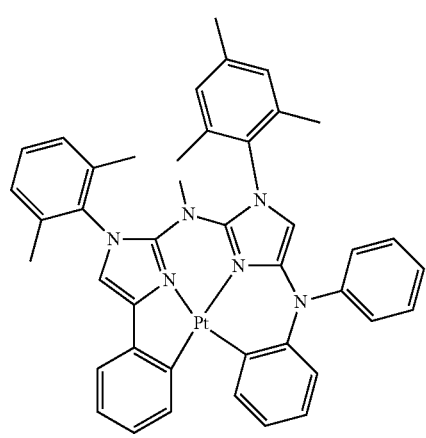
Compound 46
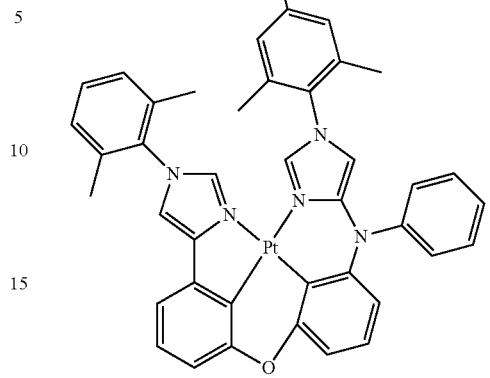
Compound 47
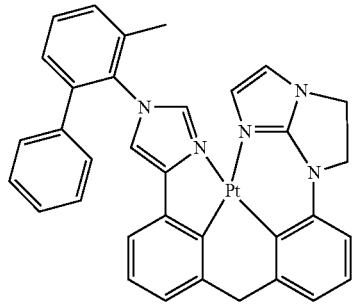
Compound 48
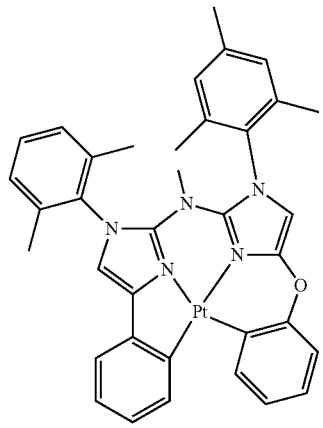
Compound 49
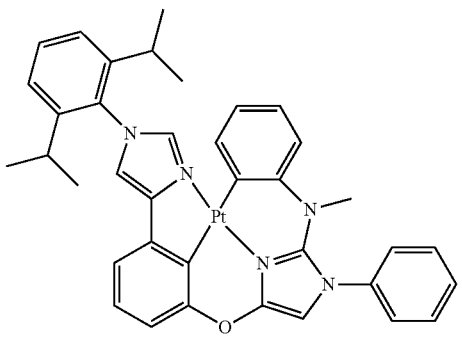

Compound 50
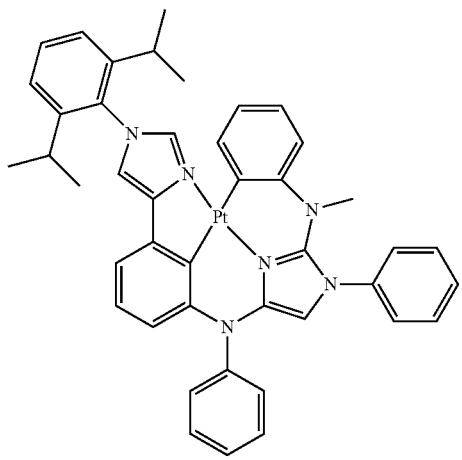
Compound 51
Compound 52
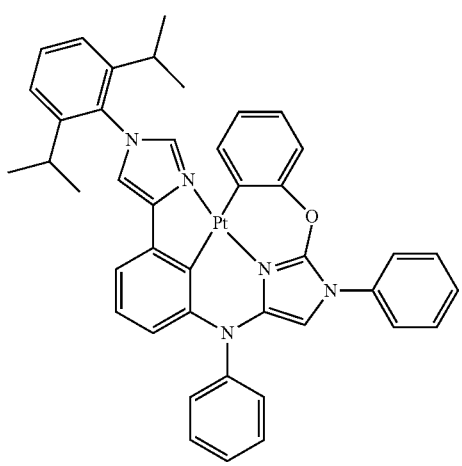
Compound 53
Compound 54
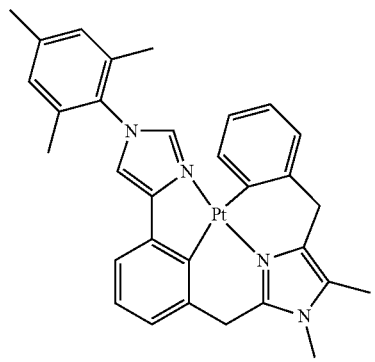
Compound 55
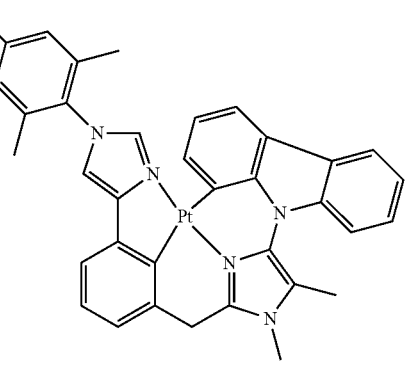
Compound 56
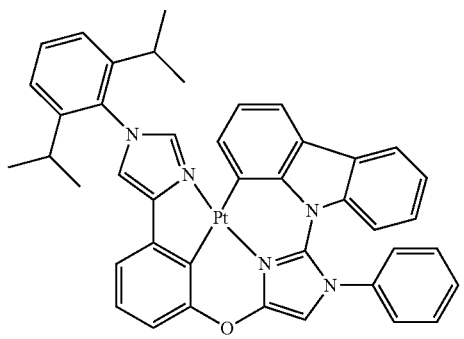
Compound 57
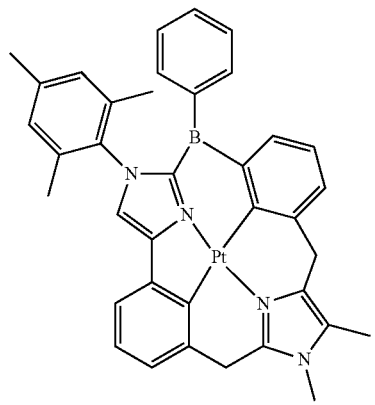

Compound 58
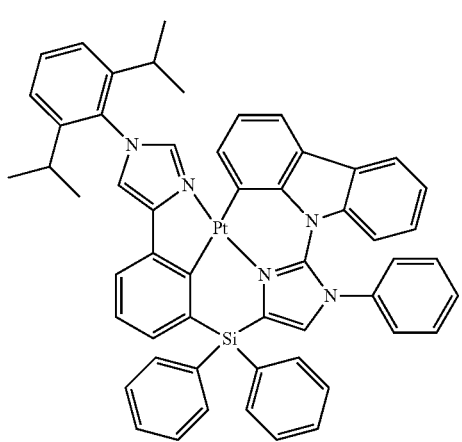
Compound 59
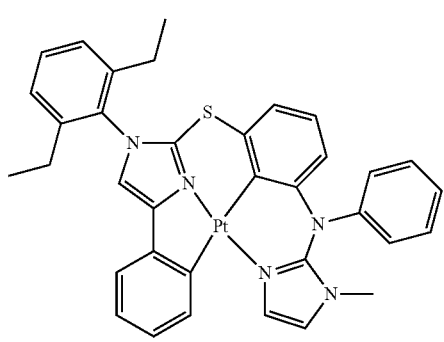
Compound 60
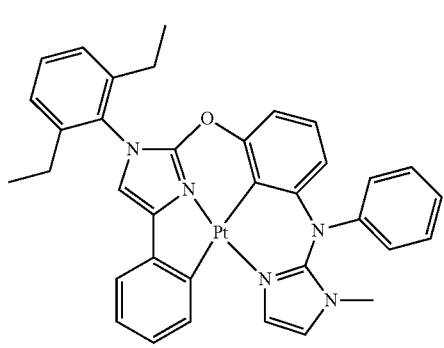
Compound 61
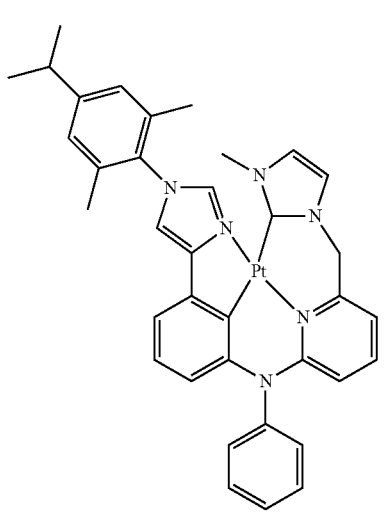
Compound 62
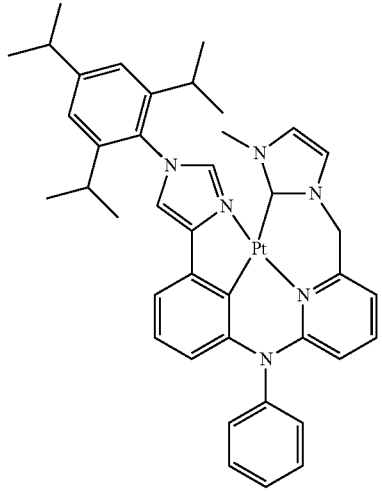
Compound 63
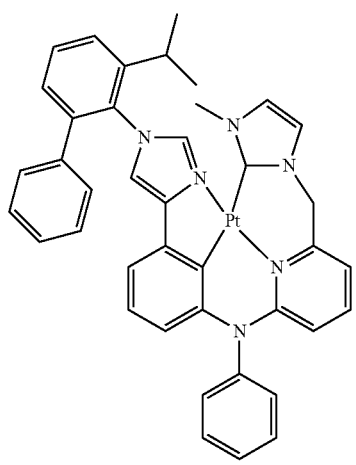
Compound 64

Compound 65
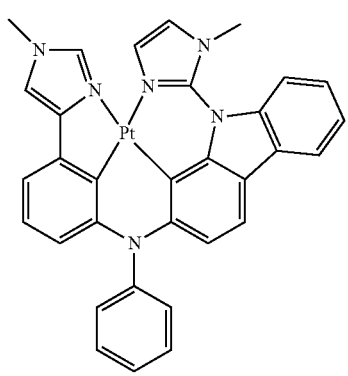
Compound 66
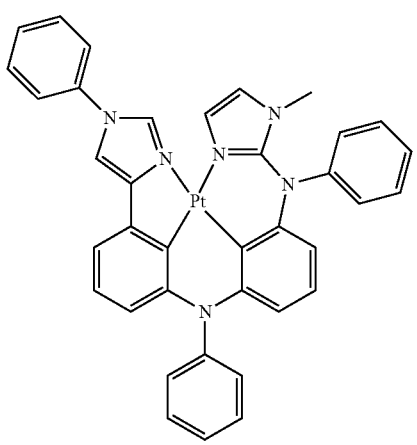
Compound 67
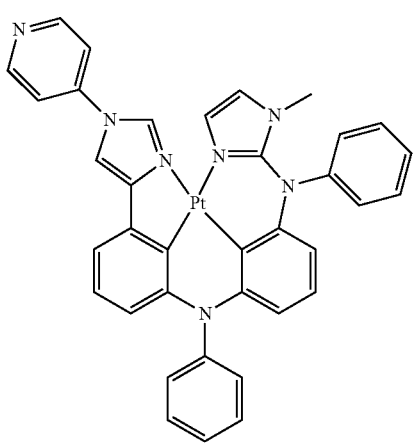
Compound 68
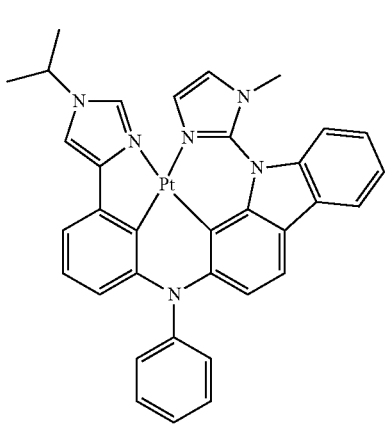
Compound 69
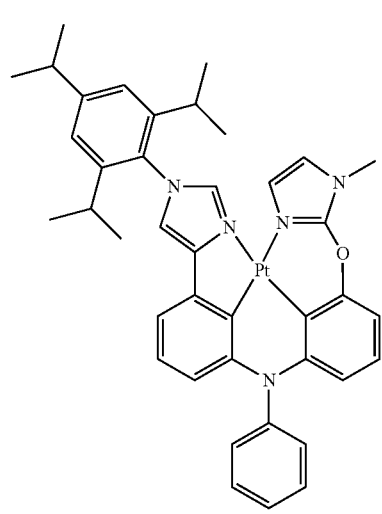
Compound 70
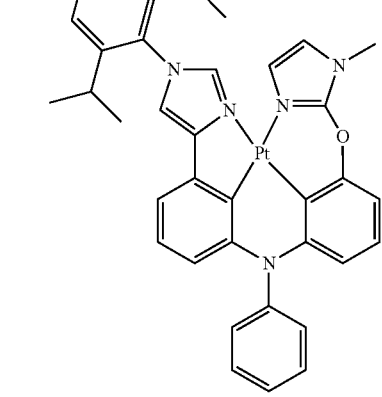

Compound 71
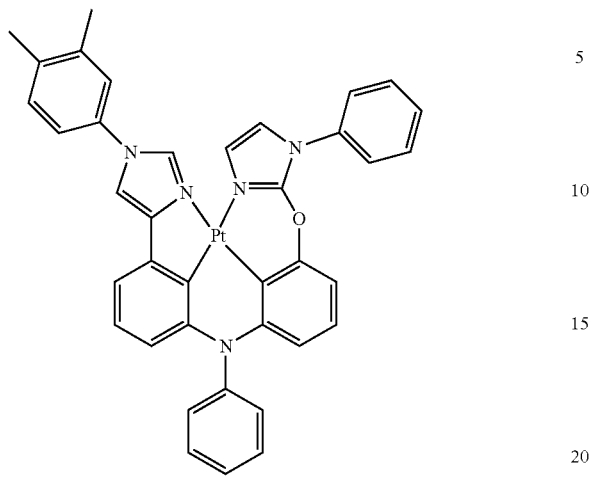
Compound 72
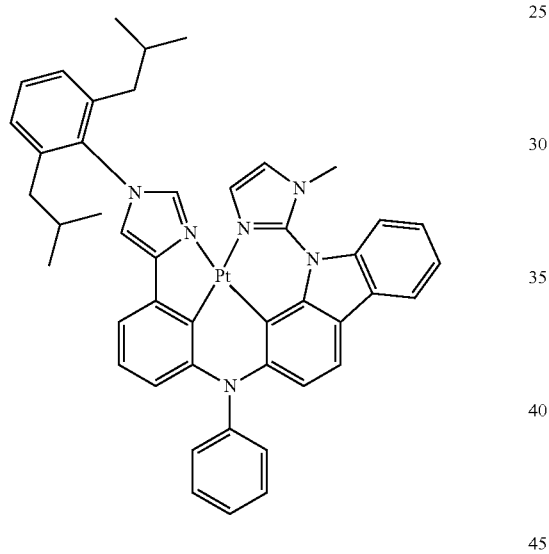
Compound 73
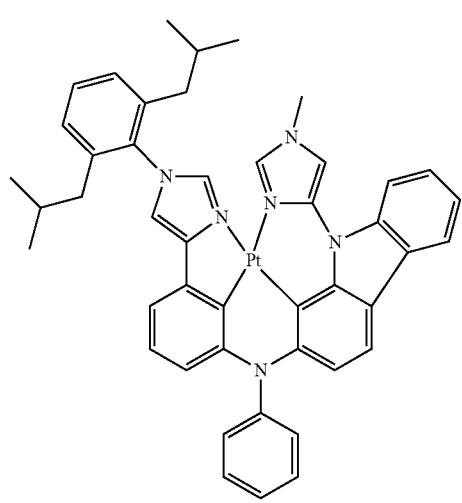
Compound 74
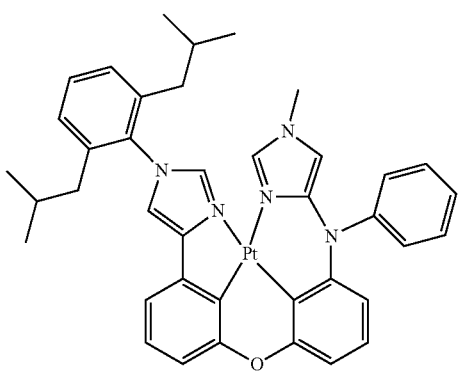
Compound 75
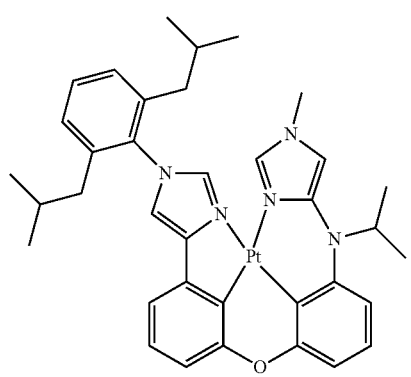
Compound 76
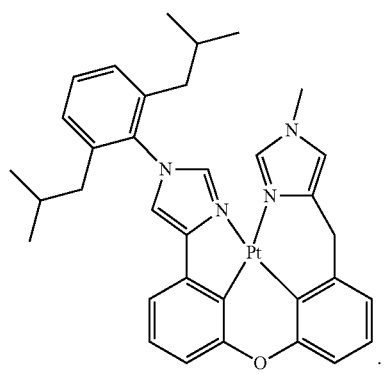
Additionally, a first device is provided. The first device comprises a first organic light emitting device. The organic light emitting device further comprises an anode, a cathode, and an organic layer, disposed between the anode and the cathode. The organic layer comprises a compound having the formula:

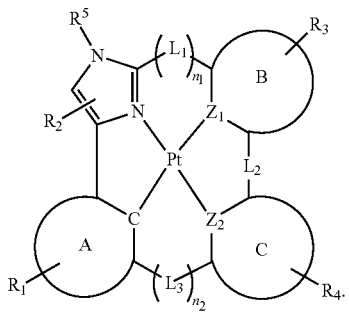

Formula I

A, B, and C are each independently a 5- or 6-membered carbocyclic or heterocyclic ring. $L_1$ and $L_3$ are independently selected from the group consisting of a single bond, BR, NR, PR, O, S, Se, C=O, S=O, $SO_2$, CRR', SiRR', and GeRR'. $L_2$ is selected from the group consisting of BR, NR, PR, O, S, Se, C=O, S=O, $SO_2$, CRR', SiRR', and GeRR'. $n_1$ is 0 or 1. $n_2$ is 0 or 1. $n_1+n_2$ is at least equal to 1. $Z_1$ and $Z_2$ are independently a nitrogen atom or a carbon atom. $R_1$, $R_2$, $R_3$, and $R_4$ may represent mono-, di-, tri-, or tetra-substitutions. R, R', $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R_1$ is optionally fused to A. $R_3$ is optionally fused to B. $R_4$ is optionally fused to C. $R_3$ and $R_4$ are optionally joined to form into a ring. $R_3$ and $L_2$ are optionally joined to form into a ring. $R_4$ and $L_2$ are optionally joined to form into a ring.

The various specific aspects discussed above for compounds having Formula I are also applicable to a compound having Formula I that is used in the first device. In particular, specific aspects of $R_1$, $R_2$, $R_3$, $R_4$, $R_5$, R', $R'_1$, $R'_2$, A, B, C, D, $L_1$, $L_2$, $L_3$, Formula II, Formula III, Formula IV, Formula V, Formula VI, Formula VII, and Compounds 1-76 of the compound having Formula I are also applicable to a compound having Formula I that is used in the first device.

In one aspect, $R_5$ is a substituted aryl. Preferably, $R_5$ is

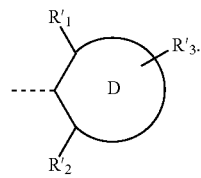

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. D is 5-membered or 6-membered carbocyclic or heterocyclic ring that is optionally further substituted with $R'_3$, which is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the organic layer is an emissive layer and the compound is an emissive dopant. In another aspect, the organic layer further comprises a host.

In one aspect, the host comprises a triphenylene containing benzo-fused thiophene or benzo-fused furan, and any substituent in the host is an unfused substituent independently selected from the group consisting of $CH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C$C_nH_{2n+1}$, $Ar_1$, $Ar_1$—$Ar_2$, $C_nH_{2n}$—$Ar_1$, or no substitution. n is from 1 to 10. $Ar_1$ and $Ar_2$ are independently selected from the group consisting of benzene, biphenyl, naphthalene, triphenylene, carbazole, and heteroaromatic analogs thereof. Preferably, the host has the formula:

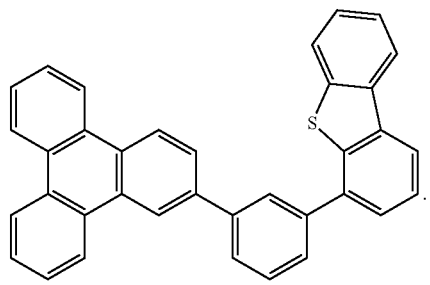 [SMILES: c1cc(-c2ccc3c4ccccc4c4ccccc4c3c2)cc(-c2cccc3c2sc2ccccc23)c1]

In another aspect, the host is selected from the group consisting of:

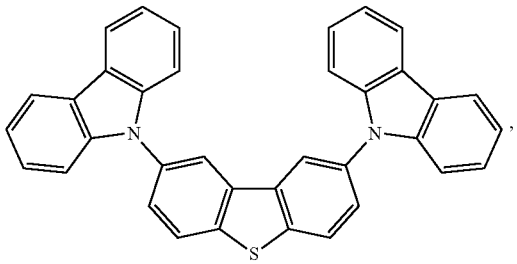

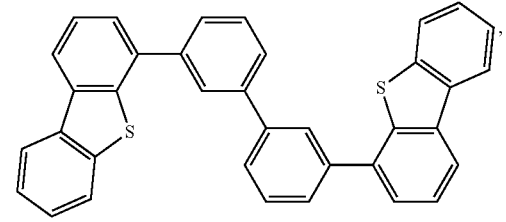

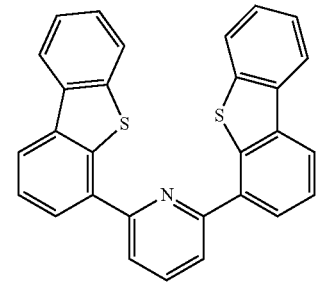

-continued

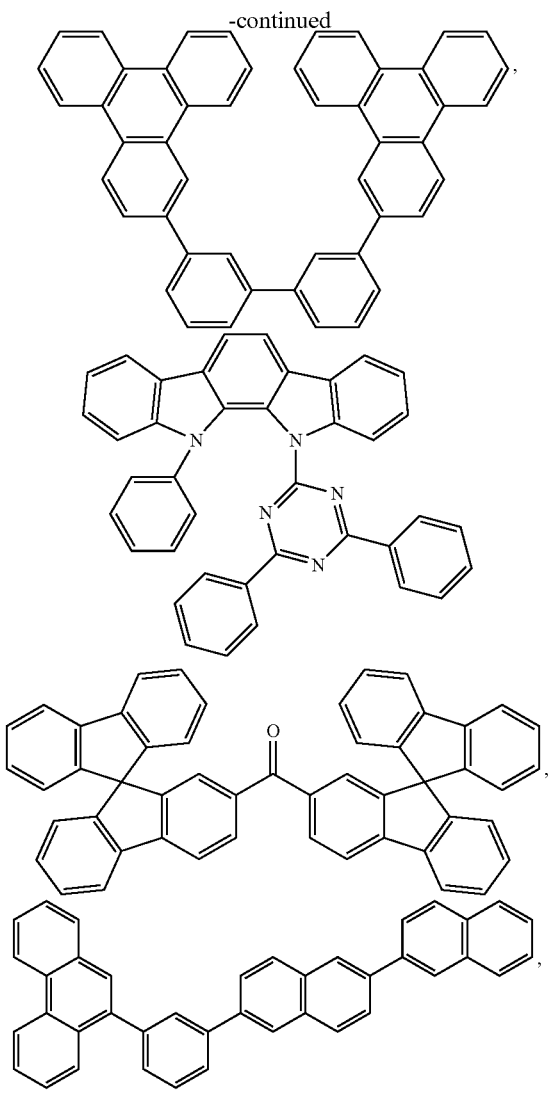

and combinations thereof.

In yet another aspect, the host is a metal complex.

In one aspect, the organic layer is an emissive layer and the compound is a non-emissive dopant.

In one aspect, the first device is a consumer product. In another aspect, the first device is an organic light-emitting device. In yet another aspect, the first device comprises a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
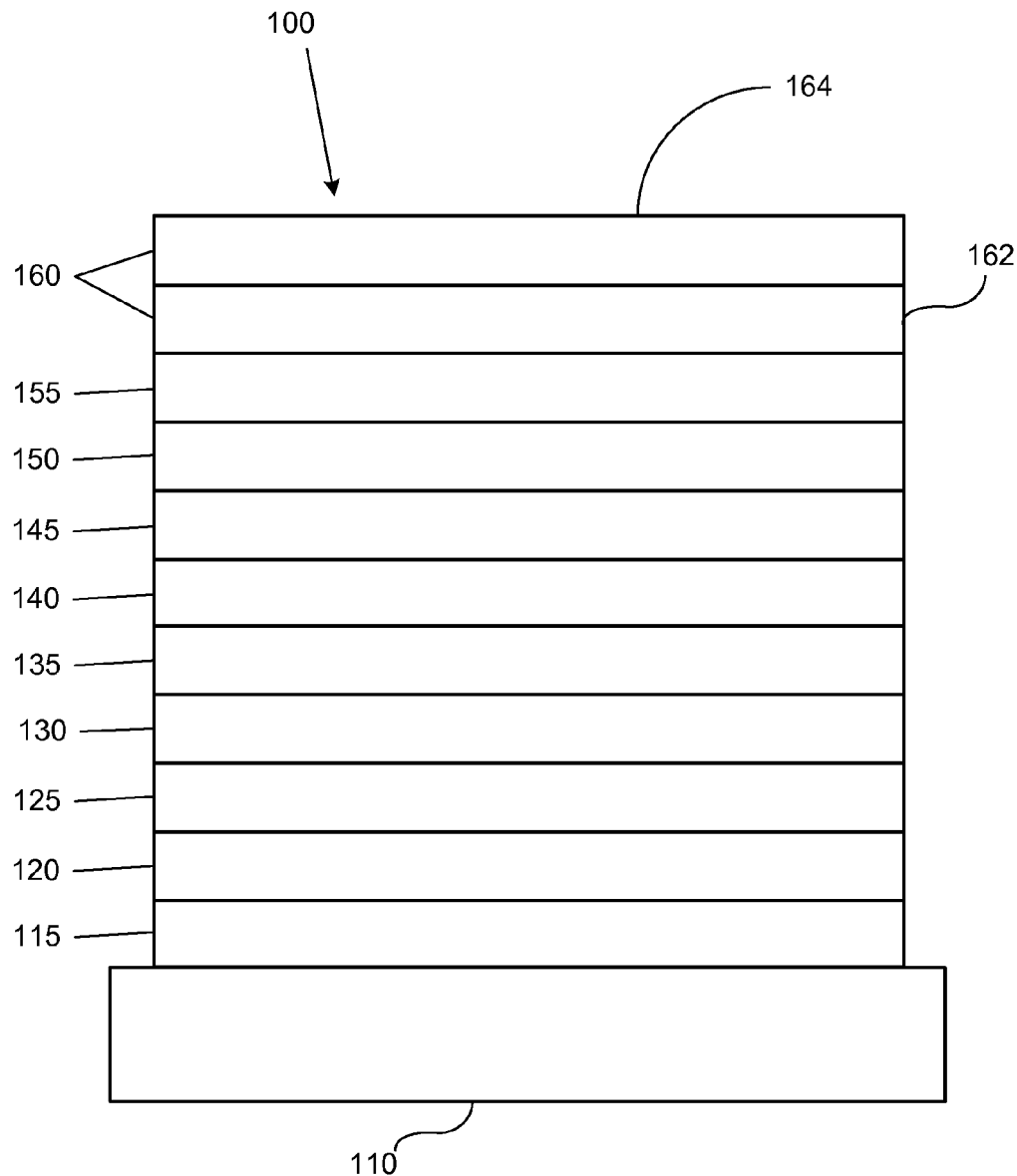
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Publication No. 2003/0230980, which are incorporated by reference in their entireties. Examples of injection layers are provided in U.S. Publication No. 2004/0174116, which is incorporated by reference in its entirety. A description of protective layers may be found in U.S. Publication No. 2004/0174116, which is incorporated by reference in its entirety.

Figure 2:
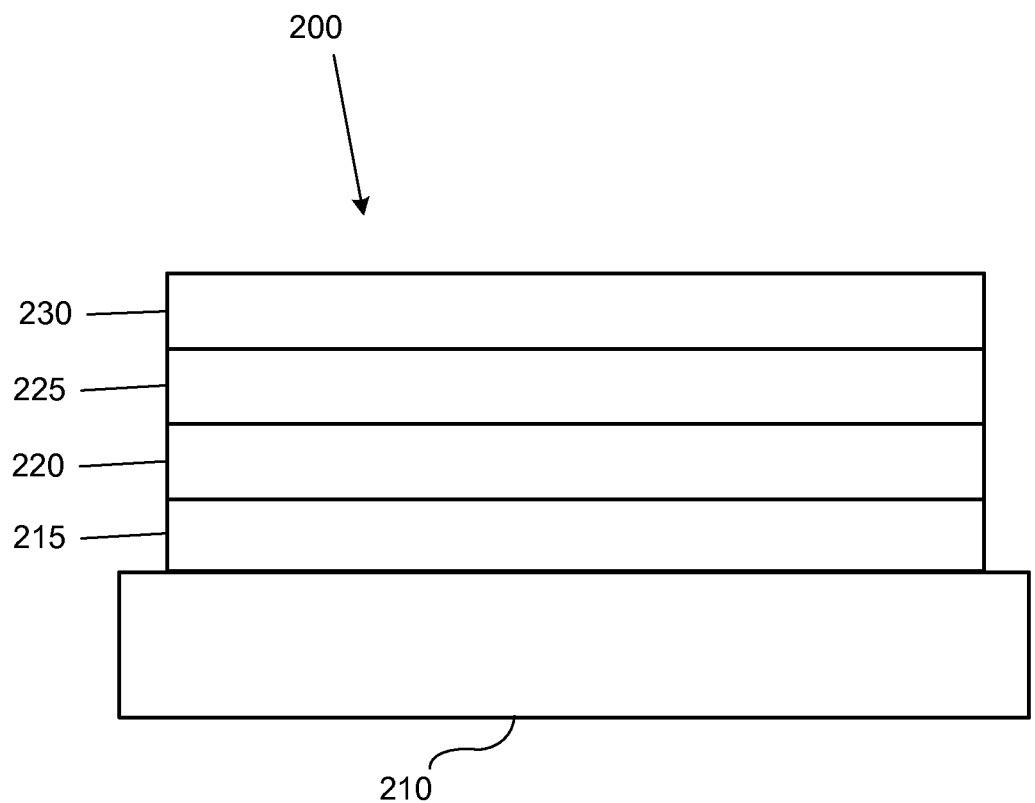
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution proccessability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
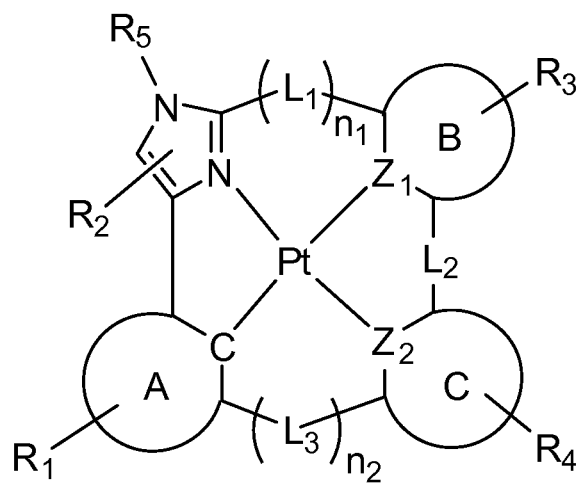
FIG. 3 shows the general structure of a tetradentate Pt(II) complex.
Figure 4:
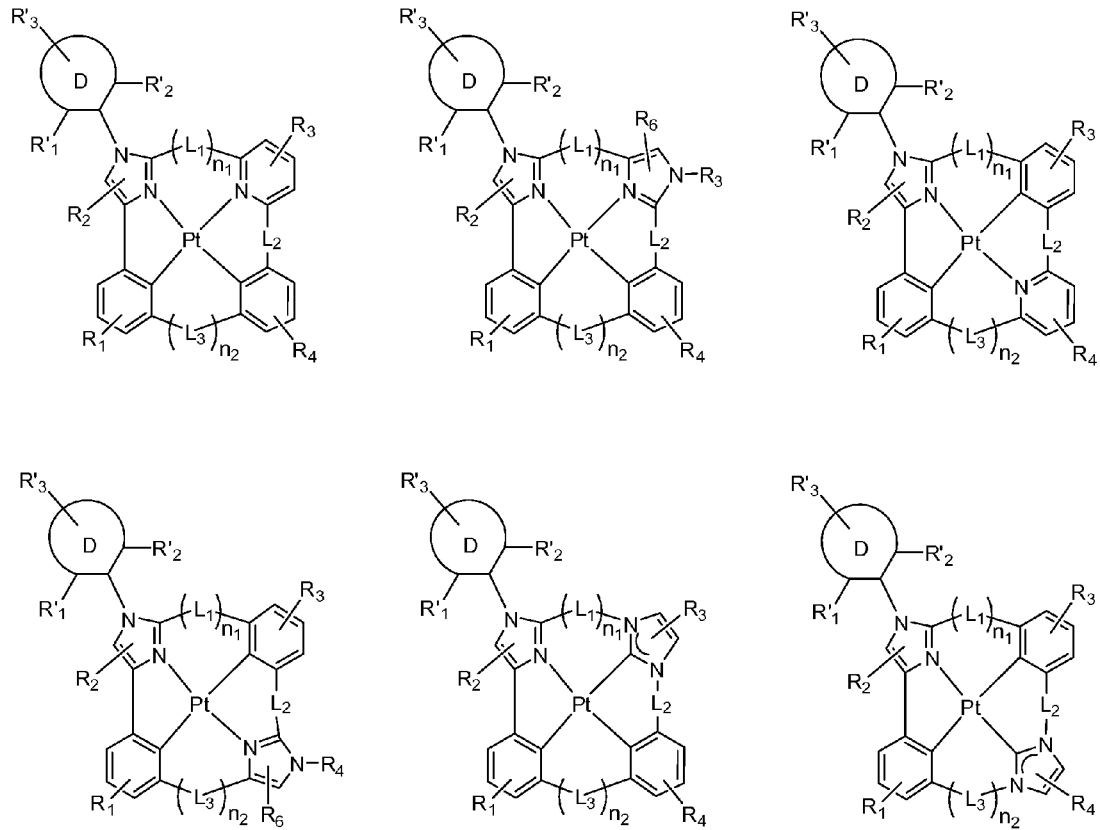
FIG. 4 shows exemplary structures of tetradentate Pt(II) complexes.

A novel class of tetradentate platinum (II) complexes are provided (as illustrated in FIG. 3). These compounds comprise an imidazole moiety and a ligand having a linkage between the carbocyclic and/or heterocyclic rings, i.e., B and C, other than a single bond. These compounds may be advantageously used in an OLED.

Although the first PHOLED demonstrated contained a platinum complex, namely 2,3,7,8,12,13,17,18-octaethyl-21H,23H-porphine platinum(II) (PtOEP), platinum complexes have not found any practical use in state-of-the-art PHOLEDs. (*Nature*, 1998, 395, 151). Compared to iridium complexes, platinum(II) complexes generally have a relatively long excited state lifetime and a lower quantum yield. In addition, platinum (II) complexes adopt a square planar geometry, which often causes excimer formation. Therefore, these complexes may have broadened emission spectrum at higher doping concentration in an OLED.

Bidentate and tridentate Pt(II) complexes have been reported, but, generally, they have limited use in OLEDs. These complexes often have poor thermal stability and device stability, thereby limiting their application in OLEDs.

Tetradentate Pt(II) complexes have also been disclosed in literature, but, similar to the bidentate and tridentate Pt(II) complexes, these tetradentate Pt(II) complexes may have limited uses in OLEDs. The novel class of tetradentate platinum (II) complexes provided herein contain a linkage between B and C other than a single bond. This linkage breaks the conjugation, and may provide a higher triplet energy. Therefore, the compounds provided herein may be advantageously used in an OLED.

Tetradentate platinum(II) complexes comprising an isoimidazole ligand are provided. The compounds have the formula:

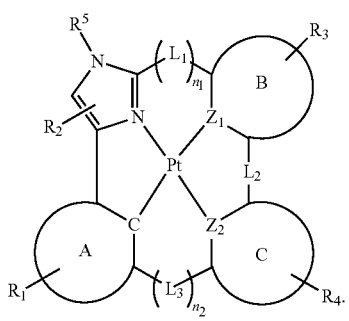

Formula I

A, B, and C are each independently a 5- or 6-membered carbocyclic or heterocyclic. $L_1$ and $L_3$ are independently selected from the group consisting of a single bond, BR, NR, PR, O, S, Se, C=O, S=O, $SO_2$, CRR', SiRR', and GeRR'. $L_2$ is selected from the group consisting of BR, NR, PR, O, S, Se, C=O, S=O, $SO_2$, CRR', SiRR', and GeRR'. $n_1$ is 0 or 1. $n_2$ is 0 or 1. $n_1+n_2$ is at least equal to 1. $Z_1$ and $Z_2$ are independently a nitrogen atom or a carbon atom. $R_1$, $R_2$, $R_3$, and $R_4$ may represent mono-, di-, tri-, or tetra-substitutions. R, R', $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R_1$ is optionally fused to A. $R_3$ is optionally fused to B. $R_4$ is optionally fused to C. $R_3$ and $R_4$ are optionally joined to form into a ring. $R_3$ and $L_2$ are optionally joined to form into a ring. $R_4$ and $L_2$ are optionally joined to form into a ring.

In one aspect, $R_5$ is a substituted aryl. Preferably, $R_5$ is a 2,6-disubstituted aryl. More preferably, $R_5$ is

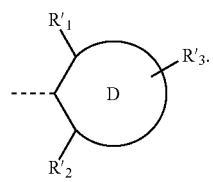

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. D is 5-membered or 6-membered carbocyclic or heterocyclic ring that is optionally further substituted with $R'_3$, which is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

Pt (II) tetradentate compounds including a twisted aryl on the N-1 of an isoimidazole are a subgenus of the compounds having Formula I. The Pt (II) tetradentate compounds comprising an isoimidazole in which the N-1 is bonded to a 2,6-disubstituted aryl ring subgenus of compounds may provide novel blue emitters that sublime and emit more efficiently in a device. By incorporating a twisted aryl moiety into the tetradentate architecture, the Pt(II) complexes may demonstrate higher efficiency and longer device lifetimes. Without being bound by theory, it is believed that twisting the aryl group out of the plane of the isoimidazole ring, thus breaking the conjugation, may result in several advantages. The compounds may provide a bluer color. Furthermore, the compounds may have improved sublimation and improved efficiency because the compound with a twisted aryl is much less planar than a compound without the twisted aryl. Specifically, the compounds may be less prone to triplet-triplet annihilation and self-quenching, because they have more three-dimensional character. Several tetradentate platinum complexes bearing a twisted aryl on N-1 of an isoimidazole are disclosed herein, including Compounds 1-64, 69, 70 and 72-76.

In one aspect, each of $R'_1$ and $R'_2$ is not hydrogen or deuterium. In another aspect, at least one of $R'_1$ and $R'_2$ is an alkyl. In yet another aspect, each of $R'_1$ and $R'_2$ is an alkyl. In a further aspect, at least one of $R'_1$ and $R'_2$ is an alkyl containing at least 2 carbons. In another aspect, at least one of $R'_1$ and $R'_2$ is an aryl. In yet another aspect, each of $R'_1$ and $R'_2$ is an aryl.

In one aspect, the compound has a neutral charge. In another aspect, two of A, B, and C are phenyl and one of A, B, and C is pyridine.

In one aspect, the compound has the formula:

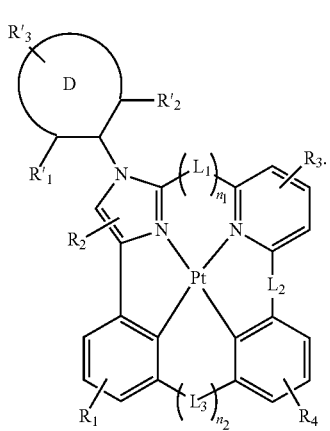

Formula II

In another aspect, the compound has the formula:

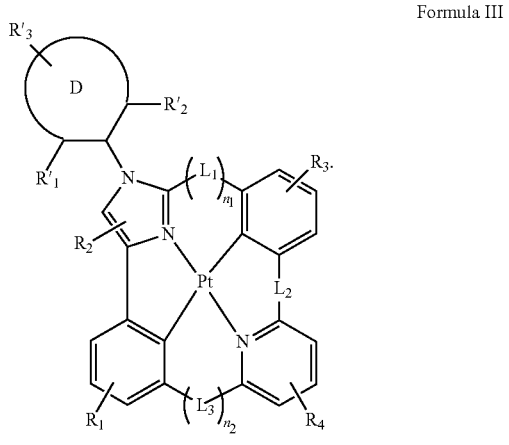

Formula III

In yet another aspect, the compound has the formula:

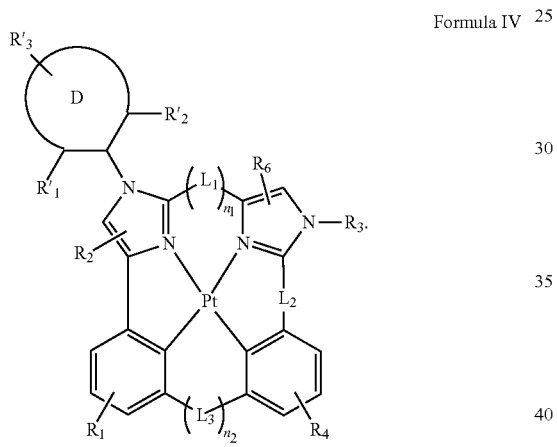

Formula IV

In a further aspect, the compound has the formula:

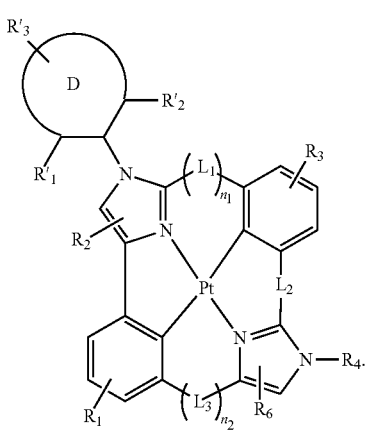

Formula V

In another aspect, the compound has the formula:

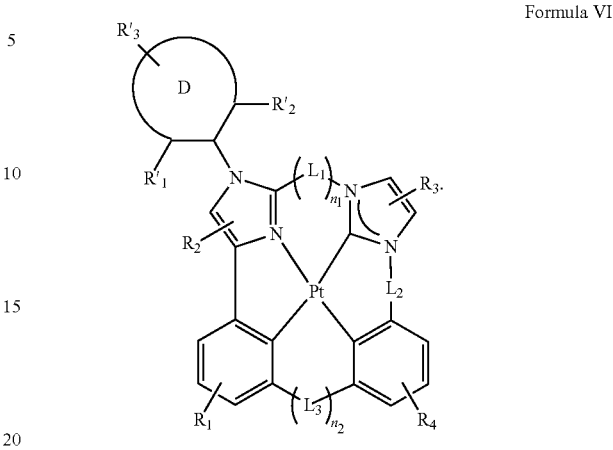

Formula VI

In yet another aspect, the compound has the formula:

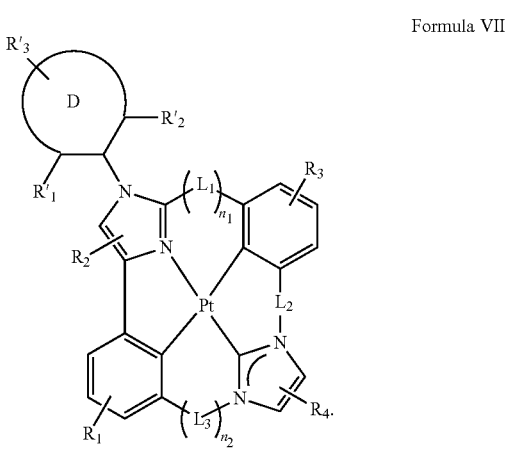

Formula VII

Formulas II-VII show a preferred subset of structures for compound having Formula I. A, i.e., the A ring, in these structures is phenyl, which is known to form a strong carbon metal bond with desirable photophysical properties based on the C^isoimidazole cyclometallating ligand. The properties of the complex may be further tuned by substituting B and C, i.e., the B and C rings, with phenyl or a nitrogen heterocycle. The preferred nitrogen heterocycle includes imidazole, bound through the nitrogen or a neutrally coordinated carbene and pyridine. Without being bound by theory, it is believed that the $L_2$ bridging group breaks the conjugation between the B and C rings, thereby allowing for the photophysics to be governed primarily by the phenyl-isoimidazole cyclometallating ligand.

In one aspect, $L_1$ or $L_3$ is selected from the group consisting of O, S, $CH_2$, $CR'_2$, NR', $SiR'_2$ or BR'. R' is alkyl or aryl. In another aspect, $L_2$ is selected from the group consisting of O, S, $CH_2$, $CR'_2$, NR', and $SiR'_2$. R' is alkyl or aryl, and R' is optionally bonded to B or C.

In one aspect, $R_1$, $R_2$, $R_3$ and $R_4$ are each independently selected from the group consisting of hydrogen, deuterium, alkyl, aryl, cyclic alkyl, branched alkyl, heteroaryl, and fused aryl.

Specific, non-limiting examples of the tetradentate platinum (II) complex are provided. In one aspect, the compound is selected from the group consisting of:
Compound 1
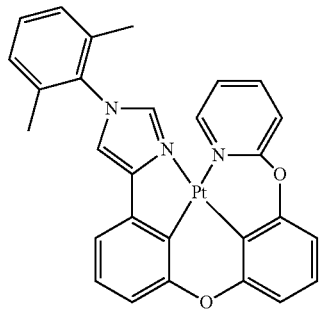
Compound 2
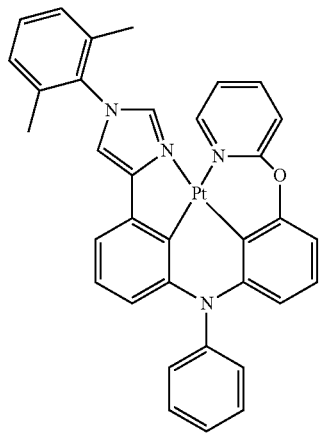
Compound 3
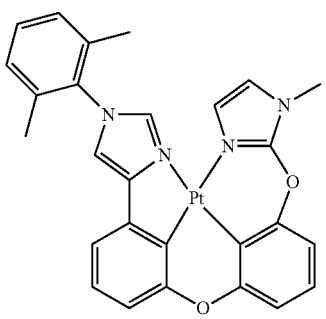
Compound 4
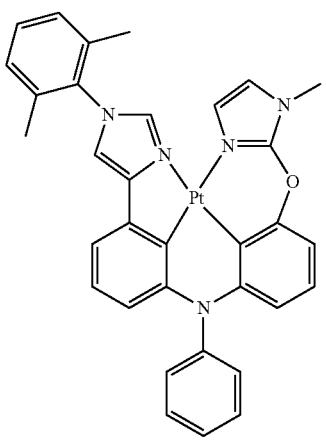
Compound 5
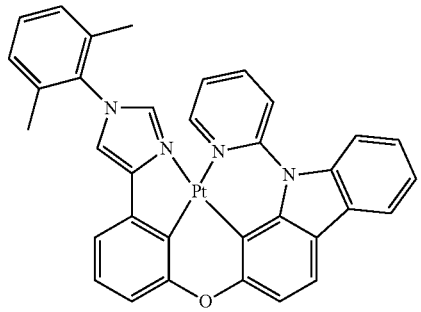
Compound 6
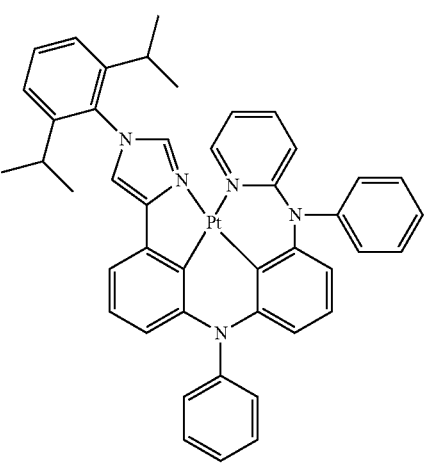
Compound 7
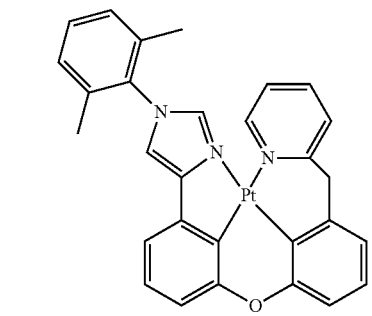
Compound 8
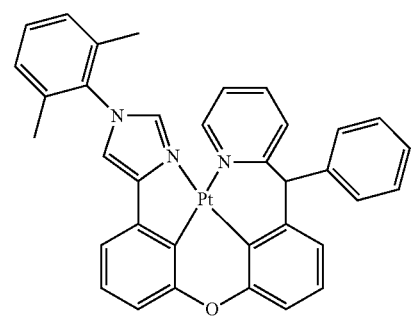

-continued
Compound 9
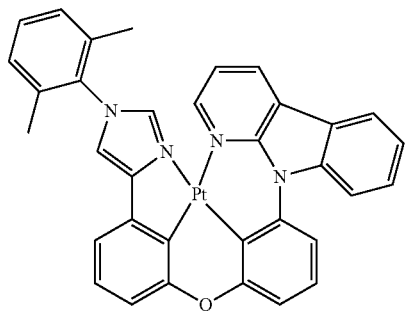
Compound 10
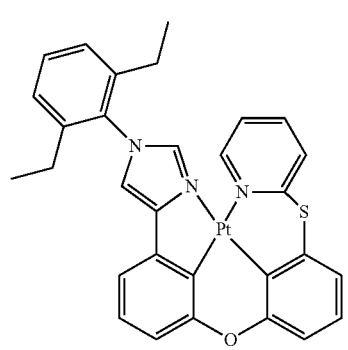
Compound 11
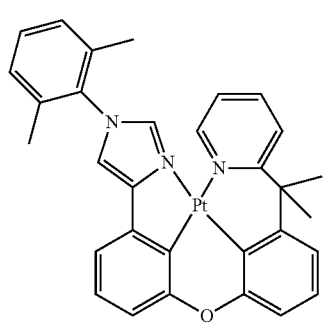
Compound 12
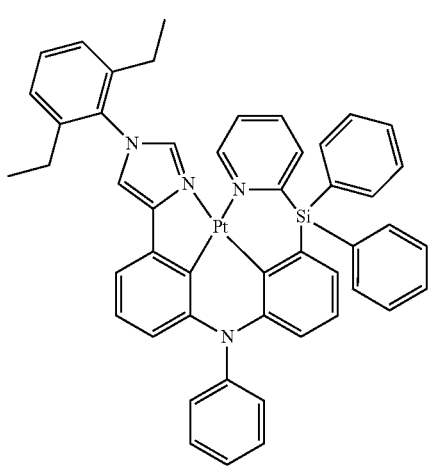
Compound 13
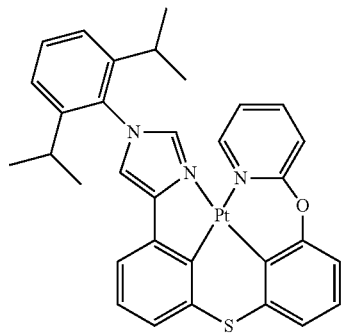
Compound 14
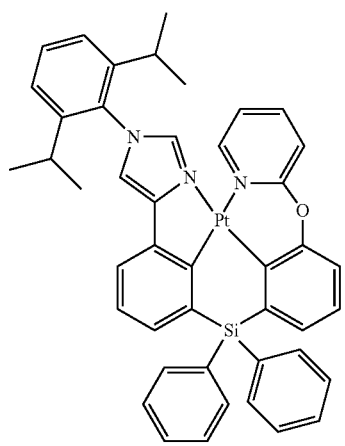
Compound 15
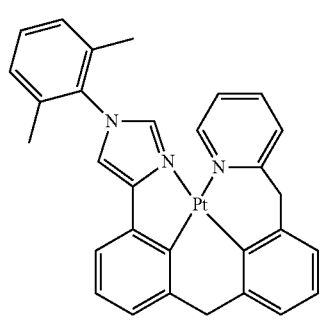
Compound 16
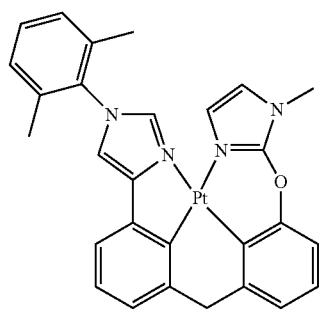

Compound 17
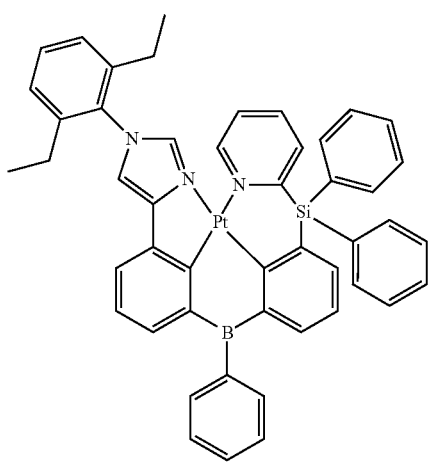
Compound 18
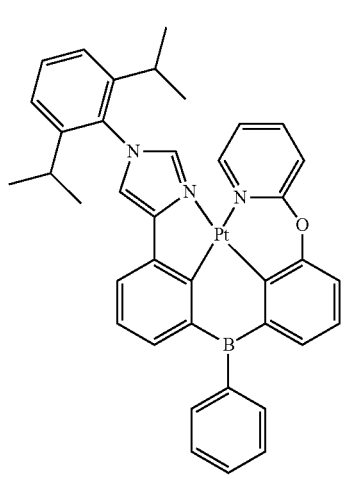
Compound 19
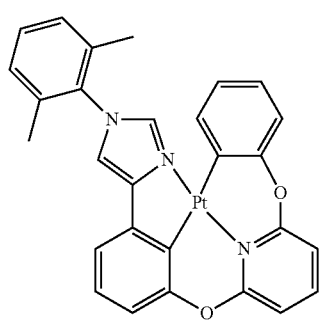
Compound 20
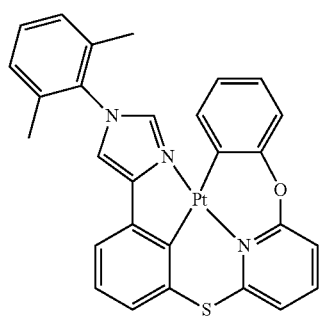
Compound 21
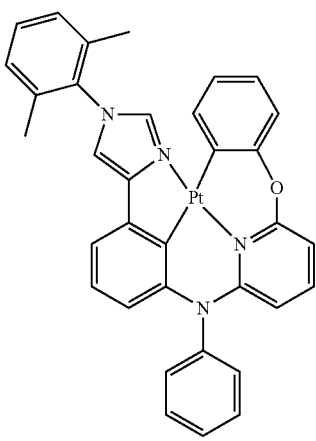
Compound 22
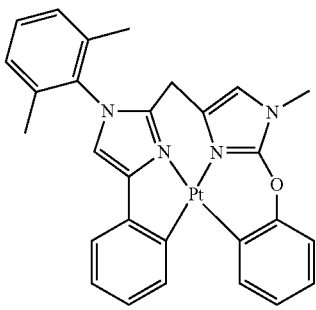
Compound 23
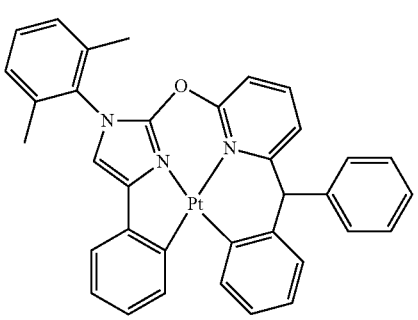
Compound 24
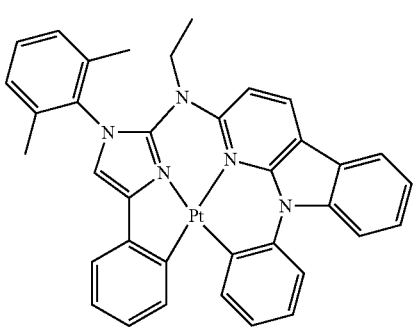

-continued
Compound 25
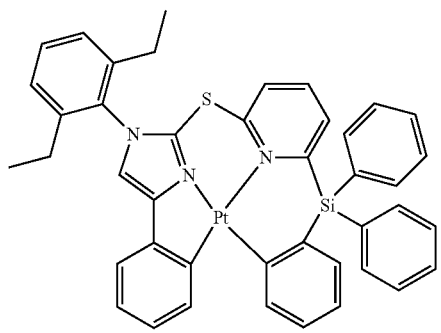
Compound 26
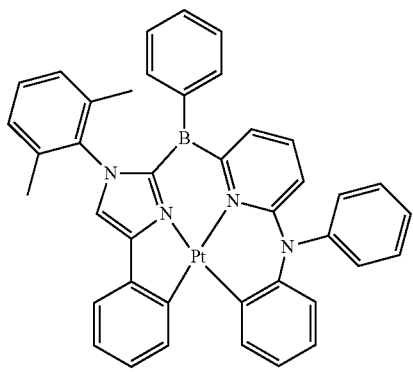
Compound 27
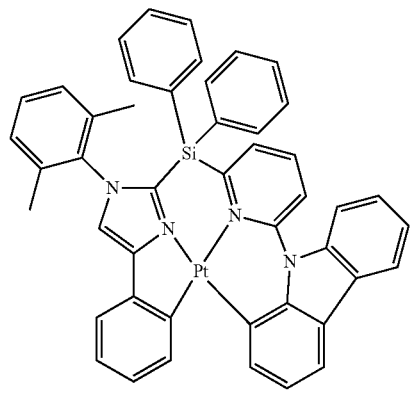
Compound 28
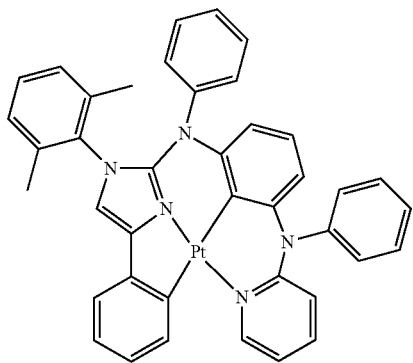
Compound 29
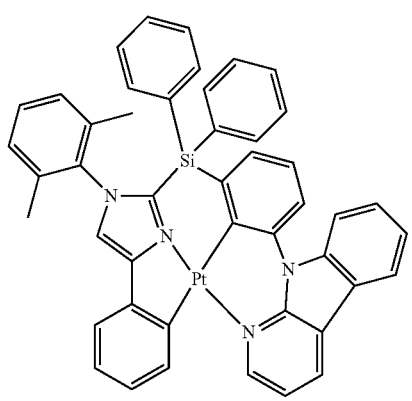
Compound 30
Compound 31
Compound 32

Compound 33
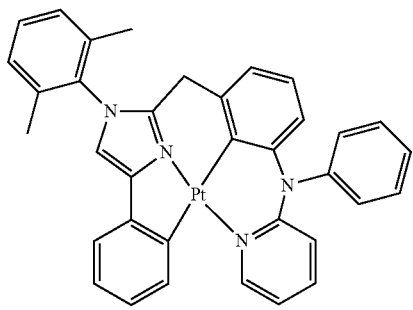
Compound 34
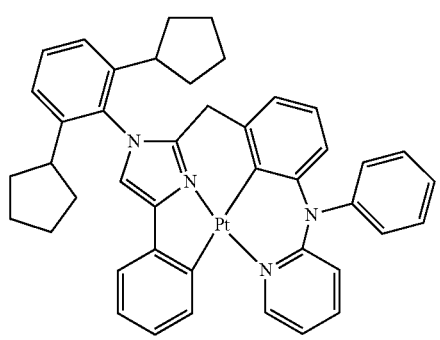
Compound 35
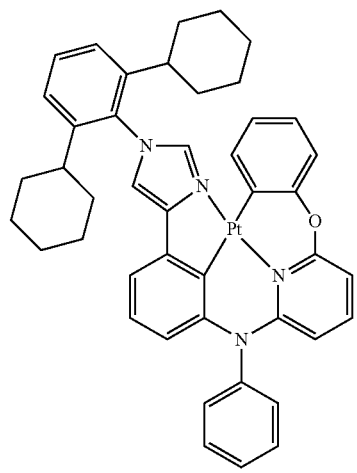
Compound 36
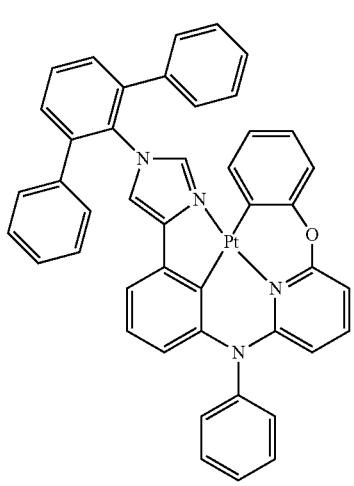
Compound 37
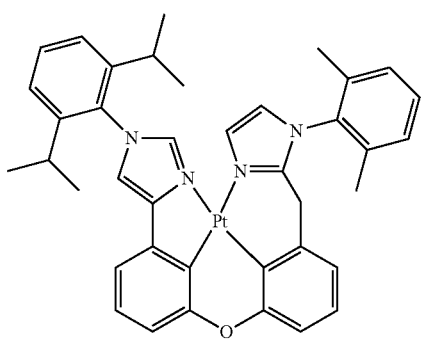
Compound 38
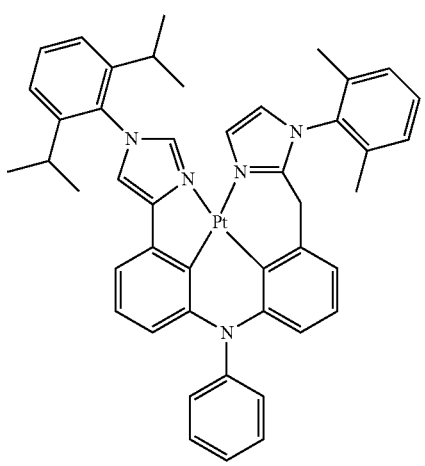
Compound 39
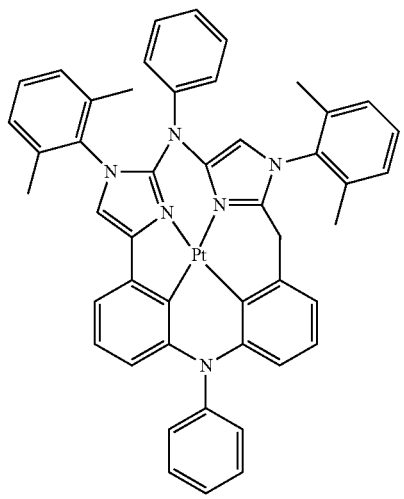

Compound 40
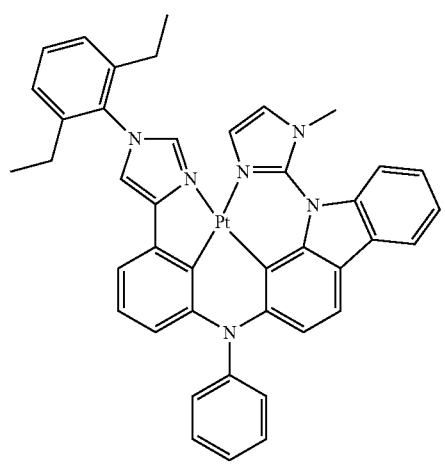
Compound 41
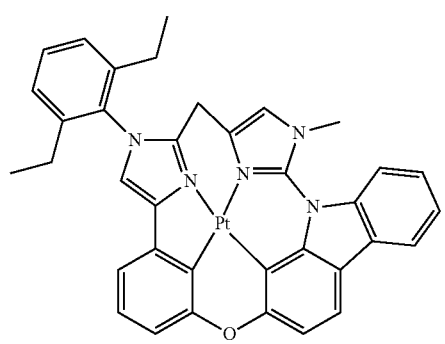
Compound 42
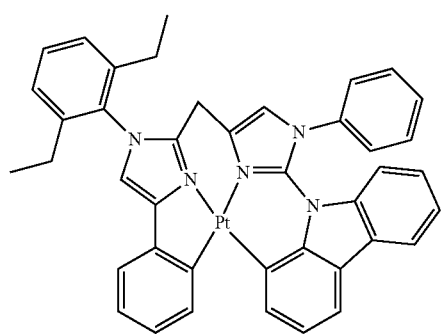
Compound 43
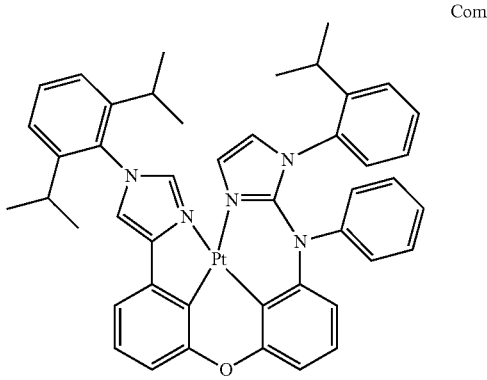
Compound 44
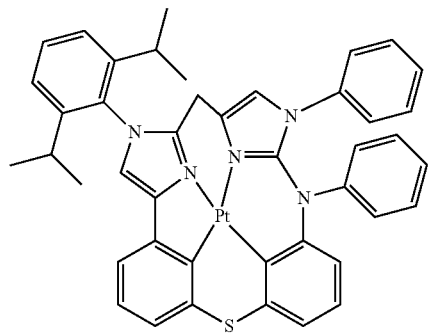
Compound 45
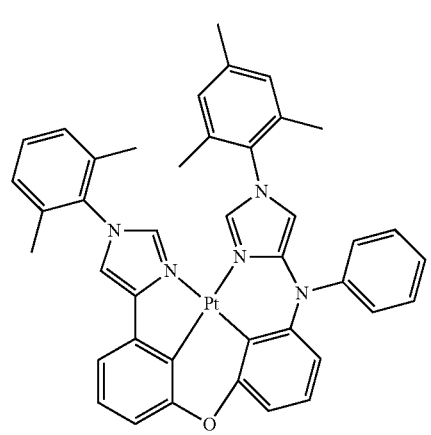
Compound 46
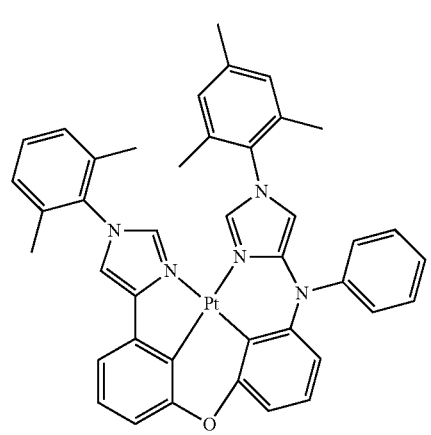
Compound 47
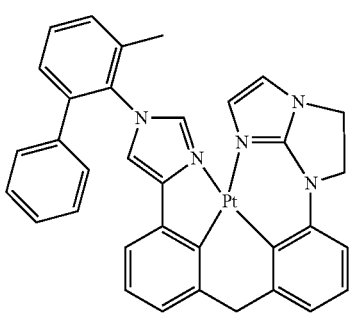

Compound 48
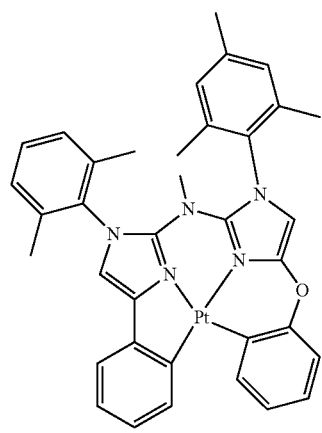
Compound 51
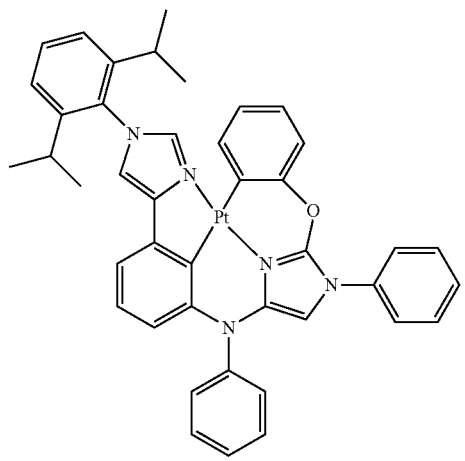
Compound 49
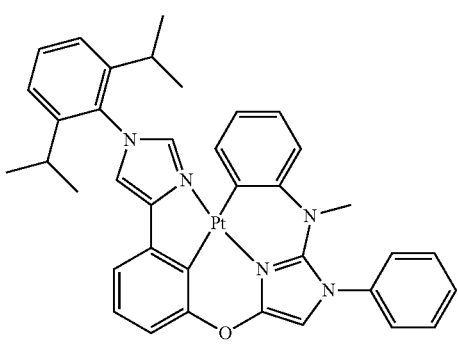
Compound 52
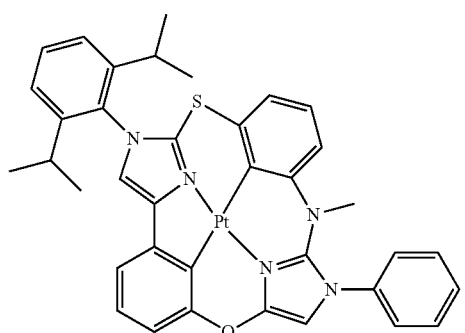
Compound 53
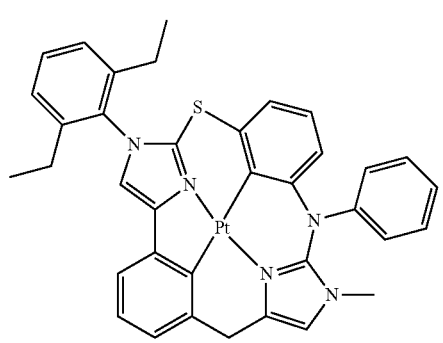
Compound 50
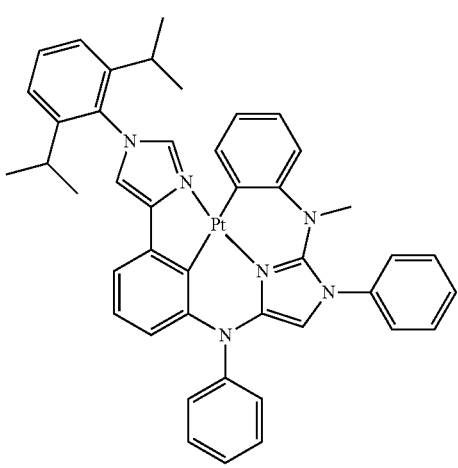
Compound 54
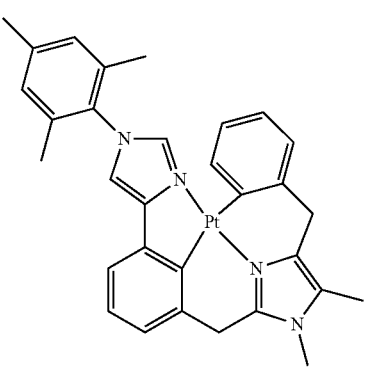

Compound 55
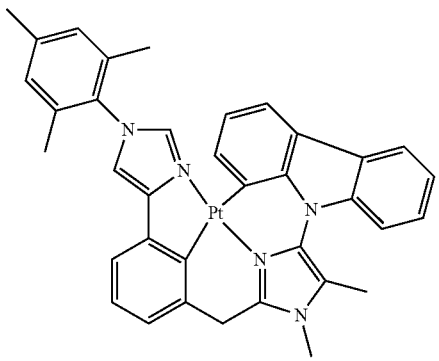
Compound 56
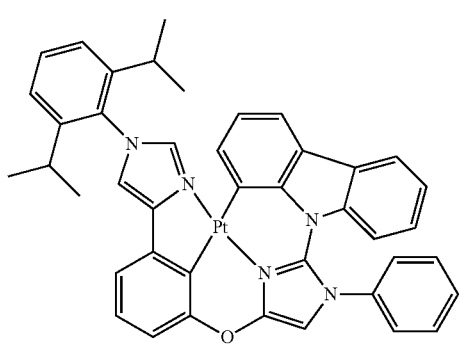
Compound 57
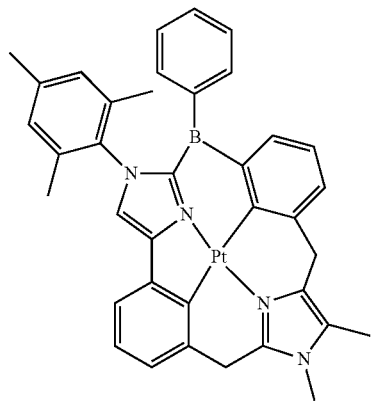
Compound 58
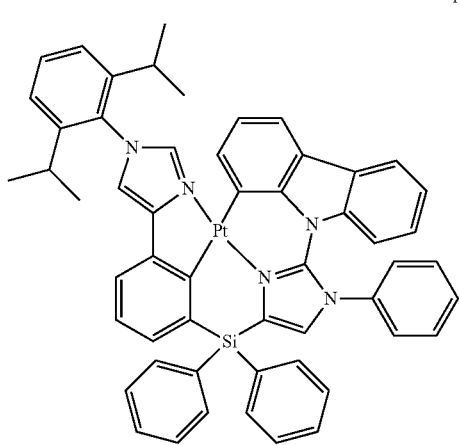
Compound 59
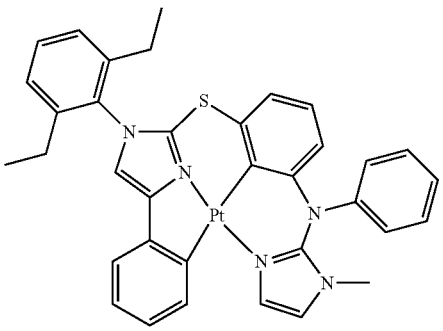
Compound 60
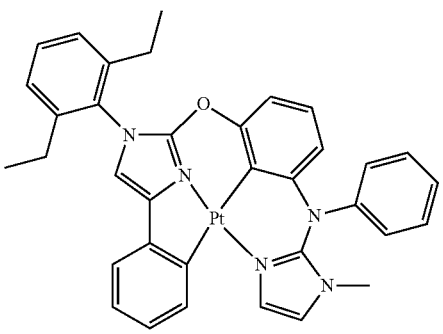
Compound 61
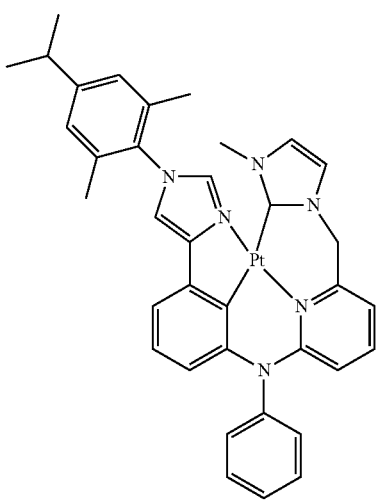

Compound 62
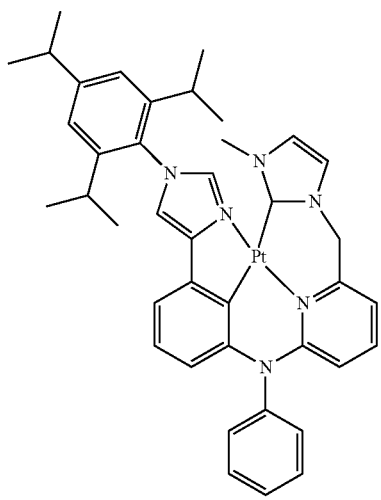
Compound 63
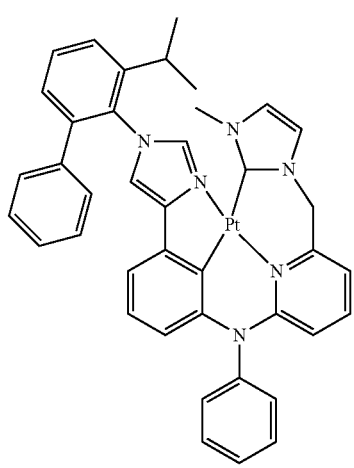
Compound 64
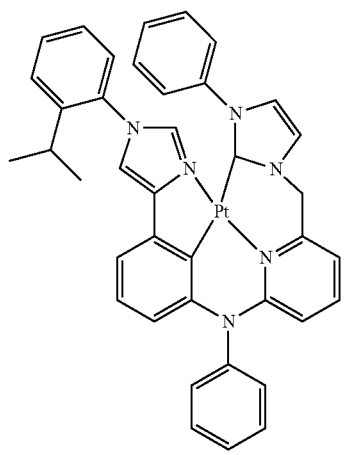
Compound 65
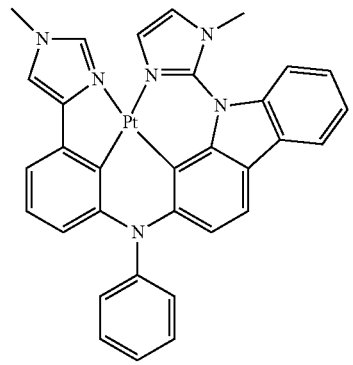
Compound 66
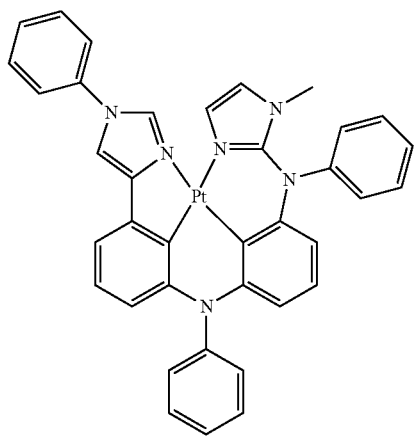
Compound 67
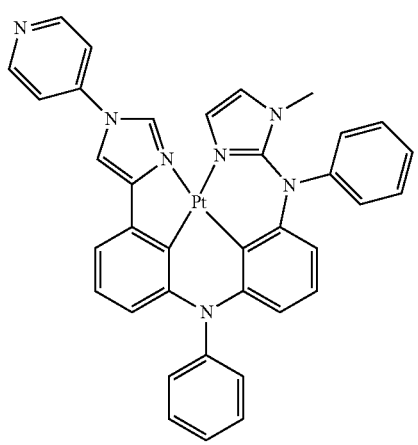
Compound 68
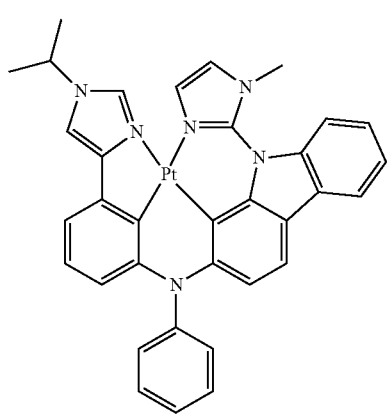

Compound 69
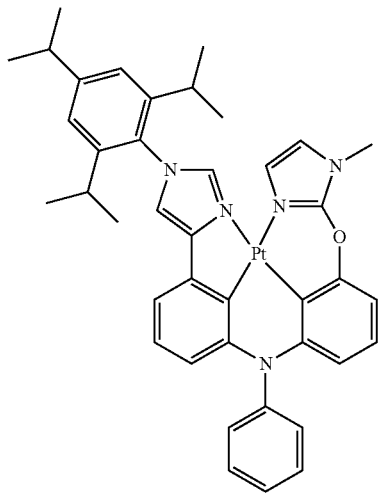
Compound 70
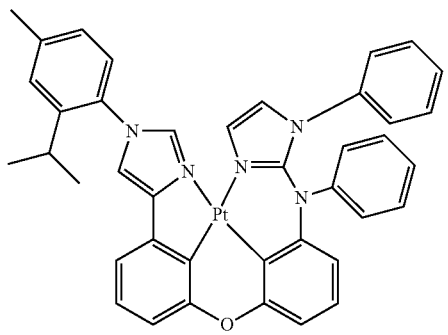
Compound 71
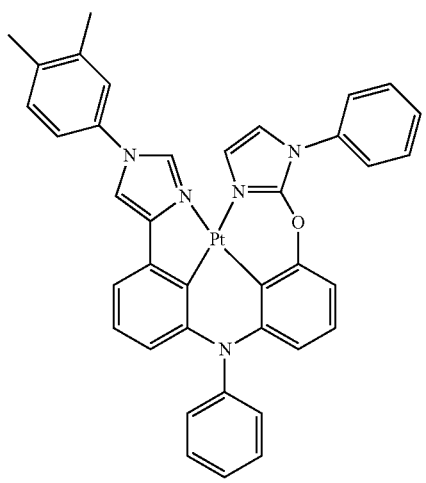
Compound 72
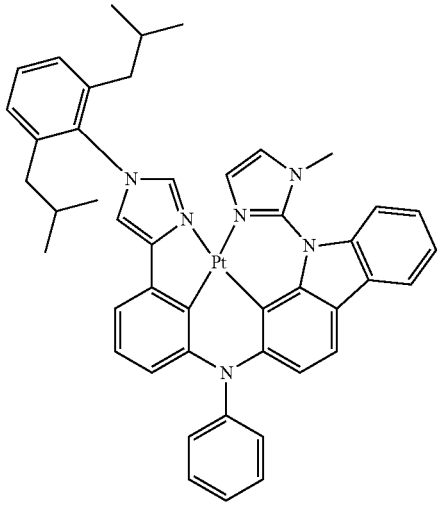
Compound 73
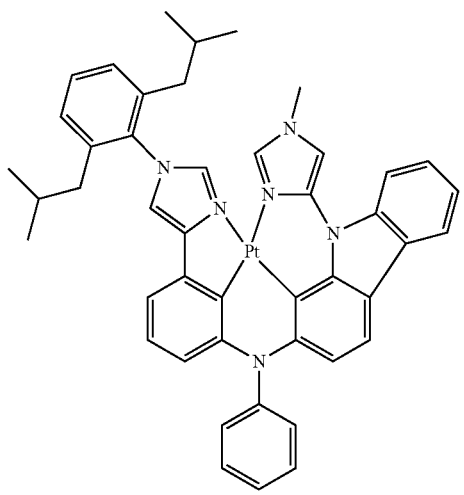
Compound 74
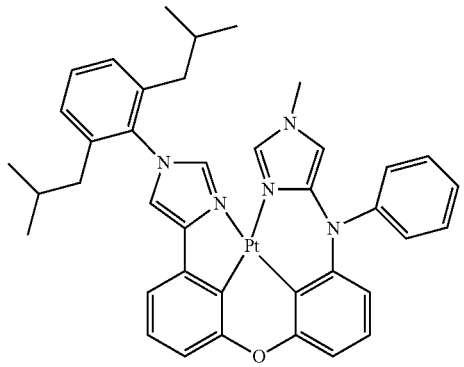

Compound 75

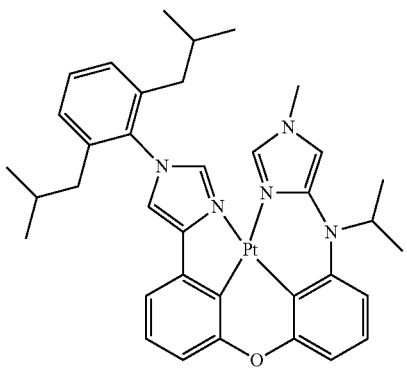

Compound 76

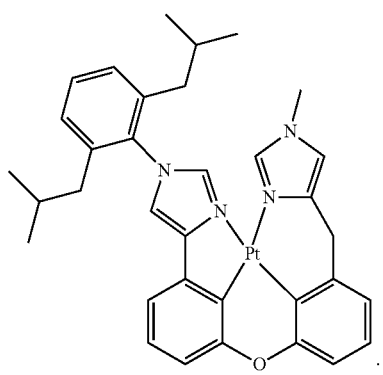

Additionally, a first device is provided. The first device comprises a first organic light emitting device. The organic light emitting device further comprises an anode, a cathode, and an organic layer, disposed between the anode and the cathode. The organic layer comprises a compound having the formula:

Formula I

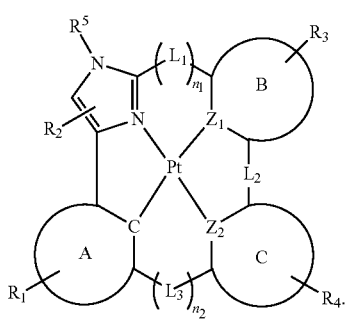

A, B, and C are each independently a 5- or 6-membered carbocyclic or heterocyclic ring. $L_1$ and $L_3$ are independently selected from the group consisting of a single bond, BR, NR, PR, O, S, Se, C=O, S=O, $SO_2$, CRR', SiRR', and GeRR'. $L_2$ is selected from the group consisting of BR, NR, PR, O, S, Se, C=O, S=O, $SO_2$, CRR', SiRR', and GeRR'. $n_1$ is 0 or 1. $n_2$ is 0 or 1. $n_1+n_2$ is at least equal to 1. $Z_1$ and $Z_2$ are independently a nitrogen atom or a carbon atom. $R_1$, $R_2$, $R_3$, and $R_4$ may represent mono-, di-, tri-, or tetra-substitutions. R, R', $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R_1$ is optionally fused to A. $R_3$ is optionally fused to B. $R_4$ is optionally fused to C. $R_3$ and $R_4$ are optionally joined to form into a ring. $R_3$ and $L_2$ are optionally joined to form into a ring. $R_4$ and $L_2$ are optionally joined to form into a ring.

The various specific aspects discussed above for compounds having Formula I are also applicable to a compound having Formula I that is used in the first device. In particular, specific aspects of $R_1$, $R_2$, $R_3$, $R_4$, $R_5$, R', $R'_1$, $R'_2$, A, B, C, D, $L_1$, $L_2$, $L_3$, Formula II, Formula III, Formula IV, Formula V, Formula VI, Formula VII, and Compounds 1-76 of the compound having Formula I are also applicable to a compound having Formula I that is used in the first device.

In one aspect, $R_5$ is a substituted aryl. Preferably, $R_5$ is

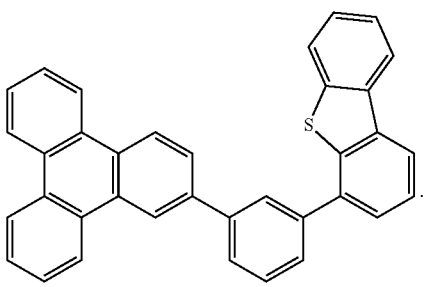 [SMILES: c1cc(-c2ccc3c4ccccc4c4ccccc4c3c2)cc(-c2cccc3c2sc2ccccc23)c1]

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. D is 5-membered or 6-membered carbocyclic or heterocyclic ring that is optionally further substituted with $R'_3$, which is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the organic layer is an emissive layer and the compound is an emissive dopant. In another aspect, the organic layer further comprises a host.

In one aspect, the host comprises a triphenylene containing benzo-fused thiophene or benzo-fused furan, and any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C$C_nH_{2n+1}$, $Ar_1$, $Ar_1$—$Ar_2$, $C_nH_{2n}$—$Ar_1$, or no substitution. n is from 1 to 10. $Ar_1$ and $Ar_2$ are independently selected from the group consisting of benzene, biphenyl, naphthalene, triphenylene, carbazole, and heteroaromatic analogs thereof. Preferably, the host has the formula:

In another aspect, the host is selected from the group consisting of:

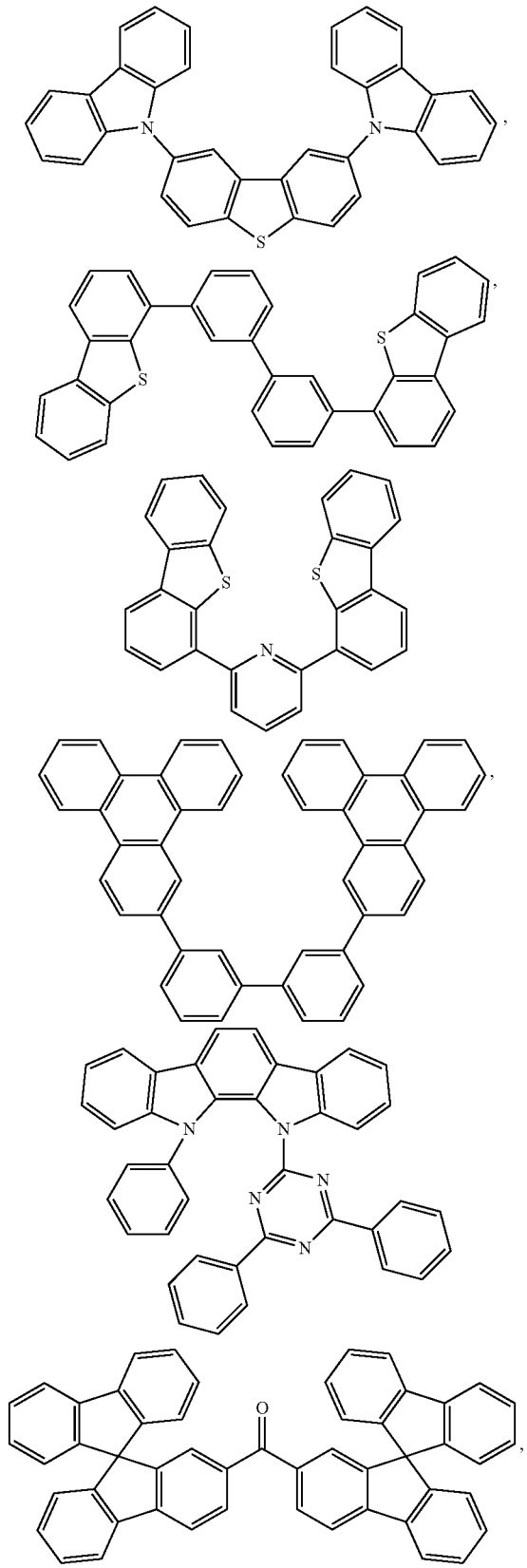

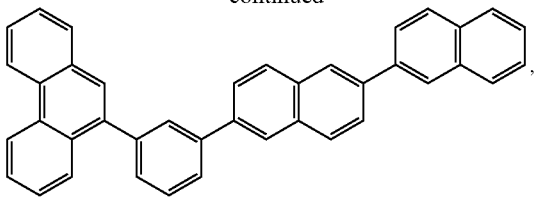

and combinations thereof.

In yet another aspect, the host is a metal complex.

In one aspect, the organic layer is an emissive layer and the compound is a non-emissive dopant.

In one aspect, the first device is a consumer product. In another aspect, the first device is an organic light-emitting device. In yet another aspect, the first device comprises a lighting panel.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

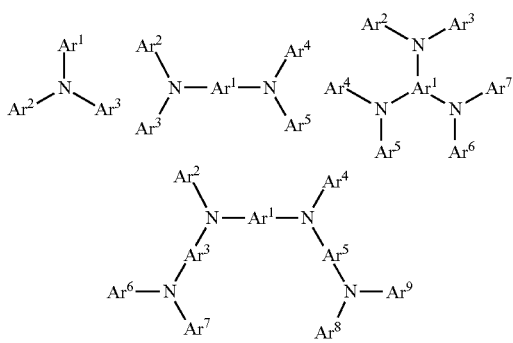

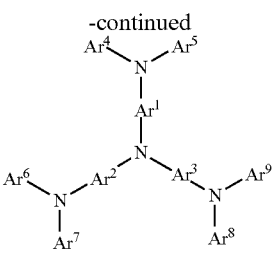

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

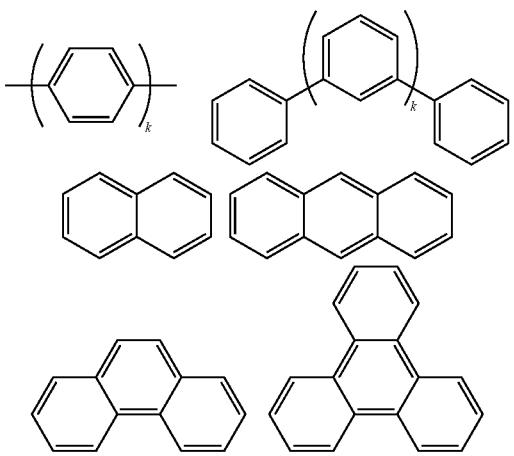

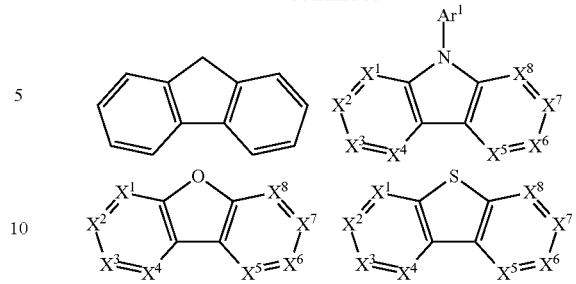

k is an integer from 1 to 20; $X^1$ to $X^8$ is C (including CH) or N; $Ar^1$ has the same group defined above.

Examples of metal complexes used in HIL or HTL include, but not limit to the following general formula:

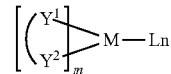

M is a metal, having an atomic weight greater than 40; ($Y^1$—$Y^2$) is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$—$Y^2$) is a 2-phenylpyridine derivative.

In another aspect, ($Y^1$—$Y^2$) is a carbene ligand.

In another aspect, M is selected from Ir, Pt, Os, and Zn.

In a further aspect, the metal complex has a smallest oxidation potential in solution vs. $Fc^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

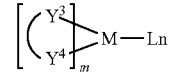

M is a metal; ($Y^3$—$Y^4$) is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

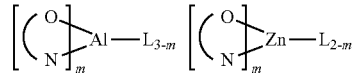

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

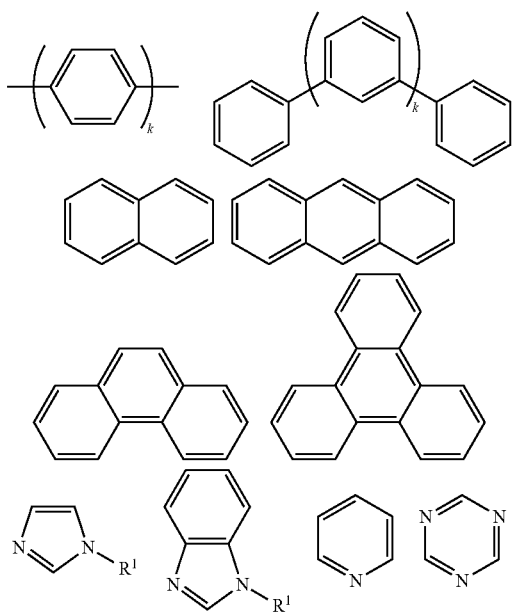

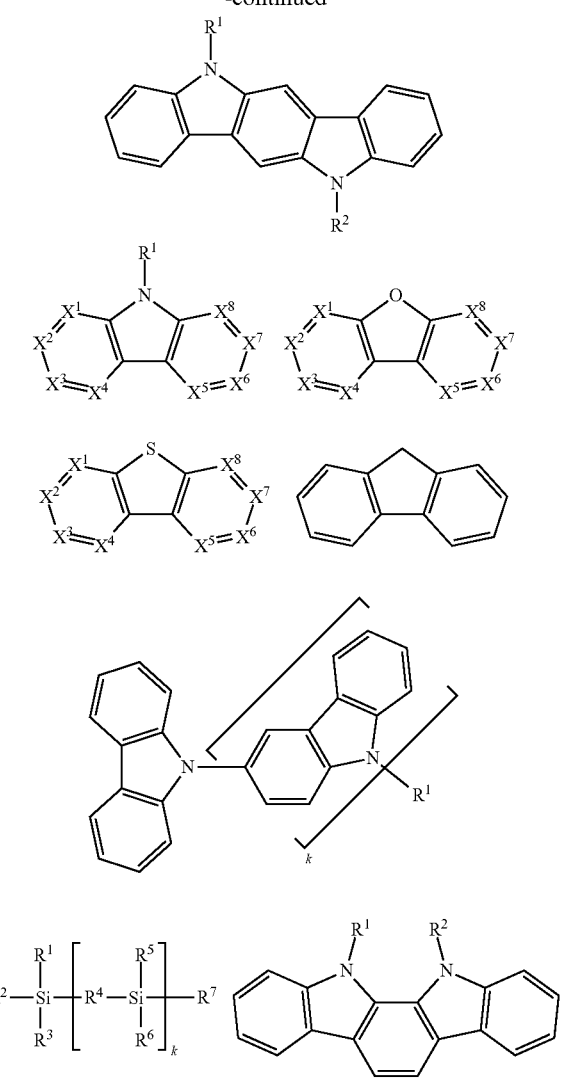

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

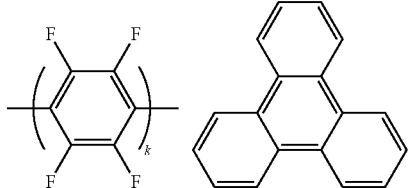

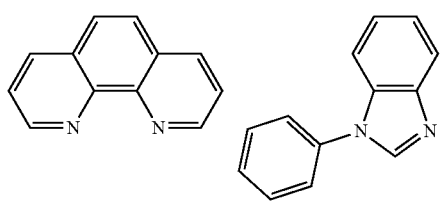

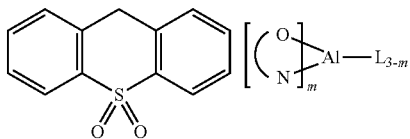

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

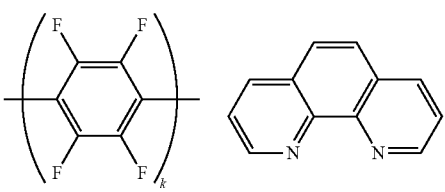

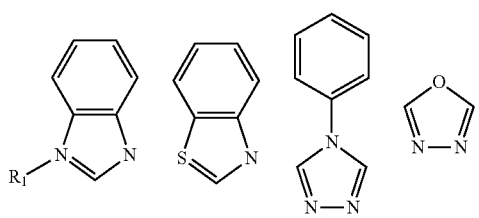

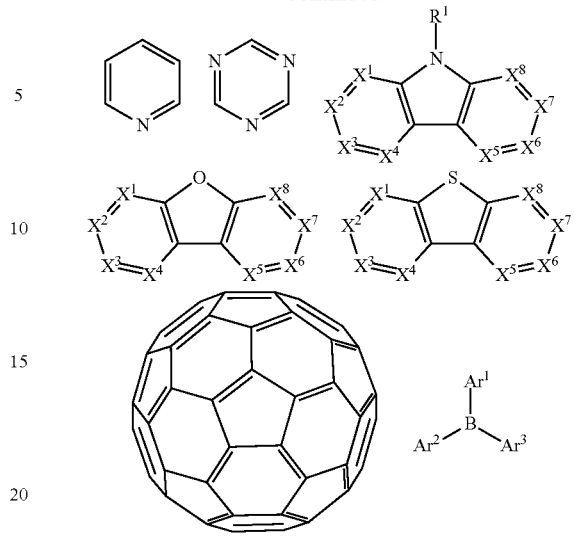

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

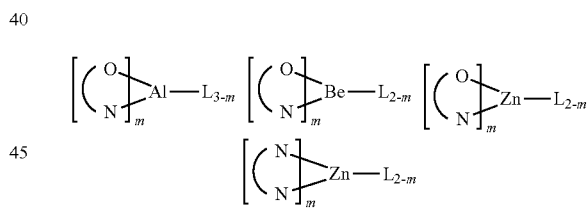

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1
| MATERIAL | EXAMPLES OF MATERIAL | PUBLICATIONS |
|---|---|---|
| Hole injection materials | | |
| Phthalocyanine and porphryin compounds | 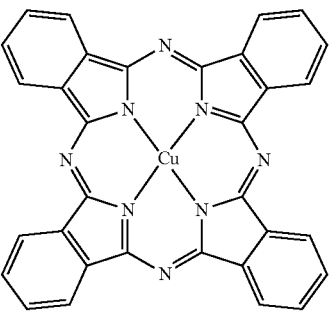 | Appl. Phys. Lett. 69, 2160 (1996) |
| Starburst triarylamines | 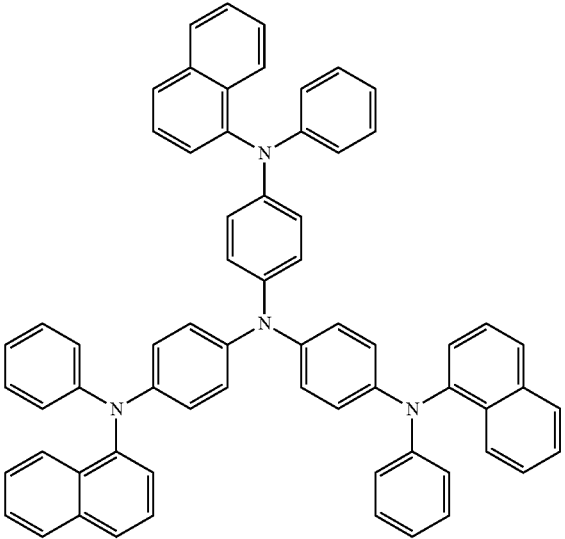 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluoro-hydrocarbon polymer | $-[CH_xF_y]_n-$ | Appl. Phys. Lett. 78, 673 (2001) |
| Conducting polymers (e.g., PEDOT:PSS, polyaniline, polypthiophene) | 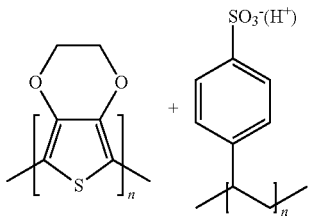 | Synth. Met. 87, 171 (1997) WO2007002683 |
| Phosphonic acid and sliane SMAs | 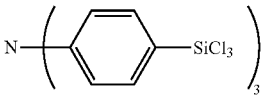 | US20030162053 |

TABLE 1-continued
| MATERIAL | EXAMPLES OF MATERIAL | PUBLICATIONS |
|---|---|---|
| Triarylamine or polythiophene polymers with conductivity dopants | 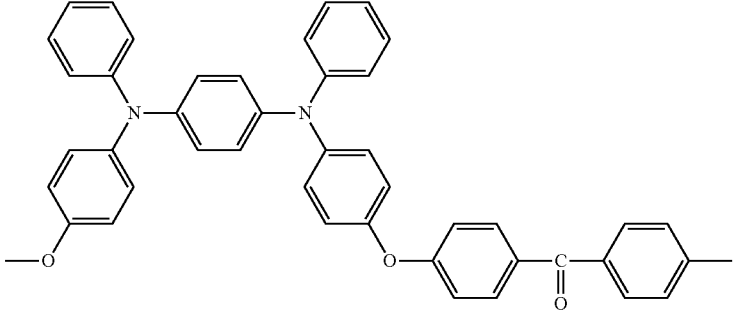 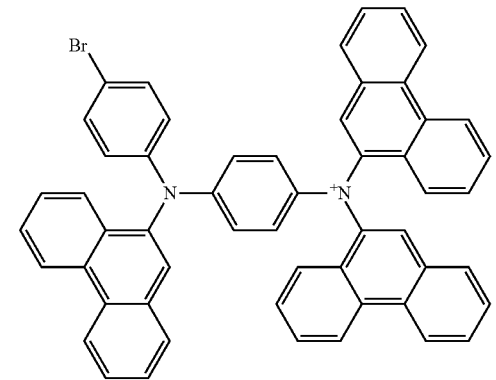 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 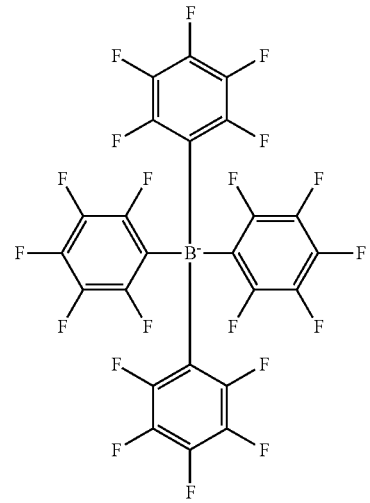 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Arylamines complexed with metal oxides such as molybdenum and tungsten oxides | 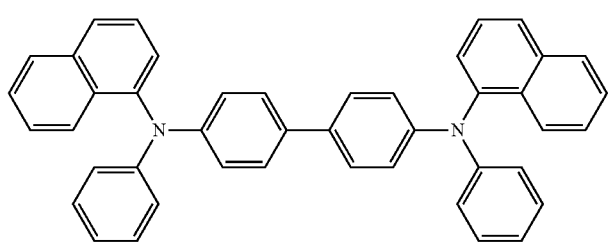 | SID Symposium Digest, 37, 923 (2006) WO2009018009 |

TABLE 1-continued
| MATERIAL | EXAMPLES OF MATERIAL | PUBLICATIONS |
|---|---|---|
| p-type semi-conducting organic complexes | 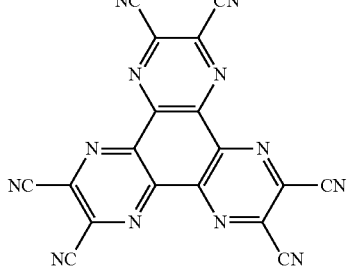 | US20020158242 |
| Metal organometallic complexes | 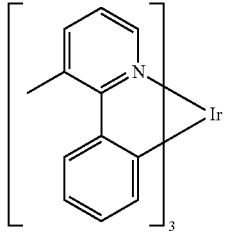 | US20060240279 |
| Cross-linkable compounds | 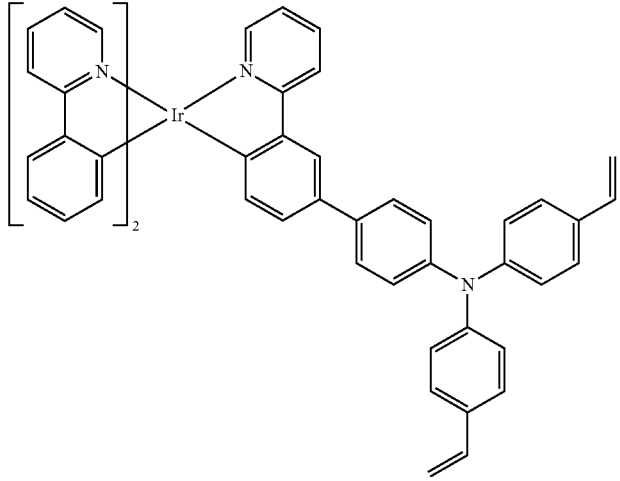 | US20080220265 |
| Hole transporting materials | | |
| Triarylamines (e.g., TPD, α-NPD) | 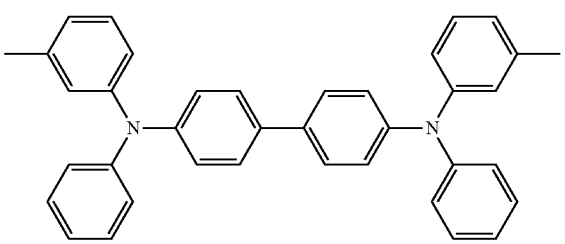 | Appl. Phys. Lett. 51, 913 (1987) |
| | 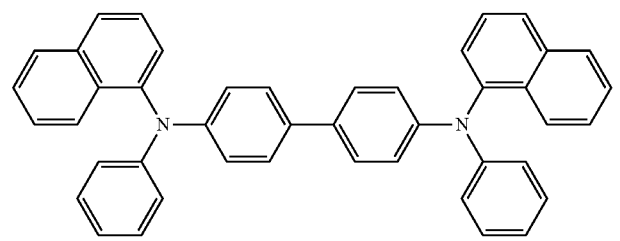 [SMILES: c1ccc(N(c2ccc(-c3ccc(N(c4ccccc4)c4cccc5ccccc45)cc3)cc2)c2cccc3ccccc23)cc1] | US5061569 |

TABLE 1-continued
| MATERIAL | EXAMPLES OF MATERIAL | PUBLICATIONS |
|---|---|---|
| | 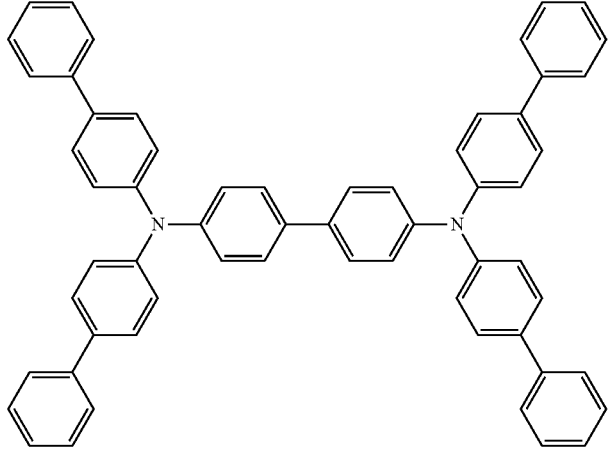 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 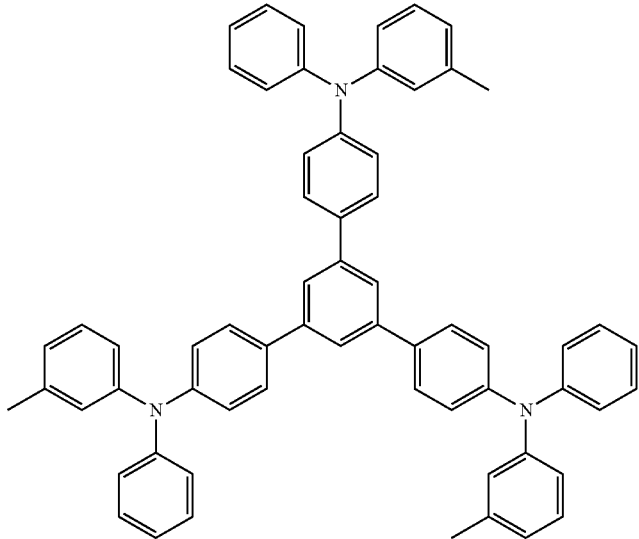 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 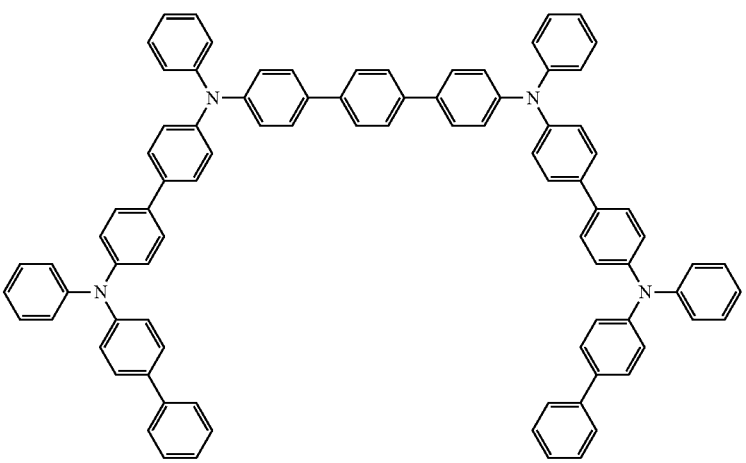 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
|---|---|---|
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 |

TABLE 1-continued
| MATERIAL | EXAMPLES OF MATERIAL | PUBLICATIONS |
|---|---|---|
| Indolocarbazoles | 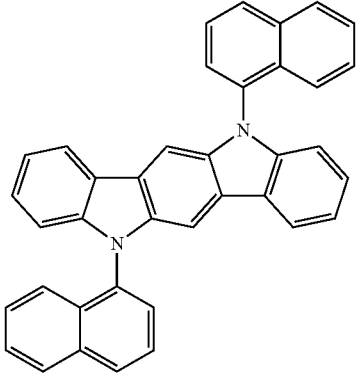 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 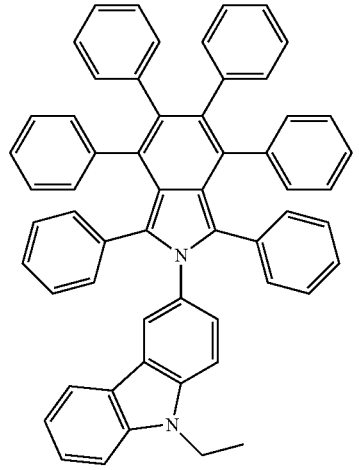 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 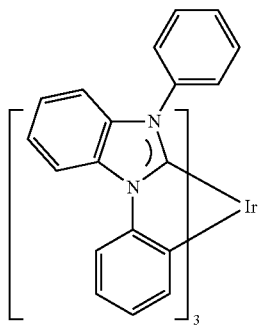 | US20080018221 |
Phosphorescent OLED host materials
Red hosts
| Arylcarbazoles | 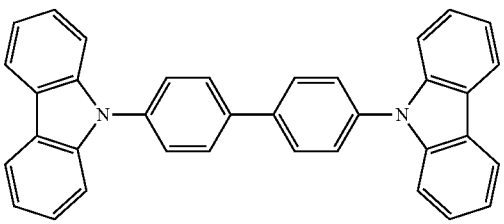 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 1-continued

| MATERIAL | EXAMPLES OF MATERIAL | PUBLICATIONS |
| --- | --- | --- |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxy-benzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 1-continued
| MATERIAL | EXAMPLES OF MATERIAL | PUBLICATIONS |
|---|---|---|
| Zinc complexes | 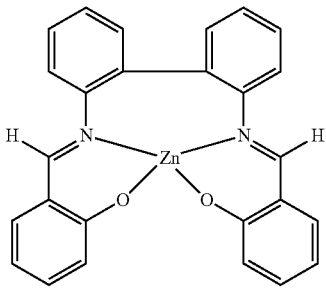 | WO2009062578 |
| Green hosts | | |
| Arylcarbazoles | 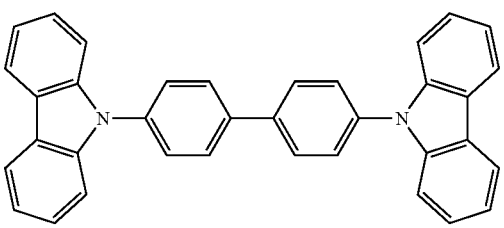 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 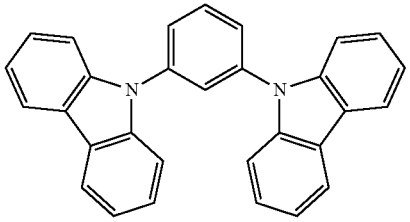 [SMILES: c1cc(-n2c3ccccc3c3ccccc32)cc(-n2c3ccccc3c3ccccc32)c1] | US20030175553 |
| | 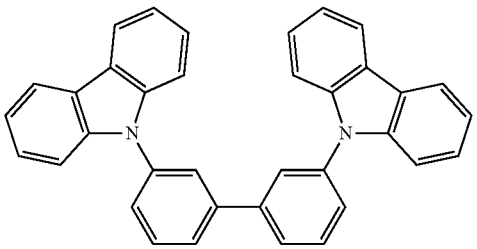 [SMILES: c1cc(-c2cccc(-n3c4ccccc4c4ccccc43)c2)cc(-n2c3ccccc3c3ccccc32)c1] | WO2001039234 |
| Aryltriphenylene compounds | 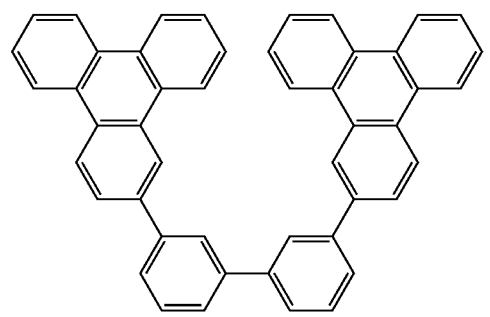 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE 1-continued

| MATERIAL | EXAMPLES OF MATERIAL | PUBLICATIONS |
| --- | --- | --- |
| | | US20060280965 |
| | | WO2009021126 |
| Donor acceptor type molecules | | WO2008056746 |
| Aza-carbazole/ DBT/DBF | | JP2008074939 |
| Polymers (e.g., PVK) | | Appl. Phys. Lett. 77, 2280 (2000) |

TABLE 1-continued

| MATERIAL | EXAMPLES OF MATERIAL | PUBLICATIONS |
|---|---|---|
| Spirofluorene compounds | | WO2004093207 |
| Metal phenoxy-benzooxazole compounds | | WO2005089025 |
| | | WO2006132173 |
| | | JP200511610 |
| Spirofluorene-carbazole compounds | | JP2007254297 |

TABLE 1-continued
| MATERIAL | EXAMPLES OF MATERIAL | PUBLICATIONS |
|---|---|---|
| | 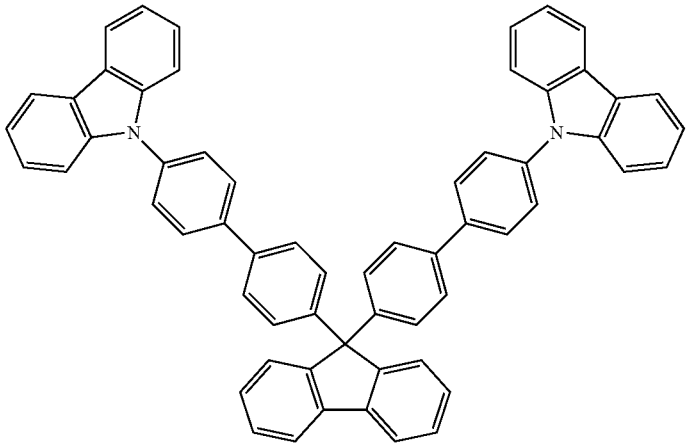 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 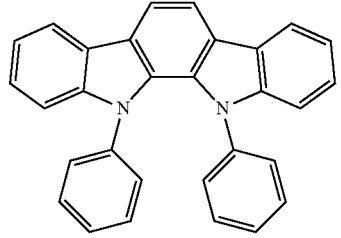 [SMILES: c1ccc(-n2c3ccccc3c3ccc4c5ccccc5n(-c5ccccc5)c4c32)cc1] | WO2007063796 |
| | 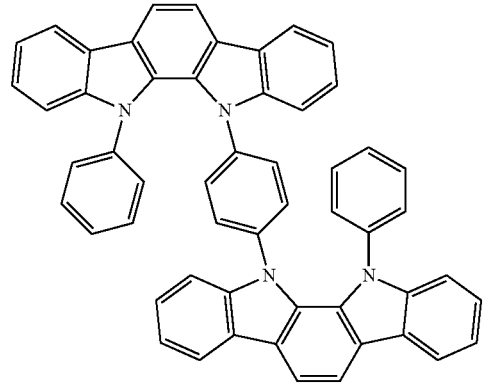 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 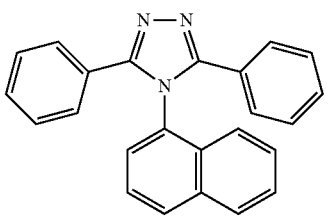 [SMILES: c1ccc(-c2nnc(-c3ccccc3)n2-c2cccc3ccccc23)cc1] | J. Appl. Phys. 90, 5048 (2001) |
| | 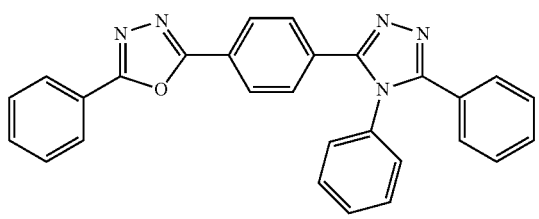 [SMILES: c1ccc(-c2nnc(-c3ccc(-c4nnc(-c5ccccc5)n4-c4ccccc4)cc3)o2)cc1] | WO2004107822 |

TABLE 1-continued
| MATERIAL | EXAMPLES OF MATERIAL | PUBLICATIONS |
|---|---|---|
| Tetraphenylene complexes | 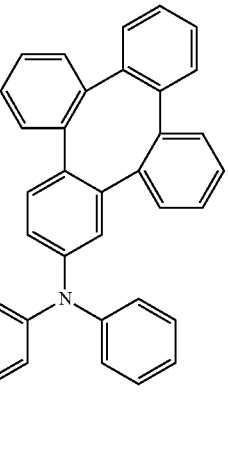 | US20050112407 |
| Metal phenoxypyridine compounds | 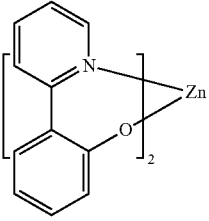 | WO2005030900 |
| Metal coordination complexes (e.g., Zn, Al with N^N ligands) | 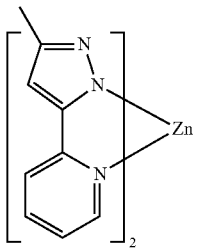 | US20040137268, US20040137267 |
| Blue hosts | | |
| Arylcarbazoles | 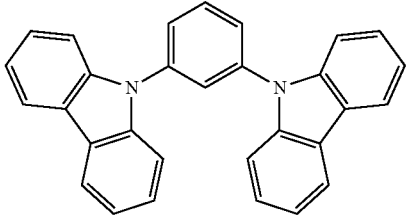 [SMILES: c1cc(-n2c3ccccc3c3ccccc32)cc(-n2c3ccccc3c3ccccc32)c1] | Appl. Phys. Lett, 82, 2422 (2003) |
| | 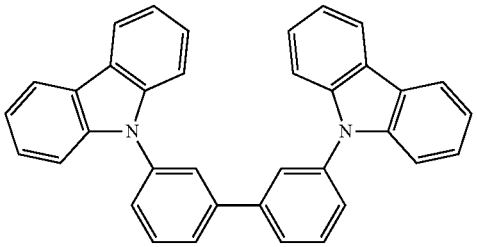 [SMILES: c1cc(-c2cccc(-n3c4ccccc4c4ccccc43)c2)cc(-n2c3ccccc3c3ccccc32)c1] | US20070190359 |

TABLE 1-continued
| MATERIAL | EXAMPLES OF MATERIAL | PUBLICATIONS |
|---|---|---|
| Dibenzothiophene/ Dibenzofuran- carbazole compounds | 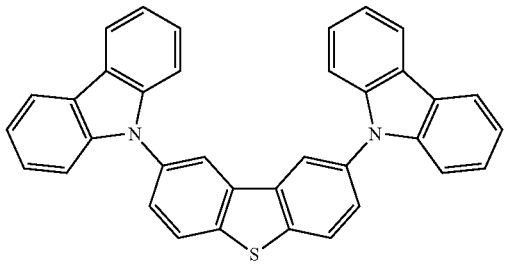 [SMILES: c1ccc2c(c1)c1ccccc1n2-c1ccc2sc3ccc(-n4c5ccccc5c5ccccc54)cc3c2c1] | WO2006114966, US20090167162 |
| | 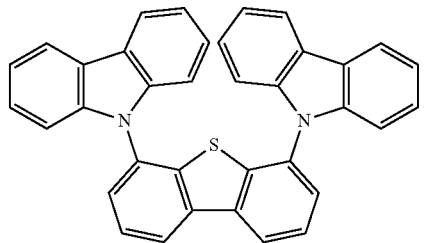 [SMILES: c1cc(-n2c3ccccc3c3ccccc32)c2sc3c(-n4c5ccccc5c5ccccc54)cccc3c2c1] | US20090167162 |
| | 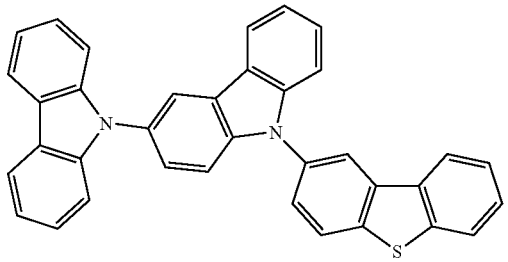 [SMILES: c1ccc2c(c1)sc1ccc(-n3c4ccccc4c4cc(-n5c6ccccc6c6ccccc65)ccc43)cc12] | WO2009086028 |
| | 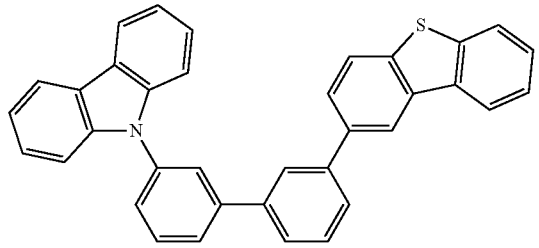 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 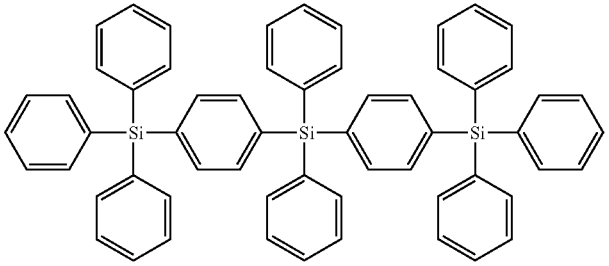 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 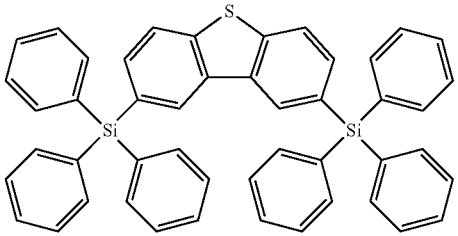 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 1-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | US7154114 |

Phosphorescent dopants
Red dopants

| | | |
| --- | --- | --- |
| Heavy metal porphyrins (e.g., PtOEP) | | Nature 395, 151 (1998) |
| Iridium (III) organometallic complexes | | Appl. Phys. Lett. 78, 1622 (2001) |

TABLE 1-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 1-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum (II) organometallic complexes | | WO2003040257 |

TABLE 1-continued

| MATERIAL | EXAMPLES OF MATERIAL | PUBLICATIONS |
| --- | --- | --- |
| Osminum (III) complexes | [Structure: pyrazole-pyridine ligand with CF₃ group coordinated to Os(PPhMe₂)₂, with subscript 2] | Chem. Mater. 17, 3532 (2005) |
| Ruthenium (II) complexes | [Structure: pyrazole-isoquinoline ligand with tBu group coordinated to Ru(PPhMe₂)₂, with subscript 2] | Adv. Mater. 17, 1059 (2005) |
| Rhenium (I), (II), and (III) complexes | [Structure: 8-hydroxyquinoline coordinated to Re(CO)₄] | US20050244673 |
| Green dopants | | |
| Iridium (II) organometallic complexes | [Structure: tris(2-phenylpyridine)iridium, Ir(ppy)₃]<br>and its derivatives | Inorg. Chem. 40, 1704 (2001) |
| | [Structure: bis(2-phenylpyridine)iridium acetylacetonate, Ir(ppy)₂(acac)] | US20020034656 |

TABLE 1-continued

| MATERIAL | EXAMPLES OF MATERIAL | PUBLICATIONS |
|---|---|---|
| | | US7332232 |
| | | US20090108737 |
| | | US20090039776 |
| | | US6921915 |

TABLE 1-continued

| MATERIAL | EXAMPLES OF MATERIAL | PUBLICATIONS |
|---|---|---|
| | | US6687266 |
| | | Chem. Mater. 16, 2480 (2004) |
| | | US20070190359 |
| | | US20060008670<br>JP2007123392 |
| | | Adv. Mater. 16, 2003 (2004) |

| MATERIAL | EXAMPLES OF MATERIAL | PUBLICATIONS |
|---|---|---|
| | 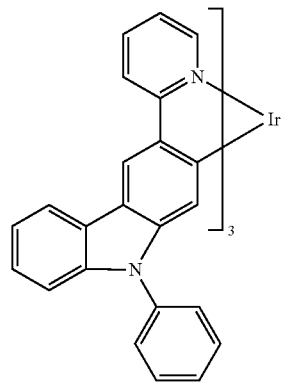 | Angew. Chem. Int. Ed. 2006, 45, 7800 |
| | 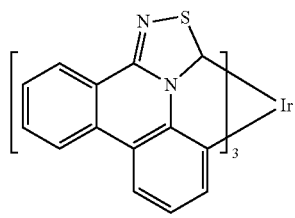 | WO2009050290 |
| | 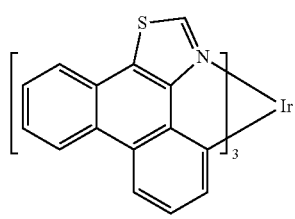 | US20090165846 |
| | 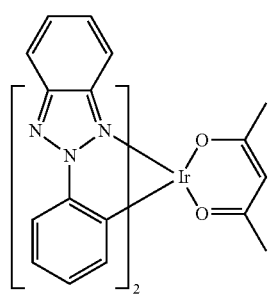 | US20080015355 |
| Monomer for polymeric metal organometallic compounds | 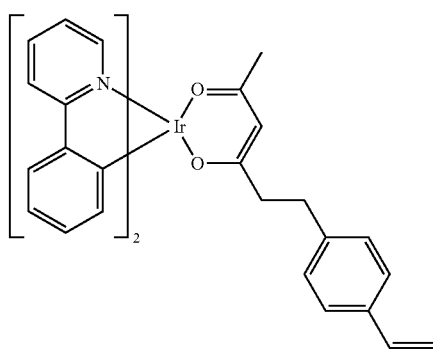 | US7250226, US7396598 |

TABLE 1-continued
| MATERIAL | EXAMPLES OF MATERIAL | PUBLICATIONS |
|---|---|---|
| Pt (II) organometallic complexes, including polydentated ligands | 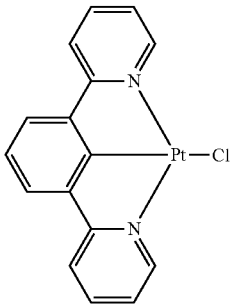 | Appl. Phys. Lett. 86, 153505 (2005) |
| | 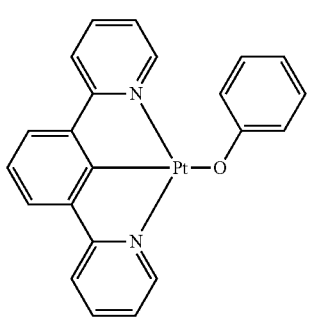 | Appl. Phys. Lett. 86, 153505 (2005) |
| | 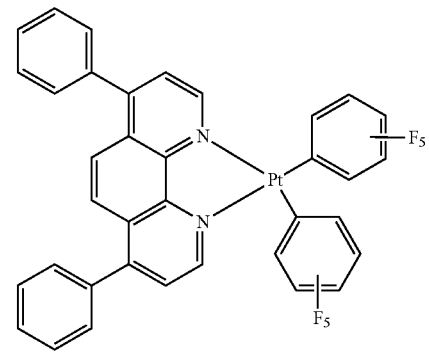 | Chem. Lett. 34, 592 (2005) |
| | 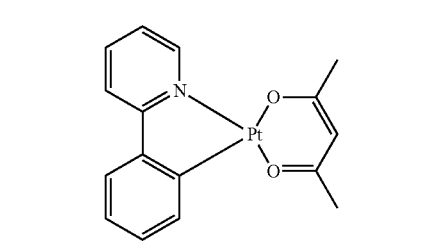 | WO2002015645 |
| | 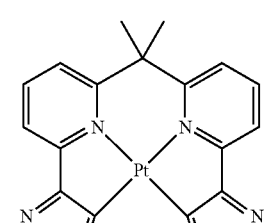 | US20060263635 |

TABLE 1-continued
| MATERIAL | EXAMPLES OF MATERIAL | PUBLICATIONS |
|---|---|---|
| Cu complexes | 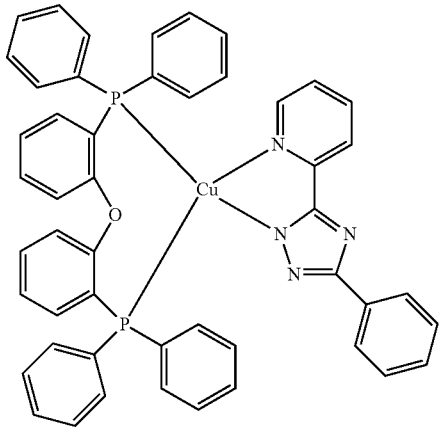 | WO2009000673 |
| Gold complexes | 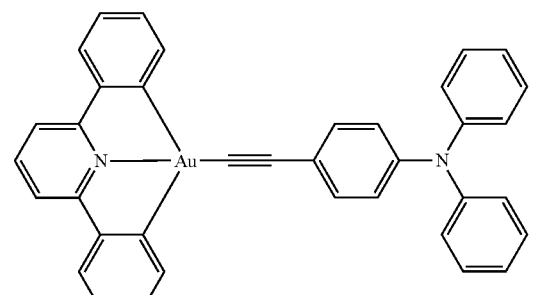 | Chem. Commun. 2906 (2005) |
| Rhenium (III) complexes | 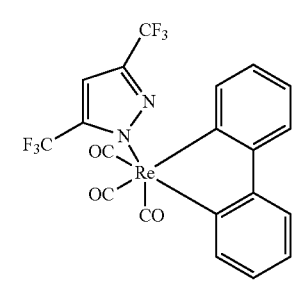 | Inorg. Chem. 42, 1248 (2003) |
| Deuterated organometallic complexes | 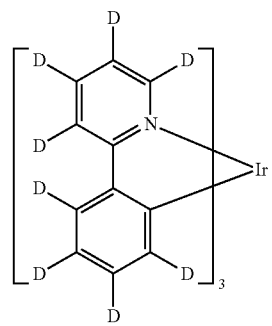 | US20030138657 |

TABLE 1-continued
| MATERIAL | EXAMPLES OF MATERIAL | PUBLICATIONS |
|---|---|---|
| Organometallic complexes with two or more metal centers | 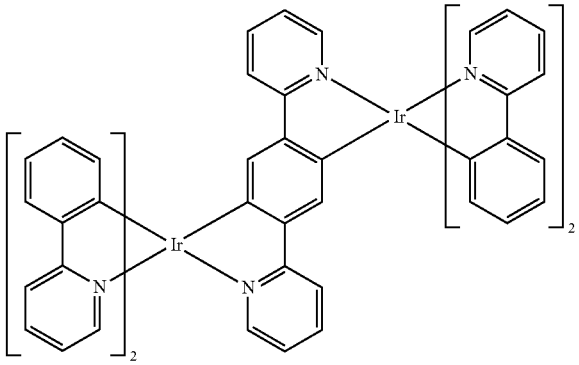 | US20030152802 |
| | 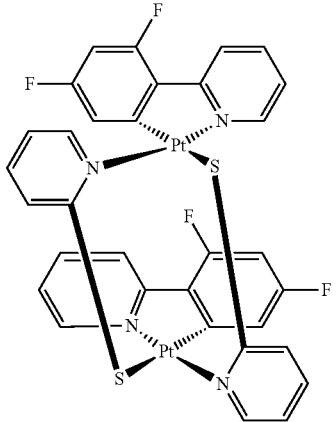 | US7090928 |
| Blue dopants | | |
| Iridium (III) organometallic complexes | 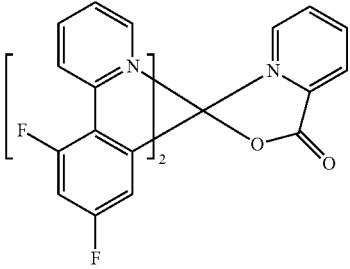 | WO2002002714 |
| | 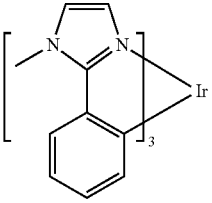 | WO2006009024 |
| | 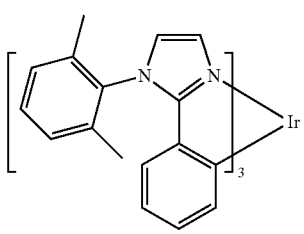 | US20060251923 |

TABLE 1-continued

| MATERIAL | EXAMPLES OF MATERIAL | PUBLICATIONS |
|---|---|---|
| | (imidazole-phenyl Ir complex, tris) | US7393599, WO2006056418, US20050260441, WO2005019373 |
| | (benzimidazole-benzofuran Ir complex, tris) | US7534505 |
| | (bis-imidazole phenylene Ir⁺ complex) | US7445855 |
| | (imidazo-phenanthridine Ir complex, tris) | US20070190359, US20080297033 |
| | (pyrazole-biphenyl Ir complex, tris) | US7338722 |
| | (pyrazole-pyridine Ir complex, tris) | US20020134984 |

| MATERIAL | EXAMPLES OF MATERIAL | PUBLICATIONS |
|---|---|---|
| | 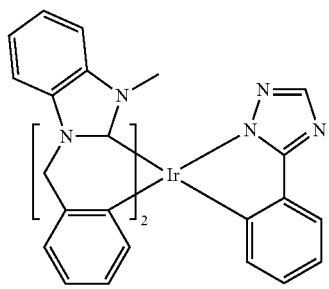 | Angew. Chem. Int. Ed. 47, 1 (2008) |
| | 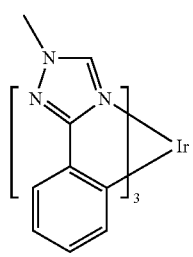 | Chem. Mater. 18, 5119 (2006) |
| | 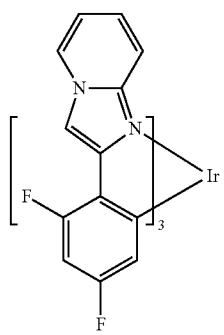 | Inorg. Chem. 46, 4308 (2007) |
| | 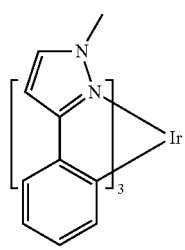 | WO2005123873 |
| | 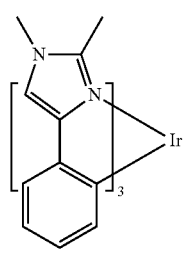 | WO2005123873 |
| | 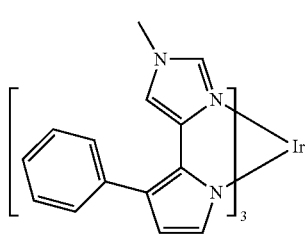 | WO2007004380 |

TABLE 1-continued

| MATERIAL | EXAMPLES OF MATERIAL | PUBLICATIONS |
| --- | --- | --- |
| | | WO2006082742 |
| Osmium (II) complexes | | US7279704 |
| | | Organometallics 23, 3745 (2004) |
| Gold complexes | | Appl. Phys. Lett. 74, 1361 (1999) |
| Platinum (II) complexes | | WO2006098120, WO2006103874 |

Exciton/hole blocking layer materials

TABLE 1-continued
| MATERIAL | EXAMPLES OF MATERIAL | PUBLICATIONS |
|---|---|---|
| Bathocuprine compounds (e.g., BCP, BPhen) | 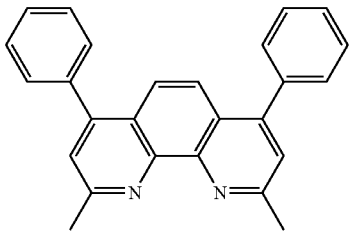 [SMILES: Cc1cc(-c2ccccc2)c2ccc3c(-c4ccccc4)cc(C)nc3c2n1] 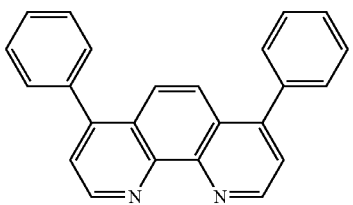 [SMILES: c1ccc(-c2ccnc3c2ccc2c(-c4ccccc4)ccnc23)cc1] | Appl. Phys. Lett. 75, 4 (1999)<br><br>Appl. Phys. Lett. 79, 449 (2001) |
| Metal 8-hydroxyquinolates (e.g., BAlq) | 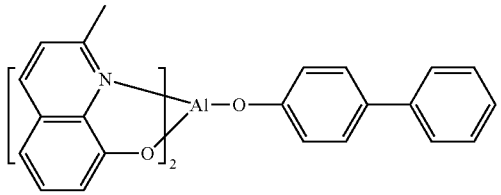 | Appl. Phys. Lett. 81, 162 (2002) |
| 5-member ring electron deficient heterocycles such as triazole, oxadiazole, imidazole, benzoimidazole | 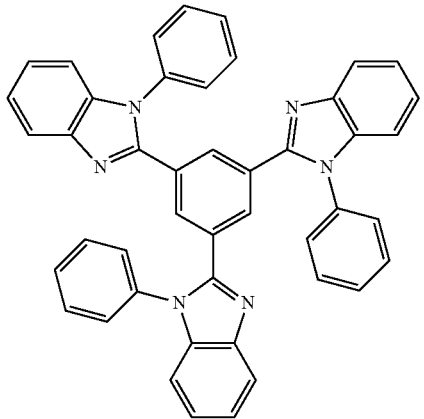 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 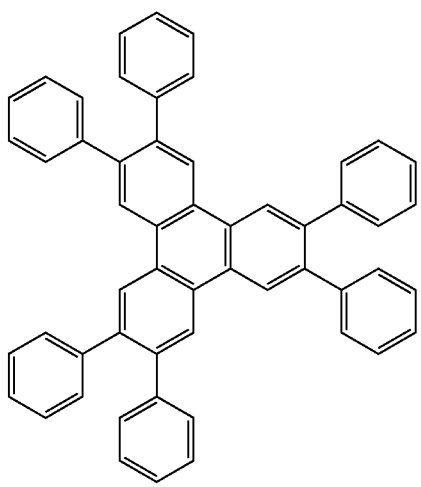 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 1-continued
| MATERIAL | EXAMPLES OF MATERIAL | PUBLICATIONS |
|---|---|---|
| Fluorinated aromatic compounds | 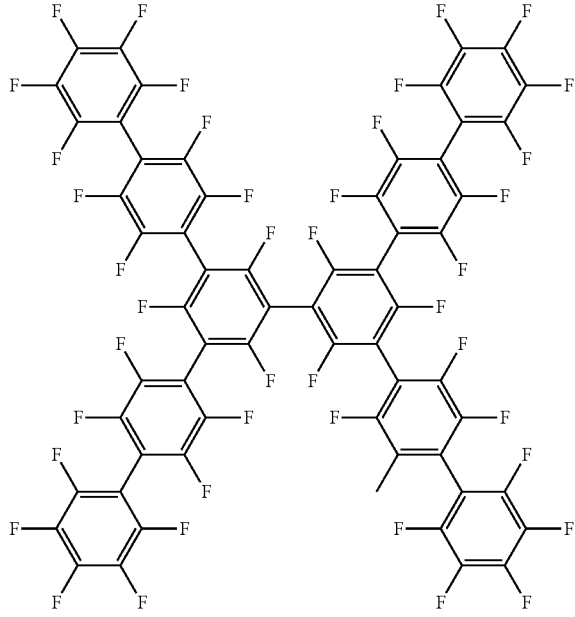 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett, 79, 156 (2001) |
| Phenothiazine-S-oxide | 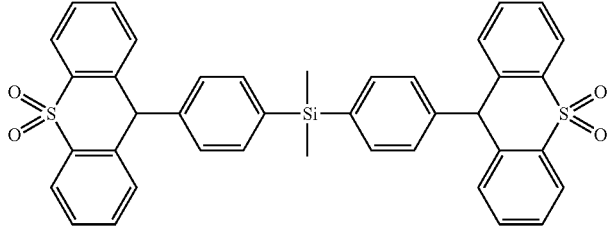 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Electron transporting materials | | |
| Anthracene-benzoimidazole compounds | 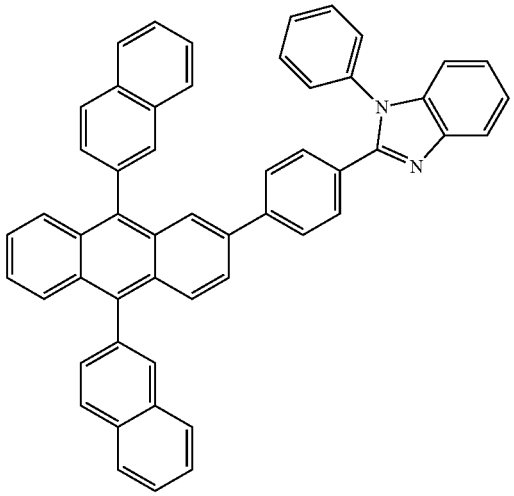 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 1-continued

| MATERIAL | EXAMPLES OF MATERIAL | PUBLICATIONS |
| --- | --- | --- |
| | | US20090179554 |
| Aza tiphenylene derivates | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987)<br>US7230107 |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |

| MATERIAL | EXAMPLES OF MATERIAL | PUBLICATIONS |
|---|---|---|
| | 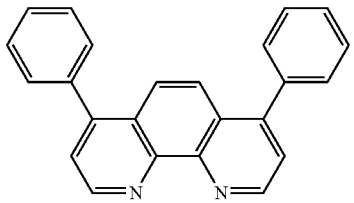 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 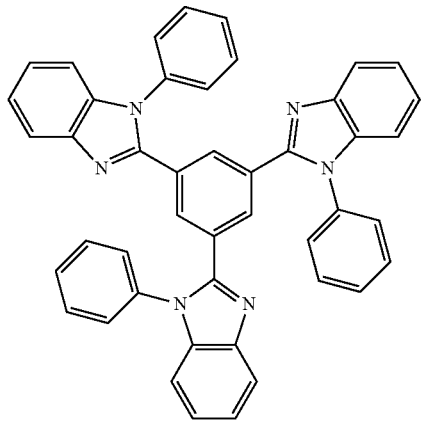 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 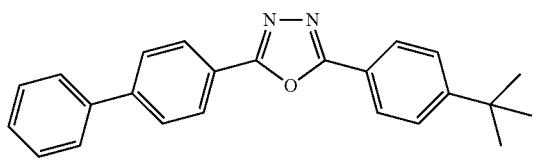 [SMILES: CC(C)(C)c1ccc(-c2nnc(-c3ccc(-c4ccccc4)cc3)o2)cc1] | Appl. Phys. Lett. 55, 1489 (1989) |
| | 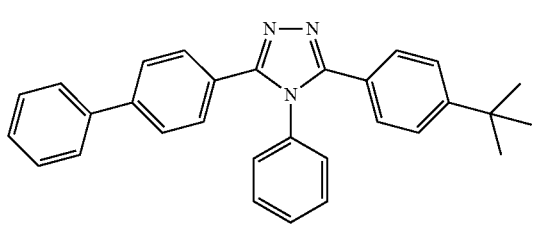 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 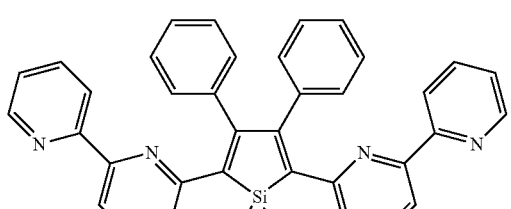 | Org. Electron. 4, 113 (2003) |
| Arylborane compounds | 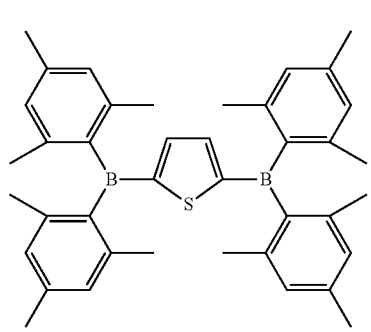 | J. Am. Chem. Soc. 120, 9714 (1998) |

TABLE 1-continued

| MATERIAL | EXAMPLES OF MATERIAL | PUBLICATIONS |
|---|---|---|
| Fluorinated aromatic compounds | | J. Am. Chem. Soc. 122, 1832 (2000) |
| Fullerene (e.g., C60) | | US20090101870 |
| Triazine complexes | | US20040036077 |
| Zn (N^N) complexes | | US6528187 |

EXPERIMENTAL

Synthetic Examples

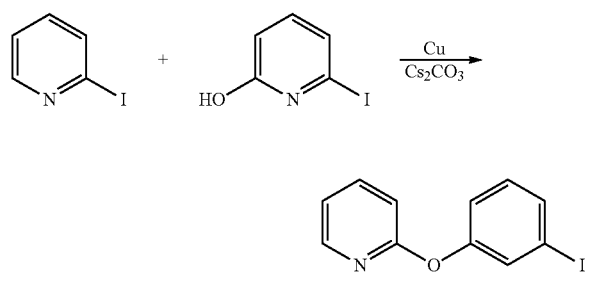

Synthesis of 2-(3-iodophenoxy)pyridine

A 250 mL reaction flask was charged with cesium carbonate (29.34 g, 90 mmol) in DMF (120 mL) to give a white suspension. 2-Iodopyridine (6.4 ml, 60.2 mmol), 3-iodophenol (13.2 g, 60.0 mmol) and copper powder (0.369 g, 5.81 mmol) were added. This was stirred at 115° C. (oil bath) for 18 h. The mixture was then filtered through celite and washed with dichloromethane. The filtrate was washed with saturated NaOH then 10% aqueous LiCl then twice with water. The organic layer was dried over sodium sulfate and chromatographed on silica gel with 50-100% DCM in hexane to give 13.54 g (76%) of 2-(3-iodophenoxy)pyridine as a white solid.

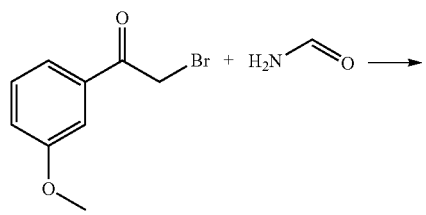

Synthesis of 5-(3-methoxyphenyl)-1H-imidazole

2-Bromo-1-(3-methoxyphenyl)ethanone (25.0 g, 109 mmol) was added to a 250 mL round-bottom flask. The reaction mixture was diluted with 100 mL of formamide. This was stirred at 165° C. for 2.5 h. Water and ethyl acetate (200 mL each) were then added and the layers separated. The aqueous layer was basified to pH 12, and extracted with ethyl acetate (200 mL). The combined organic layers were dried over sodium sulfate and chromatographed on silica gel with ethyl acetate, then 5% methanol in DCM, to afford 14.8 g (78%) of 5-(3-methoxyphenyl)-1H-imidazole.

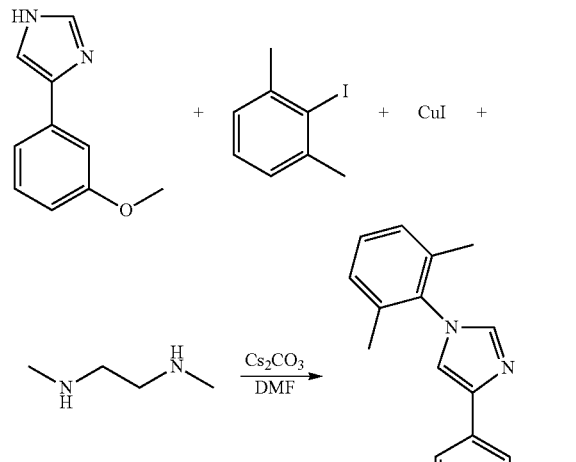

Synthesis of 1-(2,6-dimethylphenyl)-4-(3-methoxyphenyl)-1H-imidazole 5-(3-Methoxyphenyl)-1H-imidazole (9.91 g, 56.9 mmol) and 2-iodo-1,3-dimethylbenzene (11.0 g, 47.4 mmol) were added to a 150 mL glass pressure flask. Copper(I) iodide (0.90 g, 4.74 mmol) was added and the reaction mixture was diluted with DMF (47 mL). N,N'-Dimethylethane-1,2-diamine (2.0 mL, 18.96 mmol) and cesium carbonate (30.9 g, 95 mmol) were added and the flask was flushed with nitrogen, sealed and placed in an oil bath heated to 170° C. for 44 h. Ethyl acetate was added and the crude mixture was filtered through a plug of silica gel. The filtrate was washed with water and the organic layer was concentrated and chromatographed on silica gel, eluting with ethyl acetate to give 5.2 g of product. This was re-chromatographed on silica gel, eluting with 0-7% ethyl acetate in DCM to give 4.1 g of 1-(2,6-dimethylphenyl)-4-(3-methoxyphenyl)-1H-imidazole as a tan solid.

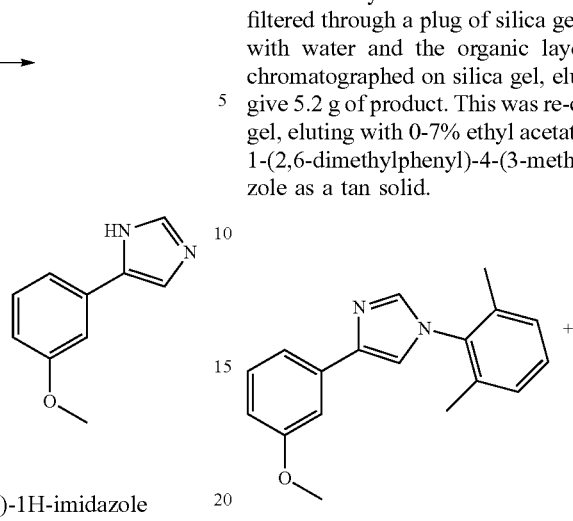

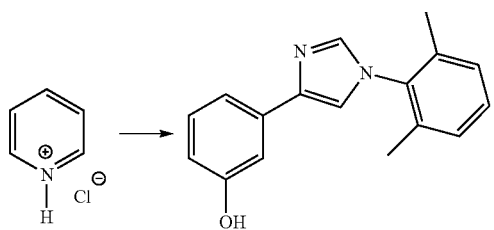

Synthesis of 3-(1-(2,6-dimethylphenyl)-1H-imidazol-4-yl)phenol 1-(2,6-Dimethylphenyl)-4-(3-methoxyphenyl)-1H-imidazole (4.0 g, 14.4 mmol) was added to a 250 mL round-bottom flask. Pyridine hydrochloride (14.3 g) was added and the reaction mixture was stirred in an oil bath at 200° C. for 5 h. The mixture was then cooled to 130° C. and water was added along with saturated sodium bicarbonate solution. The crude solid was filtered and chromatographed on silica gel, eluting with 0-5% methanol in DCM to give 2.7 g of product. This material was lixiviated with ether and hexane and filtered to give 2.5 g of 3-(1-(2,6-dimethylphenyl)-1H-imidazol-4-yl)phenol as a white powder.

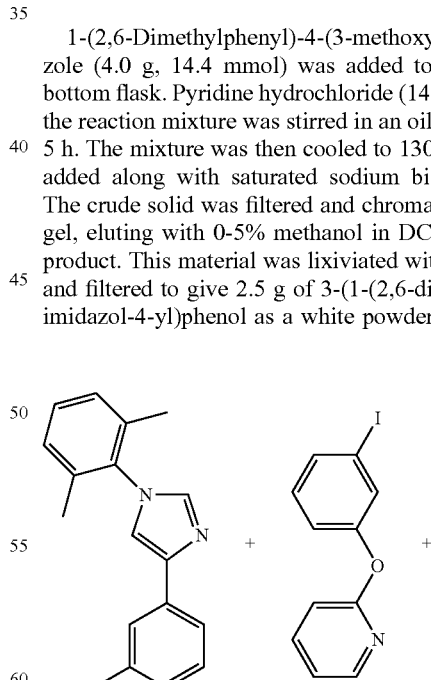

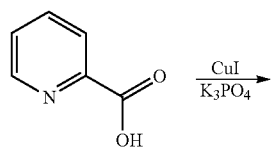

-continued

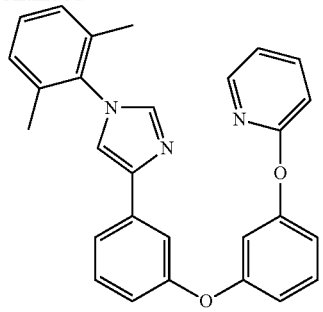

Synthesis of 2-(3-(3-(1-(2,6-dimethylphenyl)-1H-imidazol-4-yl)phenoxy)phenoxy)pyridine 3-(1-(2,6-Dimethylphenyl)-1H-imidazol-4-yl)phenol (2.46 g, 9.31 mmol), 2-(3-iodophenoxy)pyridine (3.04 g, 10.24 mmol) and copper(I) iodide (0.532 g, 2.79 mmol) were added to a 250 mL round-bottom flask. The reaction mixture was diluted with DMSO (100 mL) and picolinic acid (1.7 g, 13.96 mmol) and potassium phosphate (6.9 g, 32.6 mmol) were added. The flask was evacuated and backfilled 2 times with nitrogen, and the reaction was stirred to an internal temperature of 105° C. for 24 h. The heat was removed and the mixture was diluted with ethyl acetate and filtered through celite. The filtrate was washed with water 3 times. The organic layer was dried over sodium sulfate and chromatographed on silica gel, eluting with 25-40% ethyl acetate in hexane to give 3.9 g of 2-(3-(3-(1-(2,6-dimethylphenyl)-1H-imidazol-4-yl)phenoxy)phenoxy)pyridine as a white foam.

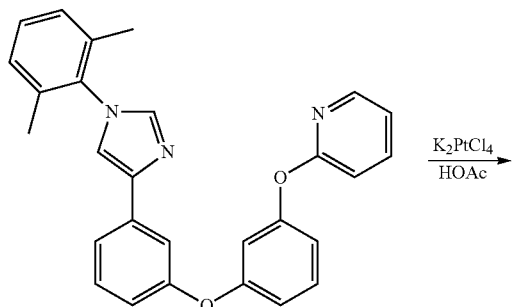

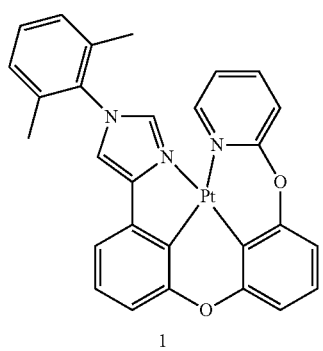

1

Synthesis of Compound 1

2-(3-(3-(1-(2,6-Dimethylphenyl)-1H-imidazol-4-yl)phenoxy)phenoxy)pyridine (3.38 g, 7.80 mmol) and potassium tetrachloroplatinate (3.24 g, 7.80 mmol) were added to a 500 mL round-bottom flask. The reaction mixture was diluted with acetic acid (150 mL) and heated to reflux for 68 h. The reaction mixture was cooled to ambient temperature and 50 mL of water was added. The resulting solid was filtered and washed with water. The crude solid was dissolved in DCM and placed in a reparatory funnel and washed with water. The organic layer was dried and chromatographed on silica gel, eluting with DCM to give a yellow solid 3.5 g. The solid was recrystallized from DCM/MeOH to yield 2.5 g (51%) of Compound 1 as a yellow solid.

Device Examples

All device examples were fabricated by high vacuum (<10$^{-7}$ Torr) thermal evaporation. The anode electrode is 800 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package.

The organic stack of the devices consisted of sequentially, from the ITO surface, 100 Å of LG101 (purchased from LG Chem) as the hole injection layer (HIL), 300 Å of either NPD or TAPC as the hole transporting layer (HTL), 300 Å of UGH2 doped with 10% or 15% of the Pt (II) complex as the emissive layer (EML), 50 Å of Compound B as the blocking layer (BL), and 400 Å of Alq or 3TPYMBas the electron transporting layer (ETL).

As used herein, the following compounds have the following structures:

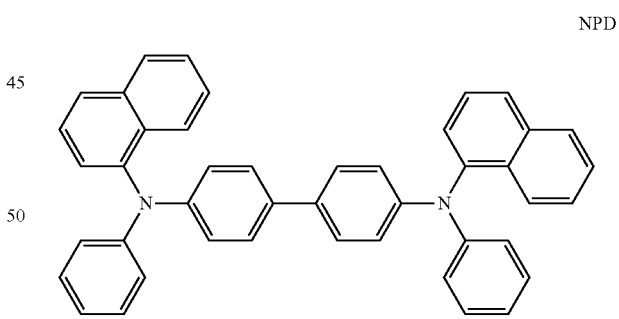

NPD

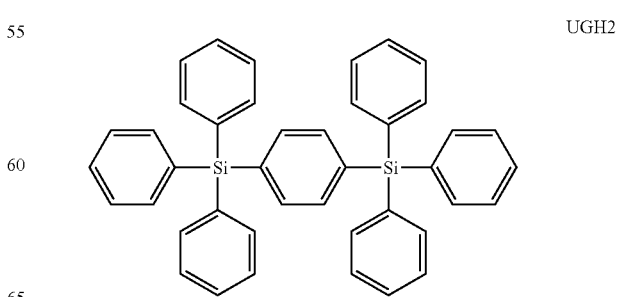

UGH2

TAPC

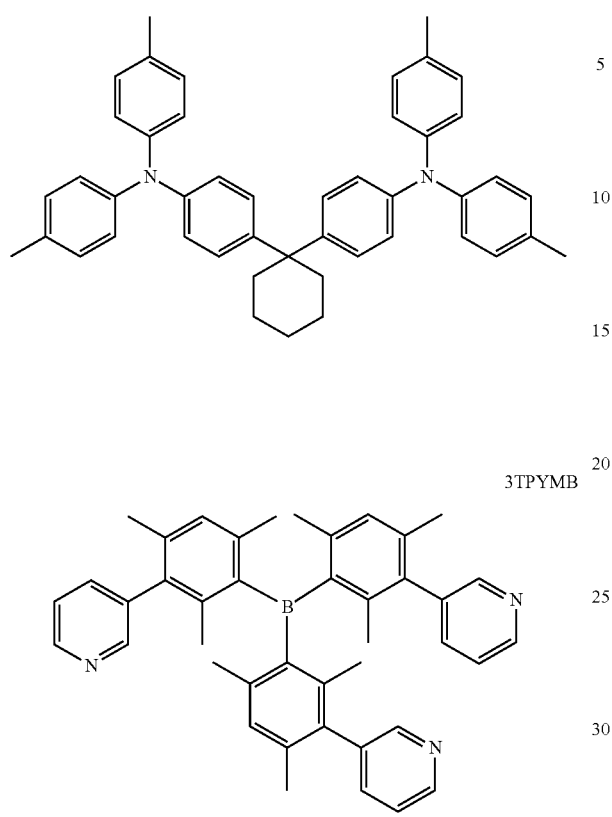

3TPYMB

Compound B

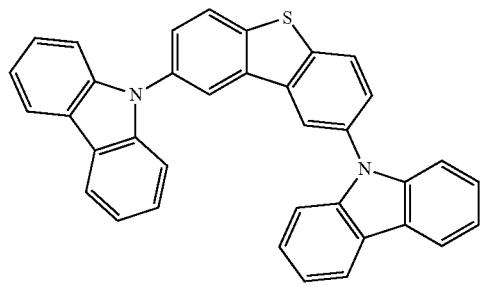

Alq

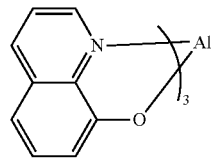

Compound 1

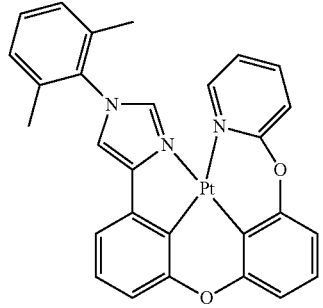

The device examples are detailed in Table 2, and the corresponding device data is summarized in Table 3. Ex. is an abbreviation for Example.

TABLE 2

VTE PHOLEDs

| Device Ex. | HIL | HTL | EML doping % | BL | ETL |
|---|---|---|---|---|---|
| 1 | LG101 | NPD | 10% | Cmpd. B | Alq |
| 2 | LG101 | TAPC | 10% | Cmpd. B | 3TPYMB |
| 3 | LG101 | TAPC | 15% | Cmpd. B | 3TPYMB |

TABLE 3

VTE Device Data

| Device Ex. | 1931 CIE | | $\lambda_{max}$ (nm) | FWHM (nm) | At 1000 nits | | | | 20 mA/cm² $L_0$ (nits) |
|---|---|---|---|---|---|---|---|---|---|
| | X | Y | | | Voltage (V) | LE (Cd/A) | EQE (%) | PE (lm/W) | |
| 1 | 0.179 | 0.235 | 466 | 78 | 11.1 | 4 | 2.4 | 1.1 | 836 |
| 2 | 0.192 | 0.220 | 464 | 76 | 11.3 | 5.5 | 3.5 | 1.5 | 1082 |
| 3 | 0.194 | 0.253 | 466 | 92 | 10.2 | 6.7 | 3.7 | 2.1 | 1310 |

The device data shows that compounds of Formula 1 can be used in OLEDs to make high triple emitters providing blue emission. In the representative devices, the $\lambda_{max}$ of the emission ranges from 464-466 nm, with CIE X coordinates between 0.179 and 0.194 and CIE Y between 0.22 and 0.253. The full-width half maximum (FWHM) for Device 1 (78 nm) and Device 2 (76 nm) show that narrow emission can be achieved with compounds of Formula I.

TD-DFT calculations, which predict the properties of inventive compounds and comparative compounds, are provided in Table 4. The HOMO, LUMO, the HOMO-LUMO energy gap and triplet energies for each structure were calculated using TD-DFT calculations with the Gaussian software package at the B3LYP/cep-31g functional and basis set.

TABLE 4

| Ex. | Structure | HOMO (eV) | LUMO (eV) | Gap (eV) | $T_1$ (nm) |
| --- | --- | --- | --- | --- | --- |
| 4 | 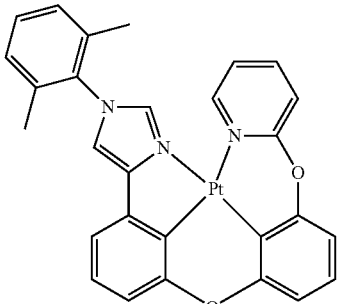<br>Compound 1 | −4.82 | −1.60 | −3.22 | 494 |
| 5 | 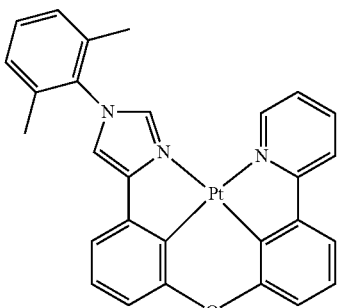<br>Comparative Compound 1 | −4.78 | −1.65 | −3.13 | 567 |
| 6 | 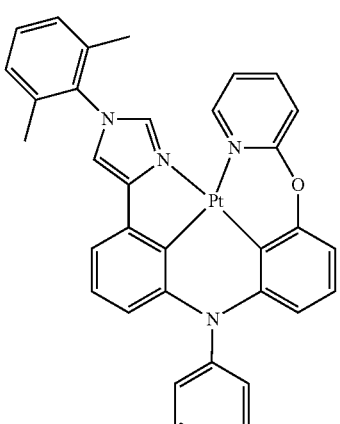<br>Compound 2 | −4.52 | −1.64 | −2.89 | 518 |

TABLE 4-continued
| Ex. | Structure | HOMO (eV) | LUMO (eV) | Gap (eV) | T₁ (nm) |
|---|---|---|---|---|---|
| 7 | 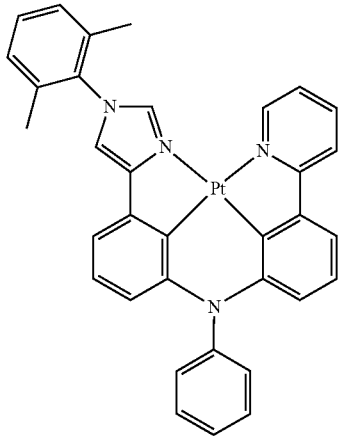 Comparative Compound 2 | −4.55 | −1.67 | −2.88 | 566 |
| 8 | 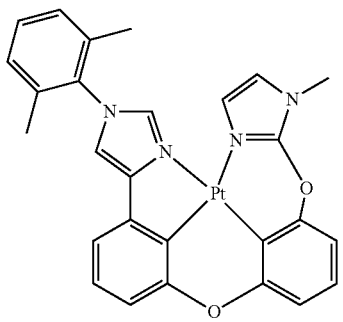 Compound 3 | −4.66 | −1.00 | −3.65 | 443 |
| 9 | 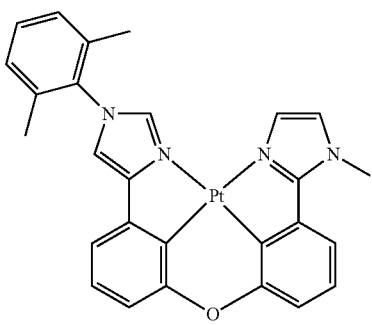 Comparative Compound 3 | −4.59 | −0.99 | −3.60 | 496 |

TABLE 4-continued

| Ex. | Structure | HOMO (eV) | LUMO (eV) | Gap (eV) | T₁ (nm) |
|---|---|---|---|---|---|
| 10 | Compound 4 | −4.15 | −0.91 | −3.24 | 460 |
| 11 | Comparative Compound 4 | −4.11 | −0.86 | −3.25 | 549 |

Table 4 shows HOMO energy level, LUMO energy level, the HOMO-LUMO energy gap and predicted triplet energies for a series of isoimidazole Pt compounds with $L_2$ as a bridging group. The table also includes data for corresponding isoimidazole Pt compounds with a single bond at $L_2$, i.e., without $L_2$ as a bridging group. For the series of complexes, $L_2$ is an oxygen bridge. While the HOMO, LUMO and energy gap values are similar for Compound 1 and Comparative Example 1, the triplet energy for Comparative Example 1, where $L_2$=0, is lower. For Comparative Compounds 1, 2, 3 and 4, the triplet energy is governed by the lower energy cyclometallated ligand. Conversely, for Compounds 1, 2, 3 and 4, the oxygen bridge disrupts the conjugation and the triplet energy is controlled by the higher energy isoimidazole ligand. Therefore, the data shows that $L_2$ may provide high triplet energy.

It can also be seen from Table 4 that a substitution at $L_3$ may tune the properties of the compounds. In particular, $L_3$ is an oxygen bridge or an aryl substituted nitrogen in Compounds 1 and 2, respectively, which has a large effect on the HOMO and triplet energies, but relatively little effect on the LUMO energy. The same effect is measured throughout the series of compounds. Therefore, the $L_3$ bridge may function as a useful tool to tune the HOMO energy of the compound and red-shift the emission to a more useful color. It is also noted that a more shallow HOMO energy seen for the arylamine bridged structures, i.e., Compounds 2 and 4, may allow for the molecule to be a better hole trap in an OLED. Without being bound by theory, it is believed that if the molecule is a good hole trap, then it can result in higher electroluminescent efficiencies.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:
1. A compound having the formula:

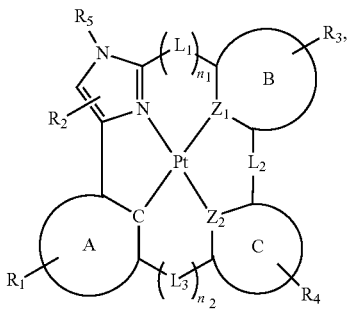

Formula I wherein A, B, and C are each independently a 5- or 6-membered carbocyclic or heterocyclic ring;
wherein $L_1$ and $L_3$ are independently selected from the group consisting of a single bond, BR, NR, PR, O, S, Se, C=O, S=O, $SO_2$, CRR', SiRR', and GeRR';
wherein $L_2$ is selected from the group consisting of BR, NR, PR, O, S, Se, C=O, S=O, $SO_2$, CRR', SiRR', and GeRR';
wherein $n_1$ is 0 or 1;
wherein $n_2$ is 0 or 1;
wherein $n_1+n_2$ is at least equal to 1;
wherein $Z_1$ and $Z_2$ are independently a nitrogen atom or a carbon atom;
wherein $R_1$, $R_2$, $R_3$, and $R_4$ may represent mono-, di-, tri-, or tetra-substitutions;
wherein R, R', $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R_1$ is optionally fused to A;
wherein $R_3$ is optionally fused to B;
wherein $R_4$ is optionally fused to C;
wherein $R_3$ and $R_4$ are optionally joined to form into a ring;
wherein $R_3$ and $L_2$ are optionally joined to form into a ring;
wherein $R_4$ and $L_2$ are optionally joined to form into a ring; and
wherein at least one of the following (i)-(vi) is true:
(i) $n_1=0$ and $n_2=1$;
(ii) wherein $R_5$ is

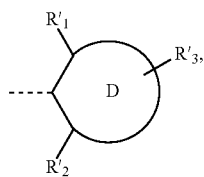

wherein $R'_1$ and $R'_2$ are independently selected from the group consisting of halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, partially or fully deuterated variations thereof, and combinations thereof;
wherein D is 5-membered or 6-membered carbocyclic or heterocyclic ring that is optionally further substituted with $R'_3$; and
wherein $R'_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
(iii) wherein the compound has the structure of Formula IIA,

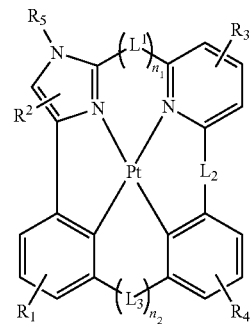

(iv) wherein the compound has the structure of Formula IIIA,

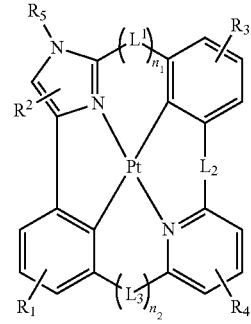

(v) wherein the compound has the structure of Formula VIA,

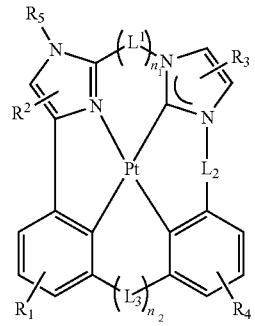

and (vi) wherein the compound has the structure of Formula VIIA,

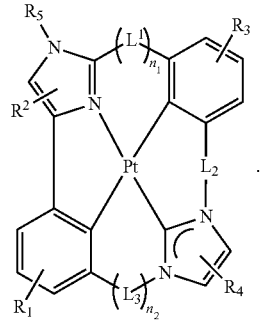

2. The compound of claim 1, wherein $R_5$ is a 2,6-disubstituted aryl.

3. The compound of claim 1, wherein $R_5$ is

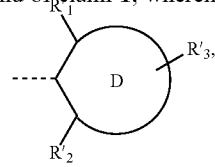

wherein $R'_1$ and $R'_2$ are independently selected from the group consisting of halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein D is 5-membered or 6-membered carbocyclic or heterocyclic ring that is optionally further substituted with $R'_3$; and wherein $R'_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

4. The compound of claim 3, wherein each of $R'_1$ and $R'_2$ is an alkyl.

5. The compound of claim 3, wherein each of $R'_1$ and $R'_2$ is an alkyl containing at least 2 carbons.

6. The compound of claim 3, wherein each of $R'_1$ and $R'_2$ is an aryl.

7. The compound of claim 3, wherein the compound has the formula:

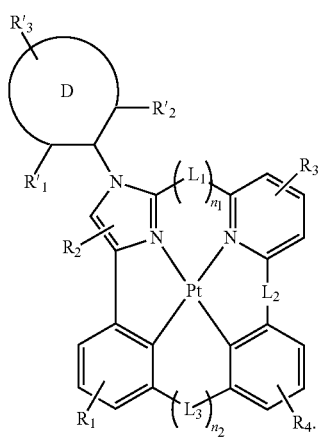

Formula II

8. The compound of claim 3, wherein the compound has the formula:

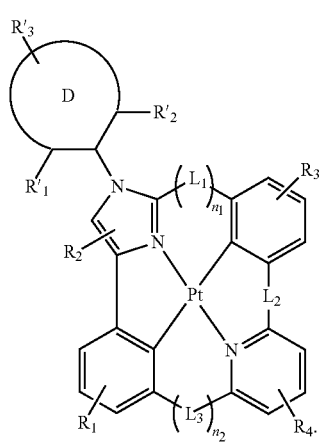

Formula III

9. The compound of claim 3, wherein the compound has the formula:

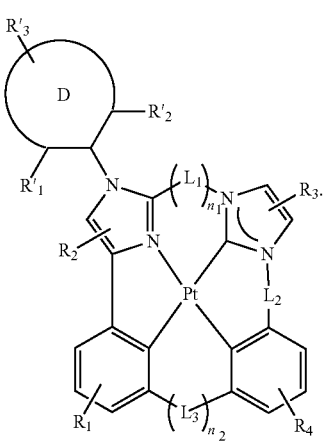

Formula VI

10. The compound of claim 3, wherein the compound has the formula:

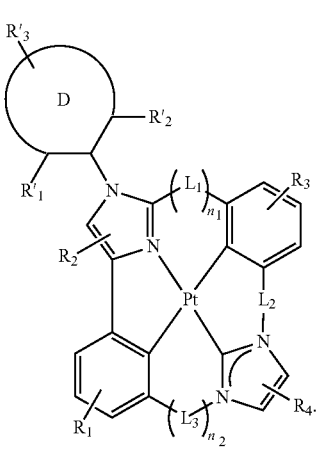

Formula VII

11. The compound of claim 1, wherein $L_1$ or $L_3$ is selected from the group consisting of O, S, $CH_2$, $CR'_2$, NR', $SiR'_2$ or BR'; and wherein R' is alkyl or aryl.

12. The compound of claim 1, wherein $L_2$ is selected from the group consisting of O, S, $CH_2$, $CR'_2$, NR', and $SiR'_2$;

wherein R' is alkyl or aryl; and wherein R' is optionally bonded to B or C.

13. The compound of claim 1, wherein $R_1$, $R_2$, $R_3$ and $R_4$ are each independently selected from the group consisting of hydrogen, deuterium, alkyl, aryl, cyclic alkyl, branched alkyl, heteroaryl, and fused aryl.

14. The compound of claim 1, wherein the compound is selected from the group consisting of:

Compound 1

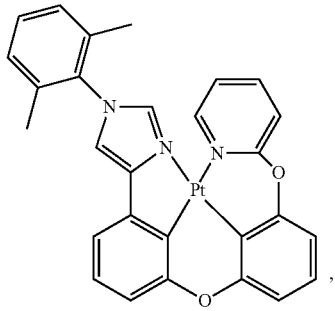

Compound 2

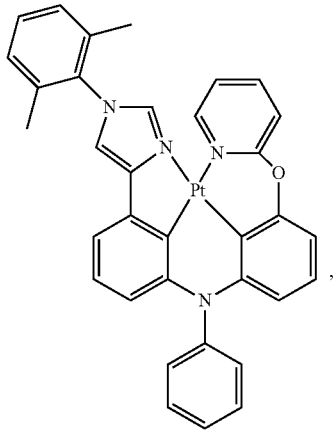

Compound 3

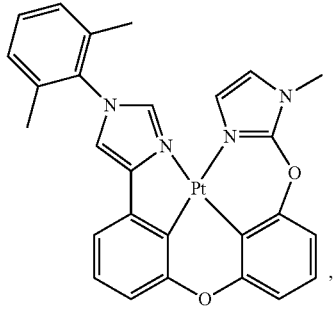

-continued

Compound 4

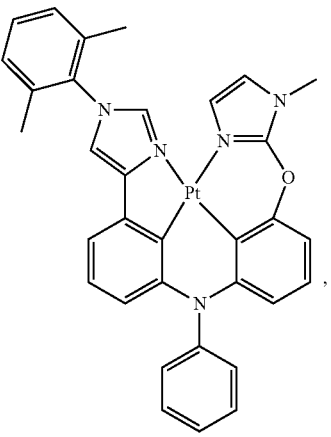

Compound 5

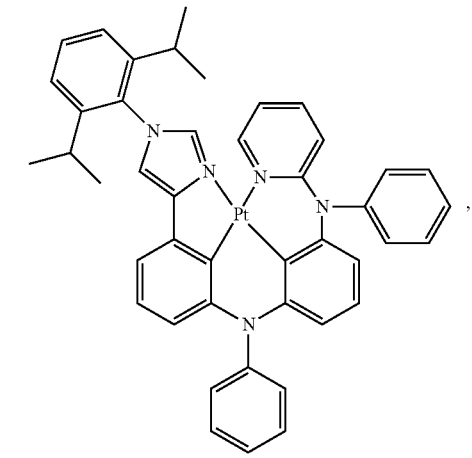

Compound 6

Compound 7

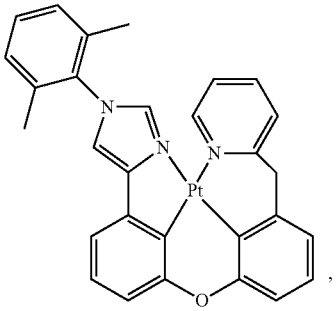

Compound 8
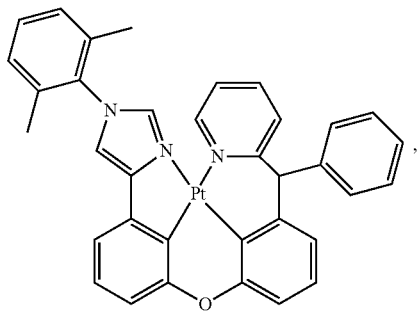
Compound 9
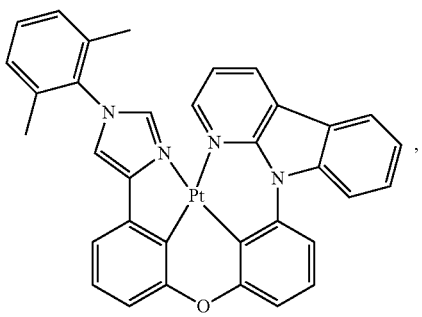
Compound 10
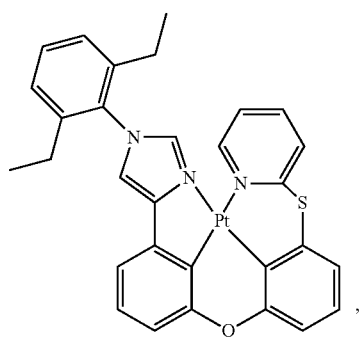
Compound 11
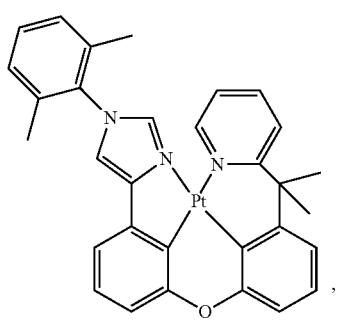
Compound 12
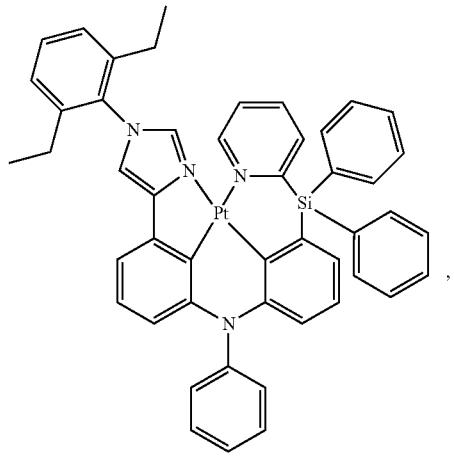
Compound 13
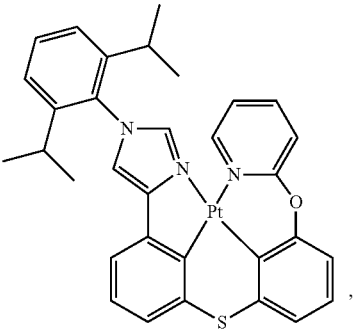
Compound 14
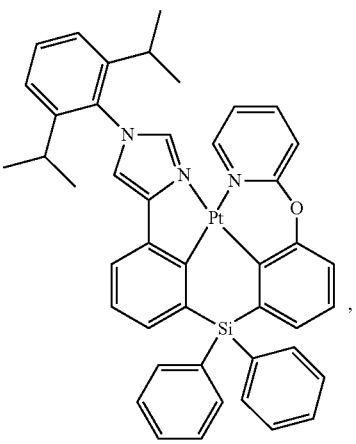
Compound 15
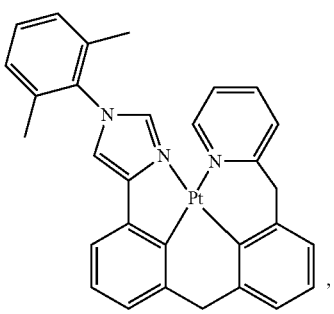

-continued
Compound 16
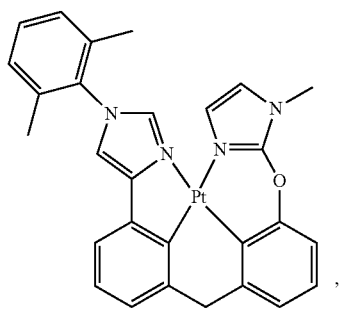
Compound 17
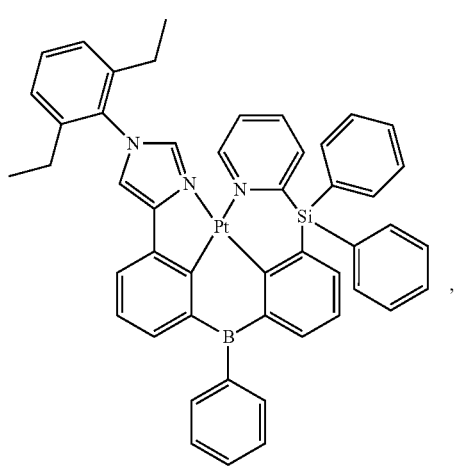
Compound 18
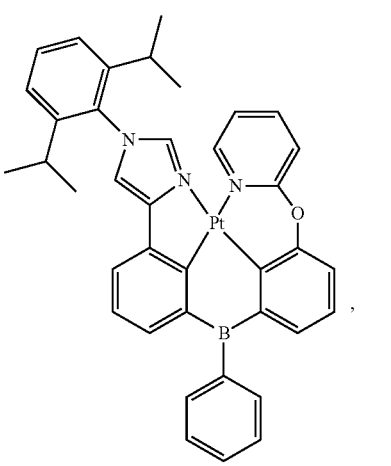
Compound 19
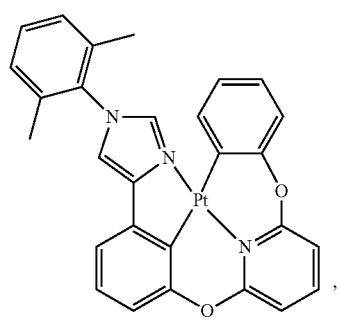
-continued
Compound 20
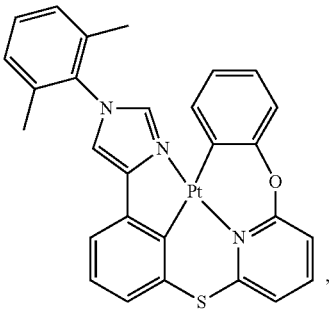
Compound 21
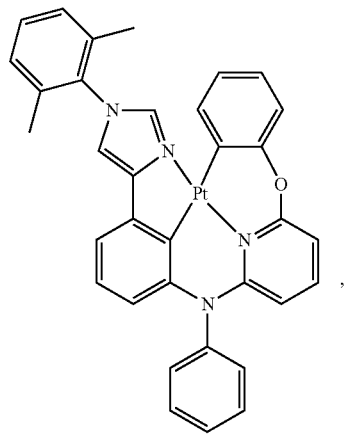
Compound 22
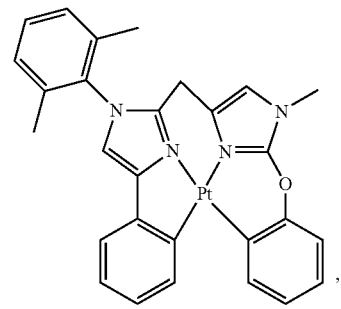
Compound 23
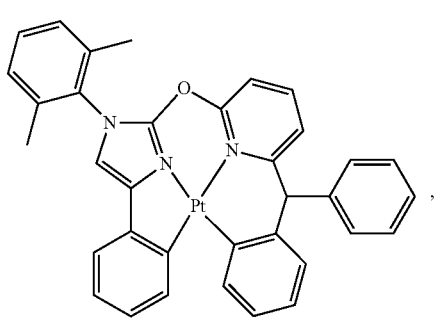

Compound 24
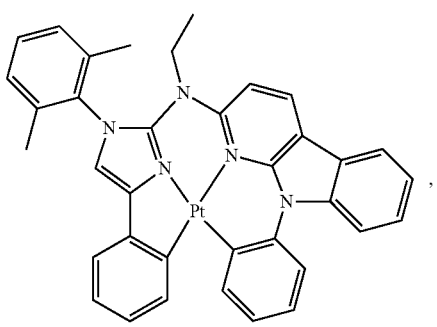
Compound 25
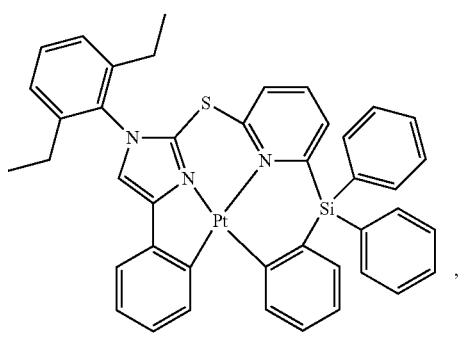
Compound 26
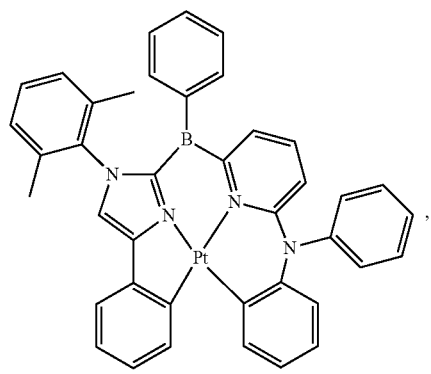
Compound 27
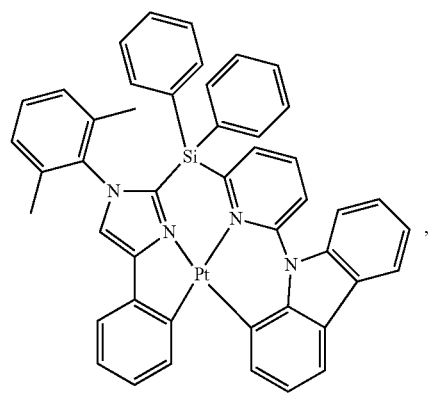
Compound 28
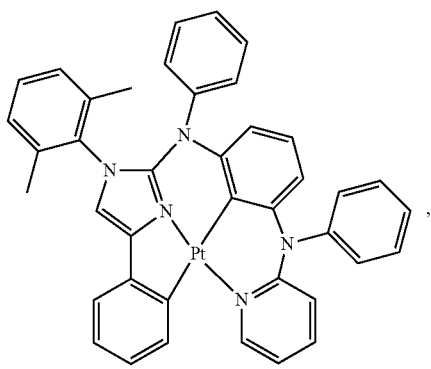
Compound 29
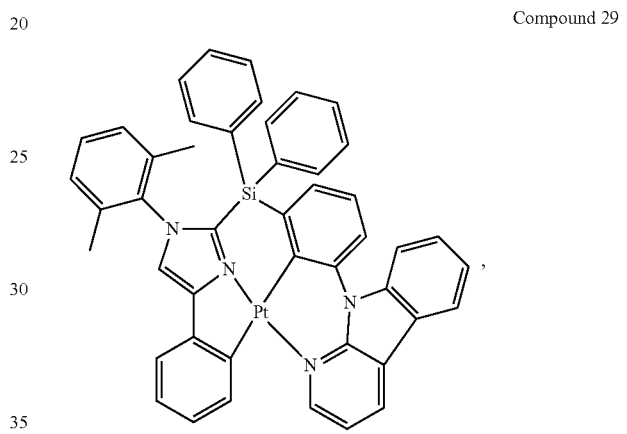
Compound 30
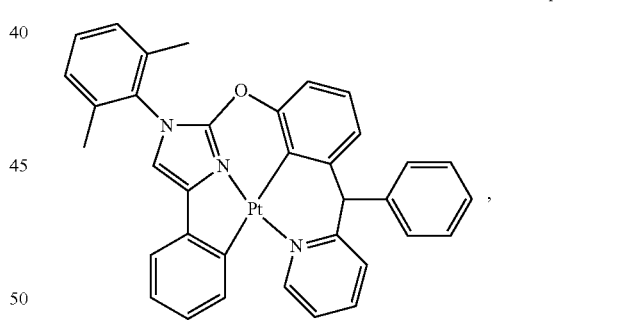
Compound 31
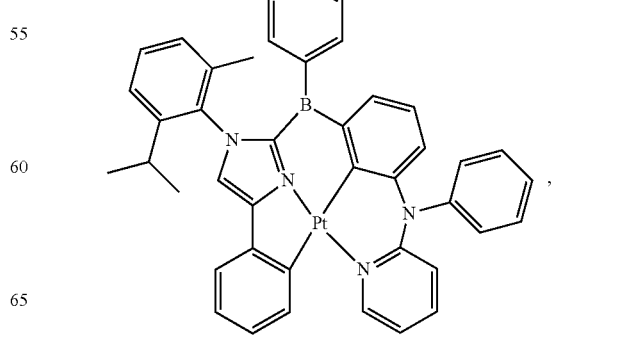

Compound 32
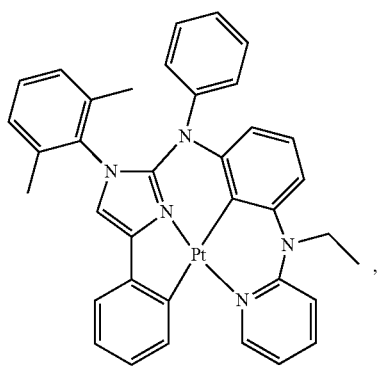
Compound 33
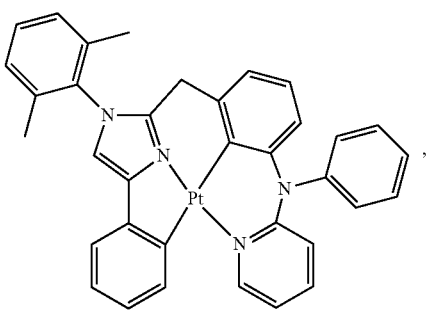
Compound 34
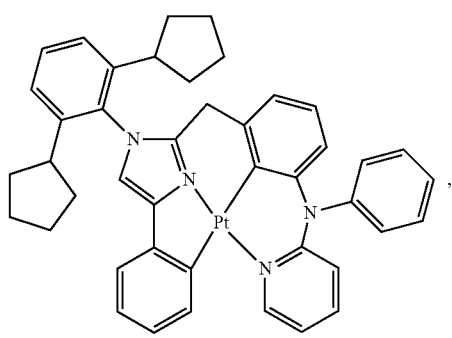
Compound 35
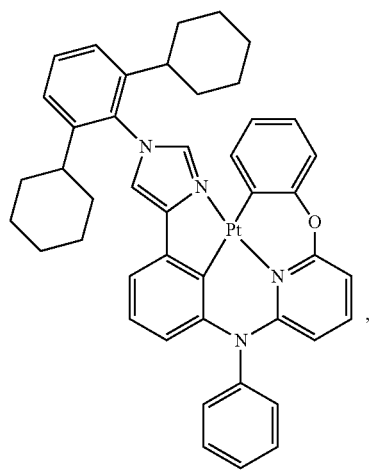
Compound 36
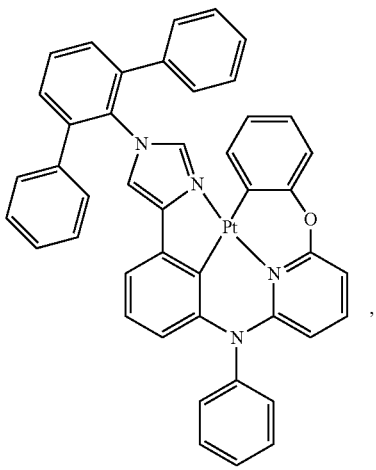
Compound 37
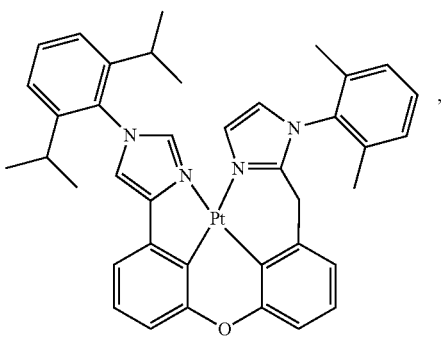
Compound 38
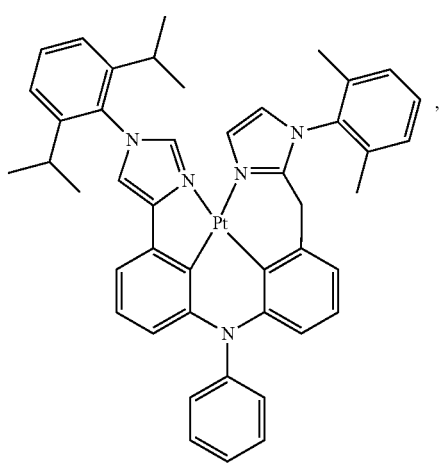

Compound 39
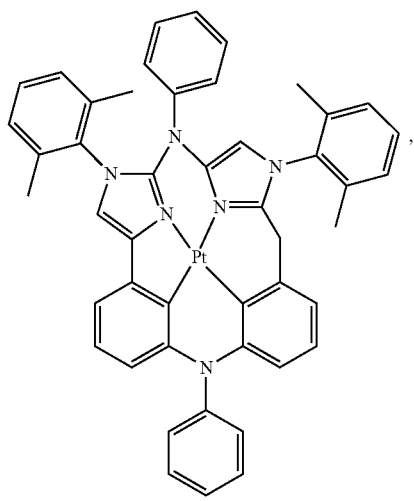
Compound 40
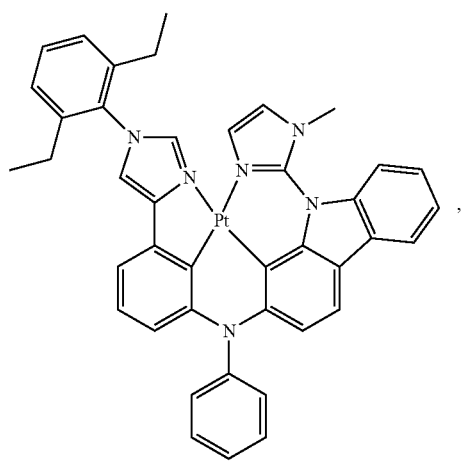
Compound 41
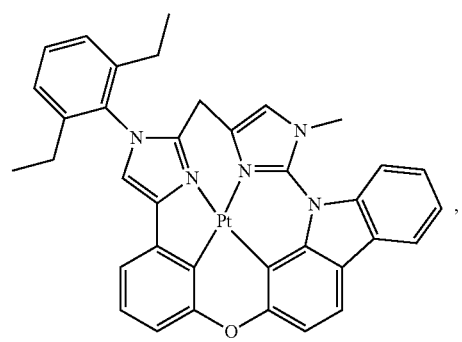
Compound 42
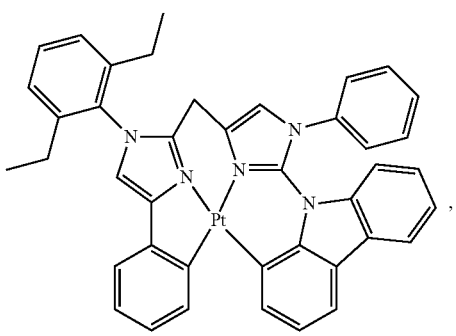
Compound 43
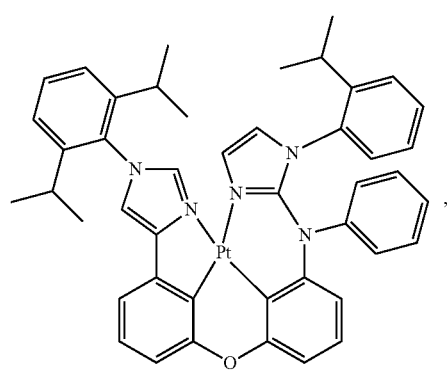
Compound 44
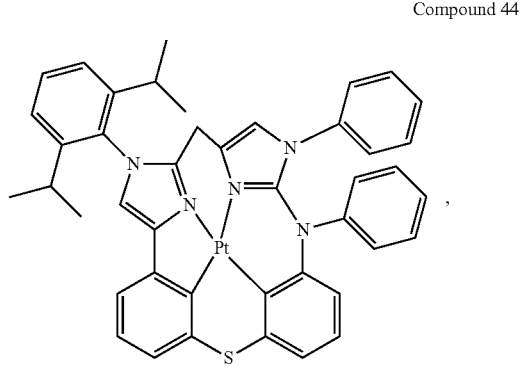
Compound 45
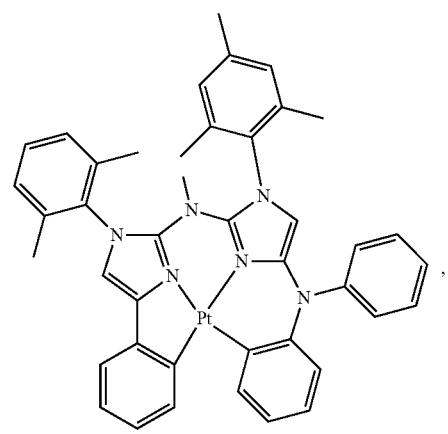

Compound 46
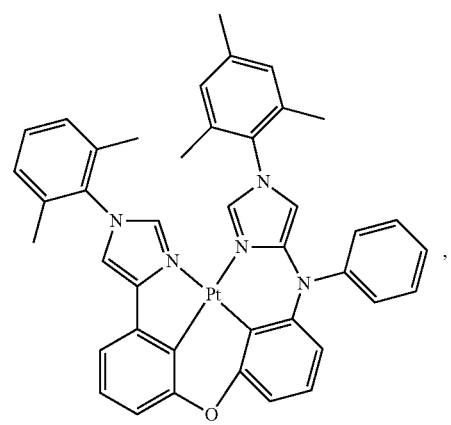
Compound 47
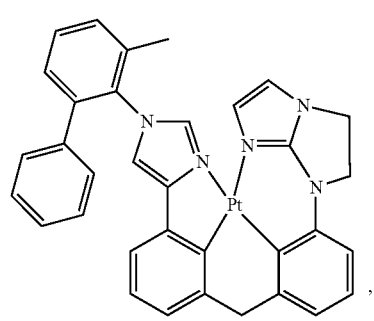
Compound 48
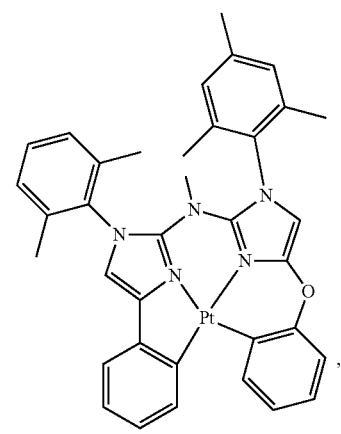
Compound 49
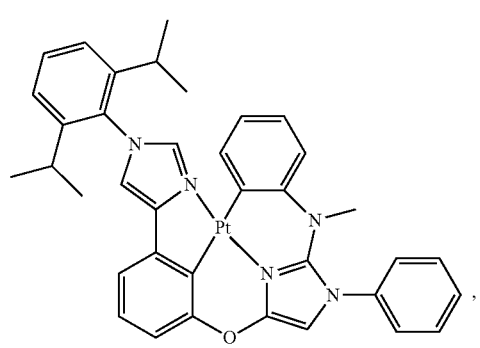
Compound 50
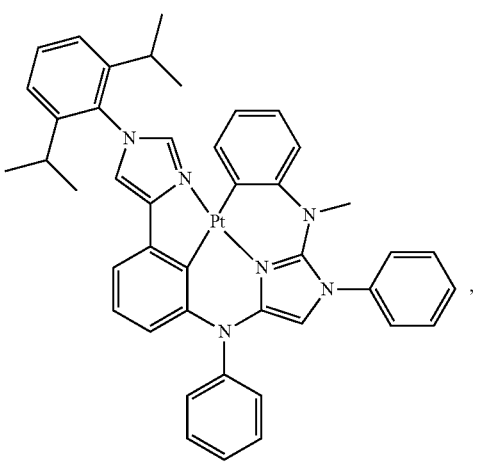
Compound 51
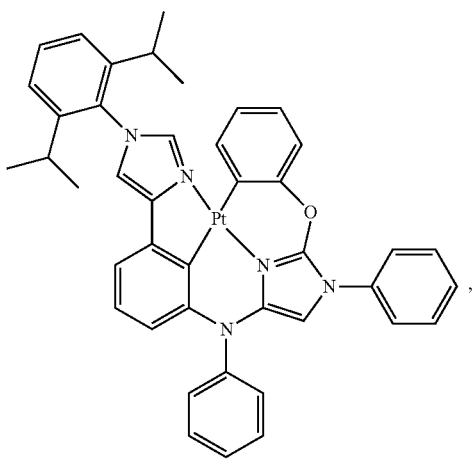
Compound 52
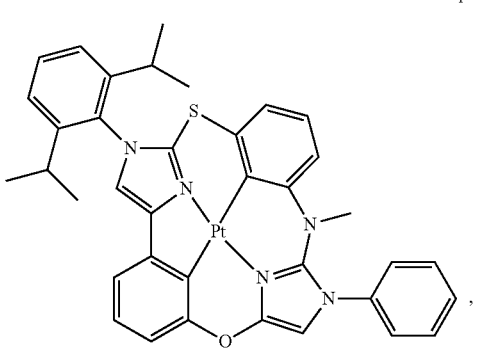

Compound 53
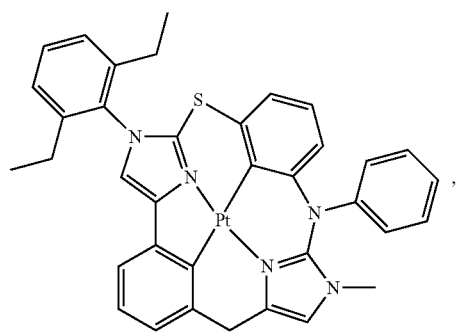
Compound 54
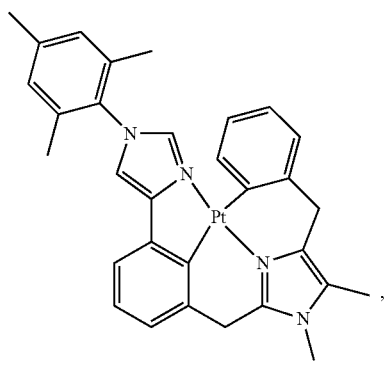
Compound 55
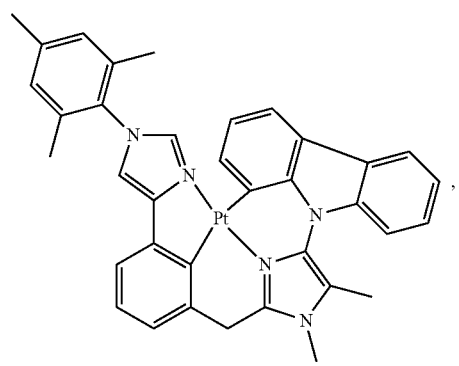
Compound 56
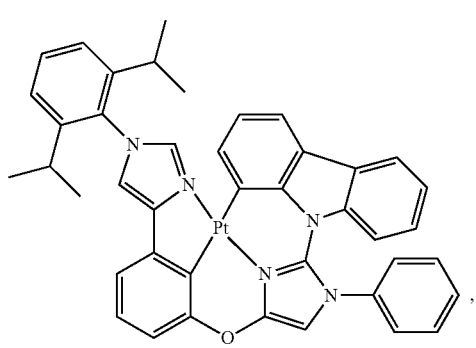
Compound 57
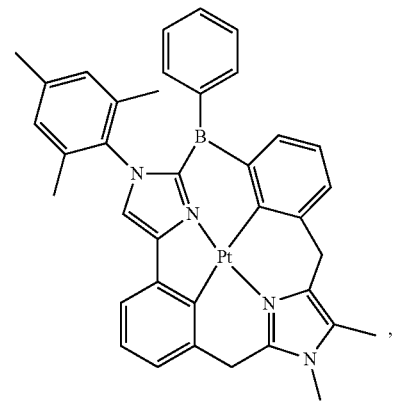
Compound 58
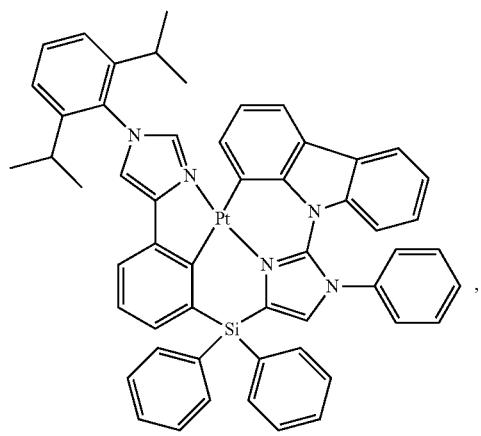
Compound 59
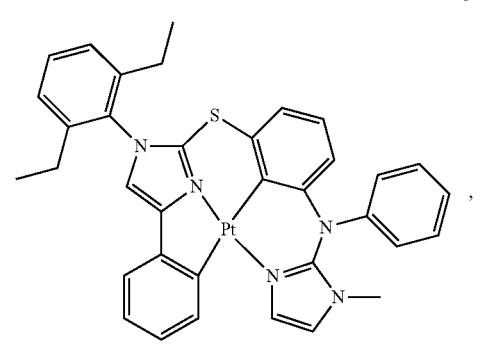
Compound 60
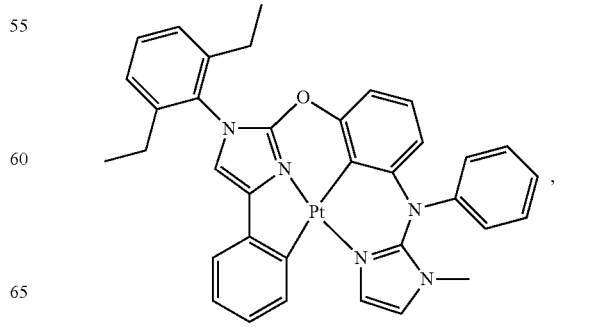

Compound 61
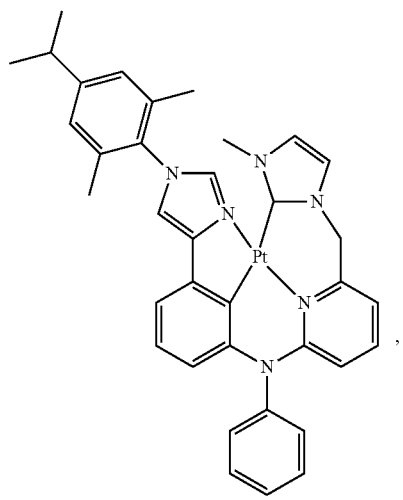
Compound 62
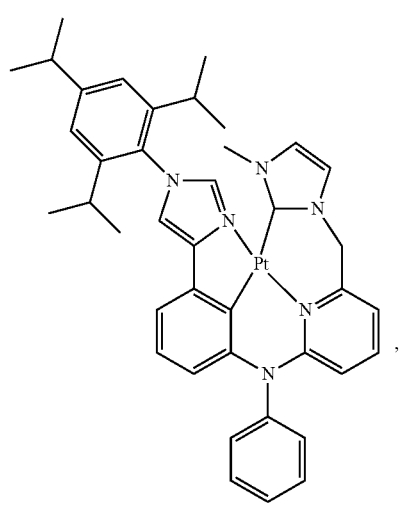
Compound 63
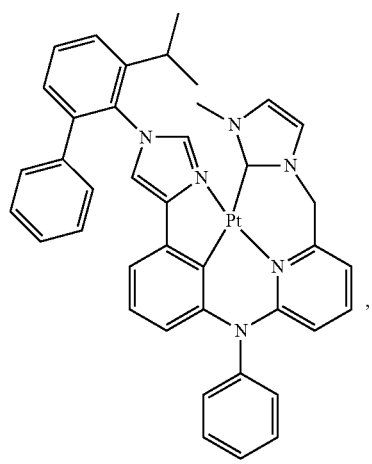
Compound 64
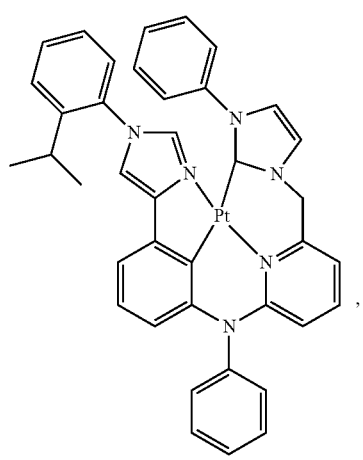
Compound 65
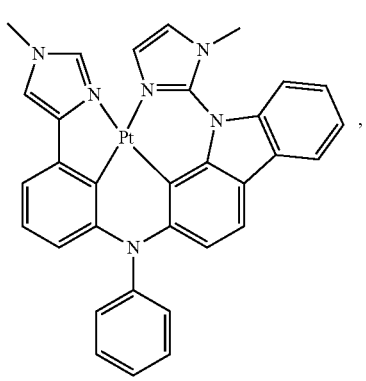
Compound 66
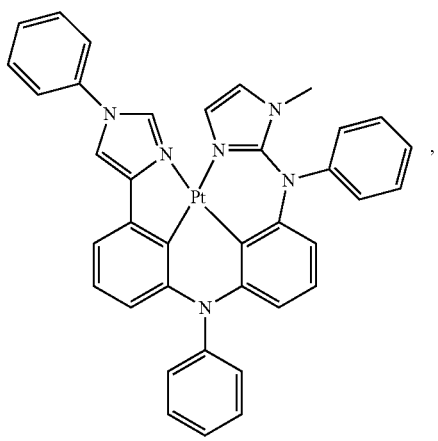

Compound 67
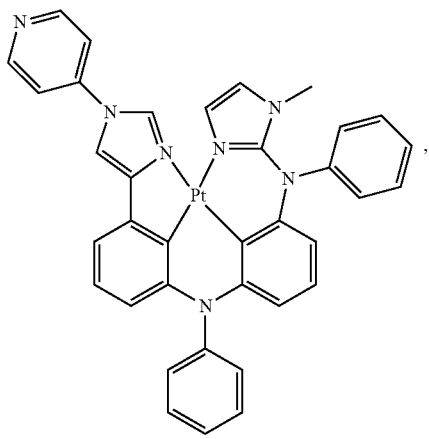
Compound 68
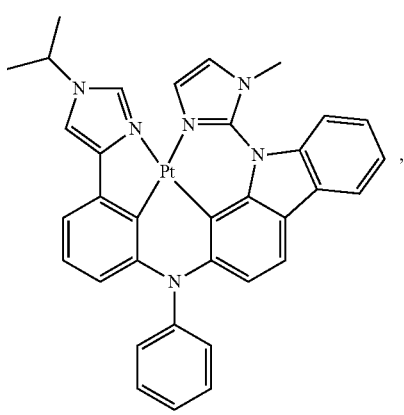
Compound 69
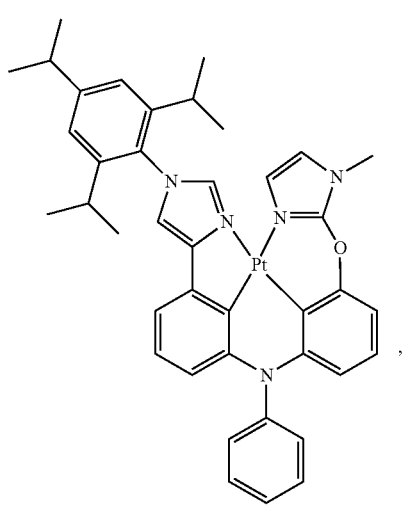
Compound 70
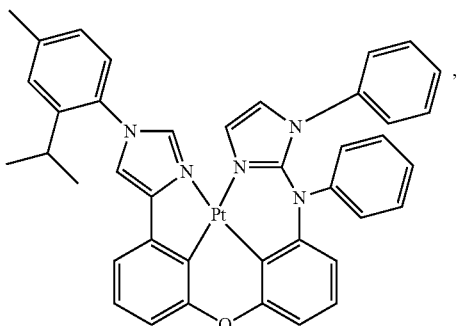
Compound 71
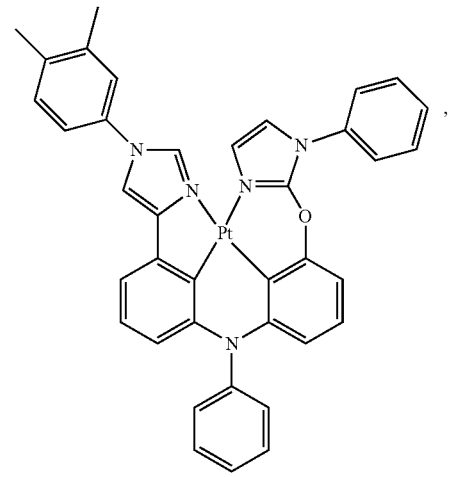
Compound 72
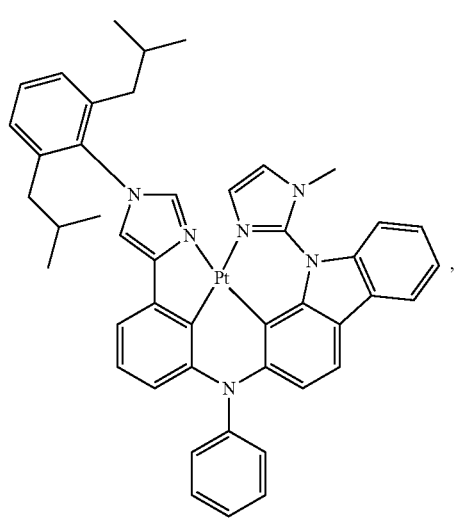

-continued

Compound 73

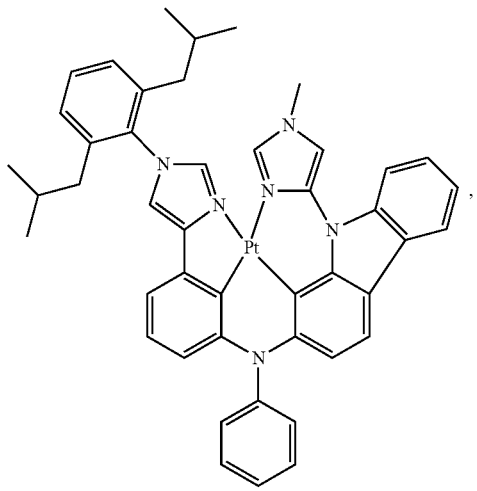

Compound 74

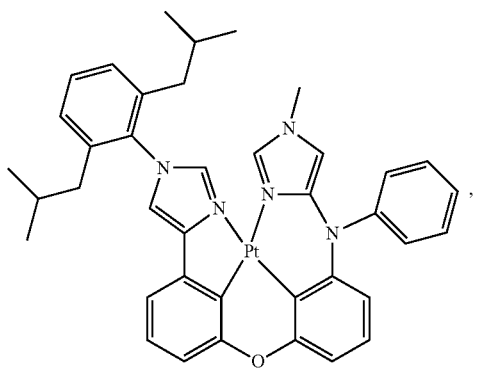

Compound 75

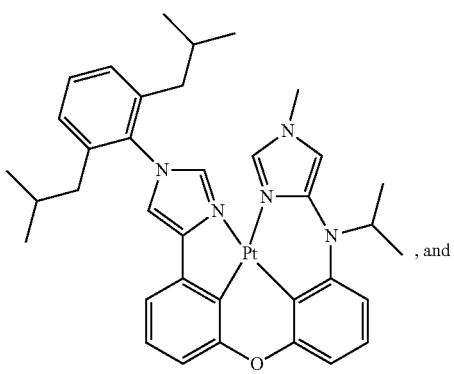, and

-continued

Compound 76

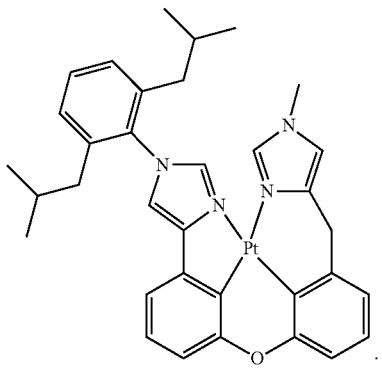

15. A first device comprising a first organic light emitting device, the first organic light emitting device comprising:
   an anode;
   a cathode; and
   an organic layer, disposed between the anode and the cathode, comprising a compound having the formula:

Formula I

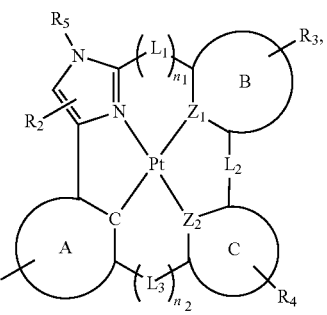

wherein A, B, and C are each independently a 5- or 6-membered carbocyclic or heterocyclic ring;
wherein $L_1$ and $L_3$ are independently selected from the group consisting of a single bond, BR, NR, PR, O, S, Se, C=O, S=O, $SO_2$, CRR', SiRR', and GeRR';
wherein $L_2$ is selected from the group consisting of BR, NR, PR, O, S, Se, C=O, S=O, $SO_2$, CRR', SiRR', and GeRR';
wherein $n_1$ is 0, 1;
wherein $n_2$ is 0, 1;
wherein $n_1+n_2$ is at least equal to 1;
wherein $Z_1$ and $Z_2$ are independently a nitrogen atom or a carbon atom;
wherein $R_1$, $R_2$, $R_3$, and $R_4$ may represent mono-, di-, tri-, or tetra-substitutions;
wherein R, R', $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R_1$ is optionally fused to A;
wherein $R_3$ is optionally fused to B;
wherein $R_4$ is optionally fused to C;
wherein $R_3$ and $R_4$ are optionally joined to form into a ring;
wherein $R_3$ and $L_2$ are optionally joined to form into a ring;

wherein R$_4$ and L$_2$ are optionally joined to form into a ring; and wherein at least one of the following (i)-(vi) is true:
(i) n$_1$=0 and n$_2$=1;
(ii) wherein R$_5$ is

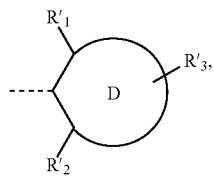

wherein R'$_1$ and R'$_2$ are independently selected from the group consisting of halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, partially or fully deuterated variations thereof, and combinations thereof;

wherein D is 5-membered or 6-membered carbocyclic or heterocyclic ring that is optionally further substituted with R'$_3$; and wherein R'$_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

(iii) wherein the compound has the structure of Formula IIA,

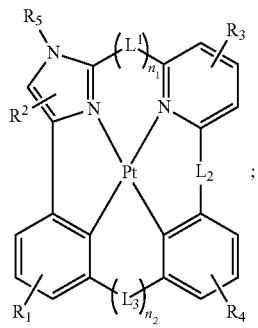

(iv) wherein the compound has the structure of Formula IIIA,

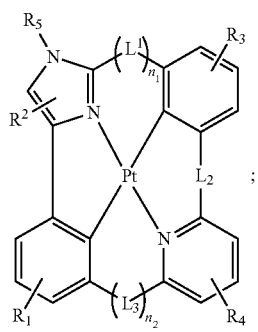

(v) wherein the compound has the structure of Formula VIA,

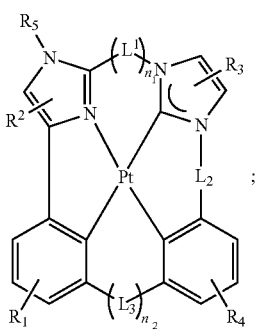

and
(vi) wherein the compound has the structure of Formula VIIA,

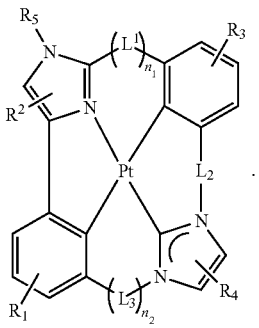

16. The compound of claim 1, wherein n$_1$=0 and n$_2$=1.

17. The compound of claim 1, wherein the compound has the structure of Formula IIA,

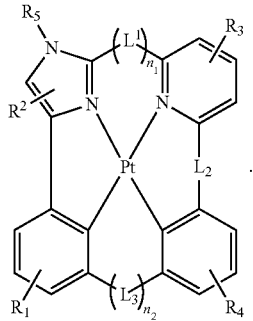

18. The compound of claim 1, wherein the compound has the structure of Formula IIIA,

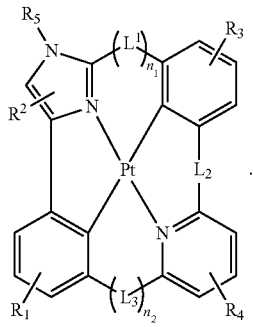

19. The compound of claim 1, wherein the compound has the structure of Formula VIA,
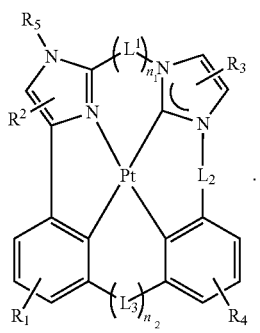
20. The compound of claim 1, wherein the compound has the structure of Formula VIIA,
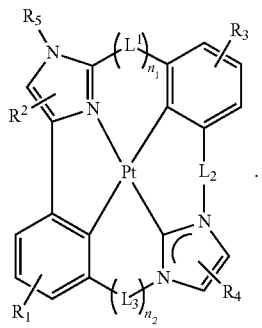
* * * * *